United States Patent
Wang

(10) Patent No.: US 11,254,722 B2
(45) Date of Patent: Feb. 22, 2022

(54) RECOMBINANT PROTEINS AND USES THEREOF

(71) Applicant: ACADEMIA SINICA, Taipei (TW)

(72) Inventor: Elizabeth Wang, Taipei (TW)

(73) Assignee: Academia Sinica, Taipei (TW)

(*) Notice: Subject to any disclaimer, the term of this patent is extended or adjusted under 35 U.S.C. 154(b) by 308 days.

(21) Appl. No.: 16/483,371

(22) PCT Filed: Feb. 6, 2018

(86) PCT No.: PCT/US2018/016939
§ 371 (c)(1),
(2) Date: Aug. 2, 2019

(87) PCT Pub. No.: WO2018/145048
PCT Pub. Date: Aug. 9, 2018

(65) Prior Publication Data
US 2019/0359666 A1 Nov. 28, 2019

Related U.S. Application Data

(60) Provisional application No. 62/454,902, filed on Feb. 6, 2017.

(51) Int. Cl.
| | | |
|---|---|---|
| A61K 38/00 | (2006.01) | |
| C07K 14/47 | (2006.01) | |
| A61P 35/00 | (2006.01) | |
| C07K 14/52 | (2006.01) | |
| A61K 33/243 | (2019.01) | |
| A61K 31/351 | (2006.01) | |
| A61K 31/437 | (2006.01) | |
| A61K 31/4545 | (2006.01) | |
| A61K 31/517 | (2006.01) | |
| A61K 31/5377 | (2006.01) | |

(52) U.S. Cl.
CPC .......... *C07K 14/4743* (2013.01); *A61P 35/00* (2018.01); *C07K 14/52* (2013.01); *A61K 31/351* (2013.01); *A61K 31/437* (2013.01); *A61K 31/4545* (2013.01); *A61K 31/517* (2013.01); *A61K 31/5377* (2013.01); *A61K 33/243* (2019.01); *A61K 38/00* (2013.01); *C07K 2319/30* (2013.01)

(58) Field of Classification Search
CPC .............................. C07K 14/4743; A61P 35/00
See application file for complete search history.

(56) References Cited

U.S. PATENT DOCUMENTS

| 6,812,339 B1 | 11/2004 | Venter et al. | |
|---|---|---|---|
| 2002/0072589 A1 | 6/2002 | Mascarenhas et al. | |
| 2014/0005098 A1* | 1/2014 | Godeau ................. | A61P 21/02 514/1.8 |
| 2015/0290297 A1 | 10/2015 | Godeau et al. | |

FOREIGN PATENT DOCUMENTS

| WO | WO 89/09268 | * 10/1989 |
|---|---|---|
| WO | WO 2012/113900 A1 | 8/2012 |

OTHER PUBLICATIONS

Skolnick et al. (Trends in Biotech., 18(1):34-39, 2000) (Year: 2000).*

Cagiada et al Mol. Biol. Evol. Doi:10.1093/molbev/msab095, 12 pages, (2021) (Year: 2021).*

* cited by examiner

*Primary Examiner* — Sheela J. Huff

(74) *Attorney, Agent, or Firm* — Muncy, Geissler, Olds & Lowe, P.C.

(57) ABSTRACT

Disclosed herein are recombinant proteins including an IGFBP3 or a biologically active fragment thereof and an IgG Fc portion linked to the C-terminus of the IGFBP3 variant. The recombinant proteins including at least one additional domain of other growth factors are also disclosed. Methods for treating tumors, in particular, tumors resistant to the targeted therapy, using the above-mentioned recombinant proteins are also provided.

18 Claims, 20 Drawing Sheets

Specification includes a Sequence Listing.

| A549 (Lung) 5-87 | | D3 |
|---|---|---|
| No add | | |
| 0.5 uM AZD9291 | | |
| 30 nM trametinib | | |

FIG. 18A

| A549 (Lung) 5-75 | | D3 |
|---|---|---|
| | | |
| 6 uM cisplatin | | |

Fig. 18B

Gefitinib Inhibition of PC-9

D3 inhibits GF Rescue of 2 uM gefitinib-treated PC-9 cells

Plate 2000 cells/well in 6 well; grow 18 days w4-1 PC-9

SEQUENCE LISTING

<160> NUMBER OF SEQ ID NOS: 32

<210> SEQ ID NO 1
<211> LENGTH: 289
<212> TYPE: PRT
<213> ORGANISM: Artificial Sequence
<220> FEATURE:
<223> OTHER INFORMATION: Synthesized

<400> SEQUENCE: 1

```
Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Arg Leu Arg Ala Tyr Leu Leu Pro Ala
        115                 120                 125

Pro Pro Ala Pro Gly Asn Ala Ser Glu Ser Glu Glu Asp Arg Ser Ala
    130                 135                 140

Gly Ser Val Glu Ser Pro Ser Val Ser Ser Thr His Arg Val Ser Asp
145                 150                 155                 160

Pro Lys Phe His Pro Leu His Ser Lys Ile Ile Ile Lys Lys Gly
                165                 170                 175

His Ala Lys Asp Ser Gln Arg Tyr Lys Val Asp Tyr Glu Ser Gln Ser
            180                 185                 190

Thr Asp Thr Gln Asn Phe Ser Ser Glu Ser Lys Arg Glu Thr Glu Tyr
        195                 200                 205

Gly Pro Cys Arg Arg Glu Met Glu Asp Thr Leu Asn His Leu Lys Phe
    210                 215                 220

Leu Asn Val Leu Ser Pro Arg Gly Val His Ile Pro Asn Cys Asp Lys
225                 230                 235                 240

Lys Gly Phe Tyr Lys Lys Lys Gln Cys Arg Pro Ser Lys Gly Arg Lys
                245                 250                 255
```

Arg Gly Phe Cys Trp Cys Val Asp Lys Tyr Gly Gln Pro Leu Pro Gly
            260                 265                 270

Tyr Thr Thr Lys Gly Lys Glu Asp Val His Cys Tyr Ser Met Gln Ser
        275                 280                 285

Lys

<210> SEQ ID NO 2
<211> LENGTH: 234
<212> TYPE: PRT
<213> ORGANISM: Artificial Sequence
<220> FEATURE:
<223> OTHER INFORMATION: Synthesized

<400> SEQUENCE: 2

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Lys Gly His Ala Lys Asp Ser Gln Arg
        115                 120                 125

Tyr Lys Val Asp Tyr Glu Ser Gln Ser Thr Asp Thr Gln Asn Phe Ser
    130                 135                 140

Ser Glu Ser Lys Arg Glu Thr Glu Tyr Gly Pro Cys Arg Arg Glu Met
145                 150                 155                 160

Glu Asp Thr Leu Asn His Leu Lys Phe Leu Asn Val Leu Ser Pro Arg
                165                 170                 175

Gly Val His Ile Pro Asn Cys Asp Lys Lys Gly Phe Tyr Lys Lys Lys
            180                 185                 190

Gln Cys Arg Pro Ser Lys Gly Arg Lys Arg Gly Phe Cys Trp Cys Val
        195                 200                 205

Asp Lys Tyr Gly Gln Pro Leu Pro Gly Tyr Thr Thr Lys Gly Lys Glu
210                 215                 220

Asp Val His Cys Tyr Ser Met Gln Ser Lys
225                 230

<210> SEQ ID NO 3
<211> LENGTH: 237
<212> TYPE: PRT
<213> ORGANISM: Artificial Sequence
<220> FEATURE:
<223> OTHER INFORMATION: Synthesized

<400> SEQUENCE: 3

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Arg Cys Glu Pro Cys Asp Ala Arg Ala Leu Ala Gln
            35                  40                  45

Cys Ala Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Met Glu Leu Ala Glu Ile Glu Ala Ile Gln Glu Ser Leu Gln Pro Ser
            115                 120                 125

Asp Lys Asp Glu Gly Asp His Pro Asn Asn Ser Phe Ser Pro Cys Ser
130                 135                 140

Ala His Asp Arg Arg Cys Leu Gln Glu Thr Glu Tyr Gly Pro Cys Arg
145                 150                 155                 160

Arg Glu Met Glu Asp Thr Leu Asn His Leu Lys Phe Leu Asn Val Leu
                165                 170                 175

Ser Pro Arg Gly Val His Ile Pro Asn Cys Asp Lys Lys Gly Phe Tyr
            180                 185                 190

Lys Lys Lys Gln Cys Arg Pro Ser Lys Gly Arg Lys Arg Gly Phe Cys
            195                 200                 205

Trp Cys Val Asp Lys Tyr Gly Gln Pro Leu Pro Gly Tyr Thr Thr Lys
            210                 215                 220

Gly Lys Glu Asp Val His Cys Tyr Ser Met Gln Ser Lys
225                 230                 235

<210> SEQ ID NO 4
<211> LENGTH: 248
<212> TYPE: PRT
<213> ORGANISM: Artificial Sequence
<220> FEATURE:
<223> OTHER INFORMATION: Synthesized

<400> SEQUENCE: 4

Met Ser Glu Val Pro Val Ala Arg Val Trp Leu Val Leu Leu Leu
1               5                   10                  15

Thr Val Gln Val Gly Val Thr Ala Gly Gly Ala Ser Ser Ala Gly Leu
                20                  25                  30

Gly Pro Val Arg Cys Glu Pro Cys Asp Ala Arg Ala Leu Ala Gln
            35                  40                  45

Cys Ala Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Pro Ala Arg Ala Pro Ala Val Ala Glu Glu Asn Pro Lys Glu Ser Lys
            115                 120                 125

Pro Gln Ala Gly Thr Ala Arg Pro Gln Asp Val Asn Arg Arg Asp Gln
            130                 135                 140

Gln Arg Asn Pro Gly Thr Ser Thr Thr Pro Ser Gln Pro Asn Ser Ala
145                 150                 155                 160

```
Gly Val Gln Asp Thr Glu Met Gly Pro Cys Arg Arg Glu Met Glu Asp
                165                 170                 175

Thr Leu Asn His Leu Lys Phe Leu Asn Val Leu Ser Pro Arg Gly Val
            180                 185                 190

His Ile Pro Asn Cys Asp Lys Lys Gly Phe Tyr Lys Lys Lys Gln Cys
        195                 200                 205

Arg Pro Ser Lys Gly Arg Lys Arg Gly Phe Cys Trp Cys Val Asp Lys
    210                 215                 220

Tyr Gly Gln Pro Leu Pro Gly Tyr Thr Thr Lys Gly Lys Glu Asp Val
225                 230                 235                 240

His Cys Tyr Ser Met Gln Ser Lys
                245
```

<210> SEQ ID NO 5
<211> LENGTH: 274
<212> TYPE: PRT
<213> ORGANISM: Artificial Sequence
<220> FEATURE:
<223> OTHER INFORMATION: Synthesized

<400> SEQUENCE: 5

```
Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Arg Pro Ala Pro Pro Ala Pro Gly Asn
        115                 120                 125

Ala Ser Glu Ser Glu Glu Asp Arg Ser Ala Gly Ser Val Glu Ser Pro
    130                 135                 140

Ser Val Ser Ser Thr His Arg Val Ser Asp Pro Lys Phe His Pro Lys
145                 150                 155                 160

Gly His Ala Lys Asp Ser Gln Arg Tyr Lys Val Asp Tyr Glu Ser Gln
                165                 170                 175

Ser Thr Asp Thr Gln Asn Phe Ser Ser Glu Ser Lys Arg Glu Thr Glu
            180                 185                 190

Tyr Gly Pro Cys Arg Arg Glu Met Glu Asp Thr Leu Asn His Leu Lys
        195                 200                 205

Phe Leu Asn Val Leu Ser Pro Arg Gly Val His Ile Pro Asn Cys Asp
    210                 215                 220

Lys Lys Gly Phe Tyr Lys Lys Lys Gln Cys Arg Pro Ser Lys Gly Arg
225                 230                 235                 240

Lys Arg Gly Phe Cys Trp Cys Val Asp Lys Tyr Gly Gln Pro Leu Pro
                245                 250                 255

Gly Tyr Thr Thr Lys Gly Lys Glu Asp Val His Cys Tyr Ser Met Gln
            260                 265                 270
```

Ser Lys

<210> SEQ ID NO 6
<211> LENGTH: 268
<212> TYPE: PRT
<213> ORGANISM: Artificial Sequence
<220> FEATURE:
<223> OTHER INFORMATION: Synthesized

<400> SEQUENCE: 6

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Arg Pro Ala Pro Ala Pro Gly Asn
        115                 120                 125

Ala Ser Glu Ser Glu Glu Asp Arg Ser Ala Gly Ser Val Glu Ser Pro
130                 135                 140

Ser Val Ser Ser Thr His Arg Val Ser Asp Pro Lys Phe His Pro Lys
145                 150                 155                 160

Gly His Ala Lys Val Asp Tyr Glu Ser Gln Ser Thr Asp Thr Gln Asn
                165                 170                 175

Phe Ser Ser Glu Ser Lys Arg Glu Thr Glu Tyr Gly Pro Cys Arg Arg
            180                 185                 190

Glu Met Glu Asp Thr Leu Asn His Leu Lys Phe Leu Asn Val Leu Ser
        195                 200                 205

Pro Arg Gly Val His Ile Pro Asn Cys Asp Lys Lys Gly Phe Tyr Lys
    210                 215                 220

Lys Lys Gln Cys Arg Pro Ser Lys Gly Arg Lys Arg Gly Phe Cys Trp
225                 230                 235                 240

Cys Val Asp Lys Tyr Gly Gln Pro Leu Pro Gly Tyr Thr Thr Lys Gly
                245                 250                 255

Lys Glu Asp Val His Cys Tyr Ser Met Gln Ser Lys
            260                 265

<210> SEQ ID NO 7
<211> LENGTH: 512
<212> TYPE: PRT
<213> ORGANISM: Artificial Sequence
<220> FEATURE:
<223> OTHER INFORMATION: Synthesized

<400> SEQUENCE: 7

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

```
Gly Pro Val Arg Cys Glu Pro Cys Asp Ala Arg Ala Leu Ala Gln
             35                  40                  45

Cys Ala Pro Pro Ala Val Cys Ala Glu Leu Val Arg Glu Pro Gly
 50                  55                  60

Cys Gly Cys Cys Leu Thr Cys Ala Leu Ser Glu Gly Gln Pro Cys Gly
 65                  70                  75                  80

Ile Tyr Thr Glu Arg Cys Gly Ser Gly Leu Arg Cys Gln Pro Ser Pro
                 85                  90                  95

Asp Glu Ala Arg Pro Leu Gln Ala Leu Leu Asp Gly Arg Gly Leu Cys
            100                 105                 110

Val Asn Ala Ser Ala Val Ser Arg Leu Arg Ala Tyr Leu Leu Pro Ala
            115                 120                 125

Pro Pro Ala Pro Gly Asn Ala Ser Glu Ser Glu Glu Asp Arg Ser Ala
130                 135                 140

Gly Ser Val Glu Ser Pro Ser Val Ser Ser Thr His Arg Val Ser Asp
145                 150                 155                 160

Pro Lys Phe His Pro Leu His Ser Lys Ile Ile Ile Lys Lys Gly
                165                 170                 175

His Ala Lys Asp Ser Gln Arg Tyr Lys Val Asp Tyr Glu Ser Gln Ser
            180                 185                 190

Thr Asp Thr Gln Asn Phe Ser Ser Glu Ser Lys Arg Glu Thr Glu Tyr
            195                 200                 205

Gly Pro Cys Arg Arg Glu Met Glu Asp Thr Leu Asn His Leu Lys Phe
            210                 215                 220

Leu Asn Val Leu Ser Pro Arg Gly Val His Ile Pro Asn Cys Asp Lys
225                 230                 235                 240

Lys Gly Phe Tyr Lys Lys Gln Cys Arg Pro Ser Lys Gly Arg Lys
                245                 250                 255

Arg Gly Phe Cys Trp Cys Val Asp Lys Tyr Gly Gln Pro Leu Pro Gly
            260                 265                 270

Tyr Thr Thr Lys Gly Lys Glu Asp Val His Cys Tyr Ser Met Gln Ser
            275                 280                 285

Lys Val Glu Cys Pro Pro Cys Pro Ala Pro Val Ala Gly Pro Ser
            290                 295                 300

Val Phe Leu Phe Pro Pro Lys Pro Lys Asp Gln Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
            355                 360                 365

Ser Val Leu Thr Val Leu His Gln Asp Trp Leu Asn Gly Lys Glu Tyr
            370                 375                 380

Lys Cys Lys Val Ser Asn Lys Gly Leu Pro Ser Ser Ile Glu Lys Thr
385                 390                 395                 400

Ile Ser Lys Ala Lys Gly Gln Pro Arg Glu Pro Gln Val Tyr Thr Leu
                405                 410                 415

Pro Pro Ser Arg Glu Glu Met Thr Lys Asn Gln Val Ser Leu Thr Cys
            420                 425                 430

Leu Val Lys Gly Phe Tyr Pro Ser Asp Ile Ala Val Glu Trp Glu Ser
            435                 440                 445

Asn Gly Gln Pro Glu Asn Asn Tyr Lys Thr Thr Pro Pro Val Leu Asp
```

```
                450              455              460
Ser Asp Gly Ser Phe Phe Leu Tyr Ser Lys Leu Thr Val Asp Lys Ser
465                 470              475              480

Arg Trp Gln Gln Gly Asn Val Phe Ser Cys Ser Val Met His Glu Gly
                485              490              495

Leu His Asn His Tyr Thr Gln Lys Ser Leu Ser Leu Ser Pro Gly Lys
                500              505              510

<210> SEQ ID NO 8
<211> LENGTH: 457
<212> TYPE: PRT
<213> ORGANISM: Artificial Sequence
<220> FEATURE:
<223> OTHER INFORMATION: Synthesized

<400> SEQUENCE: 8

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Lys Gly His Ala Lys Asp Ser Gln Arg
        115                 120                 125

Tyr Lys Val Asp Tyr Glu Ser Gln Ser Thr Asp Thr Gln Asn Phe Ser
    130                 135                 140

Ser Glu Ser Lys Arg Glu Thr Glu Tyr Gly Pro Cys Arg Arg Glu Met
145                 150                 155                 160

Glu Asp Thr Leu Asn His Leu Lys Phe Leu Asn Val Leu Ser Pro Arg
                165                 170                 175

Gly Val His Ile Pro Asn Cys Asp Lys Lys Gly Phe Tyr Lys Lys Lys
            180                 185                 190

Gln Cys Arg Pro Ser Lys Gly Arg Lys Arg Gly Phe Cys Trp Cys Val
        195                 200                 205

Asp Lys Tyr Gly Gln Pro Leu Pro Gly Tyr Thr Thr Lys Gly Lys Glu
    210                 215                 220

Asp Val His Cys Tyr Ser Met Gln Ser Lys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Gln Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
```

```
                305                 310                 315                 320
Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
                340                 345                 350

Pro Arg Glu Pro Gln Val Tyr Thr Leu Pro Pro Ser Arg Glu Glu Met
                355                 360                 365

Thr Lys Asn Gln Val Ser Leu Thr Cys Leu Val Lys Gly Phe Tyr Pro
                370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Gly Leu His Asn His Tyr Thr Gln
                435                 440                 445

Lys Ser Leu Ser Leu Ser Pro Gly Lys
                450                 455

<210> SEQ ID NO 9
<211> LENGTH: 460
<212> TYPE: PRT
<213> ORGANISM: Artificial Sequence
<220> FEATURE:
<223> OTHER INFORMATION: Synthesized

<400> SEQUENCE: 9

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
                20                  25                  30

Gly Pro Val Val Arg Cys Glu Pro Cys Asp Ala Arg Ala Leu Ala Gln
                35                  40                  45

Cys Ala Pro Pro Pro Ala Val Cys Ala Glu Leu Val Arg Glu Pro Gly
                50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
                100                 105                 110

Met Glu Leu Ala Glu Ile Glu Ala Ile Gln Glu Ser Leu Gln Pro Ser
                115                 120                 125

Asp Lys Asp Glu Gly Asp His Pro Asn Asn Ser Phe Ser Pro Cys Ser
                130                 135                 140

Ala His Asp Arg Arg Cys Leu Gln Glu Thr Glu Tyr Gly Pro Cys Arg
145                 150                 155                 160

Arg Glu Met Glu Asp Thr Leu Asn His Leu Lys Phe Leu Asn Val Leu
                165                 170                 175

Ser Pro Arg Gly Val His Ile Pro Asn Cys Asp Lys Lys Gly Phe Tyr
                180                 185                 190

Lys Lys Lys Gln Cys Arg Pro Ser Lys Gly Arg Lys Arg Gly Phe Cys
                195                 200                 205

Trp Cys Val Asp Lys Tyr Gly Gln Pro Leu Pro Gly Tyr Thr Thr Lys
```

```
              210                 215                 220
Gly Lys Glu Asp Val His Cys Tyr Ser Met Gln Ser Lys Val Glu Cys
225                 230                 235                 240

Pro Pro Cys Pro Ala Pro Val Ala Gly Pro Ser Val Phe Leu Phe
                245                 250                 255

Pro Pro Lys Pro Lys Asp Gln Leu Met Ile Ser Arg Thr Pro Glu Val
                260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
            290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
                340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Gly Leu His Asn His
            435                 440                 445

Tyr Thr Gln Lys Ser Leu Ser Leu Ser Pro Gly Lys
    450                 455                 460

<210> SEQ ID NO 10
<211> LENGTH: 471
<212> TYPE: PRT
<213> ORGANISM: Artificial Sequence
<220> FEATURE:
<223> OTHER INFORMATION: Synthesized

<400> SEQUENCE: 10

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
                20                  25                  30

Gly Pro Val Val Arg Cys Glu Pro Cys Asp Ala Arg Ala Leu Ala Gln
            35                  40                  45

Cys Ala Pro Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Pro Ala Arg Ala Pro Ala Val Ala Glu Glu Asn Pro Lys Glu Ser Lys
```

```
                115                 120                 125
Pro Gln Ala Gly Thr Ala Arg Pro Gln Asp Val Asn Arg Arg Asp Gln
130                 135                 140

Gln Arg Asn Pro Gly Thr Ser Thr Thr Pro Ser Gln Pro Asn Ser Ala
145                 150                 155                 160

Gly Val Gln Asp Thr Glu Met Gly Pro Cys Arg Arg Glu Met Glu Asp
                165                 170                 175

Thr Leu Asn His Leu Lys Phe Leu Asn Val Leu Ser Pro Arg Gly Val
            180                 185                 190

His Ile Pro Asn Cys Asp Lys Lys Gly Phe Tyr Lys Lys Lys Gln Cys
        195                 200                 205

Arg Pro Ser Lys Gly Arg Lys Arg Gly Phe Cys Trp Cys Val Asp Lys
    210                 215                 220

Tyr Gly Gln Pro Leu Pro Gly Tyr Thr Thr Lys Gly Lys Glu Asp Val
225                 230                 235                 240

His Cys Tyr Ser Met Gln Ser Lys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Gln Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Gly Leu His Asn His Tyr Thr Gln Lys Ser
    450                 455                 460

Leu Ser Leu Ser Pro Gly Lys
465                 470

<210> SEQ ID NO 11
<211> LENGTH: 497
<212> TYPE: PRT
<213> ORGANISM: Artificial Sequence
<220> FEATURE:
<223> OTHER INFORMATION: Synthesized

<400> SEQUENCE: 11

Met Ser Glu Val Pro Val Ala Arg Val Trp Leu Val Leu Leu Leu Leu
```

-continued

```
1               5                   10                  15
Thr Val Gln Val Gly Val Thr Ala Gly Gly Ala Ser Ser Ala Gly Leu
                20                  25                  30
Gly Pro Val Val Arg Cys Glu Pro Cys Asp Ala Arg Ala Leu Ala Gln
                35                  40                  45
Cys Ala Pro Pro Ala Val Cys Ala Glu Leu Val Arg Glu Pro Gly
    50                  55                  60
Cys Gly Cys Cys Leu Thr Cys Ala Leu Ser Glu Gly Gln Pro Cys Gly
65                  70                  75                  80
Ile Tyr Thr Glu Arg Cys Gly Ser Gly Leu Arg Cys Gln Pro Ser Pro
                    85                  90                  95
Asp Glu Ala Arg Pro Leu Gln Ala Leu Leu Asp Gly Arg Gly Leu Cys
                100                 105                 110
Val Asn Ala Ser Ala Val Ser Arg Pro Ala Pro Pro Ala Pro Gly Asn
                115                 120                 125
Ala Ser Glu Ser Glu Glu Asp Arg Ser Ala Gly Ser Val Glu Ser Pro
                130                 135                 140
Ser Val Ser Ser Thr His Arg Val Ser Asp Pro Lys Phe His Pro Lys
145                 150                 155                 160
Gly His Ala Lys Asp Ser Gln Arg Tyr Lys Val Asp Tyr Glu Ser Gln
                    165                 170                 175
Ser Thr Asp Thr Gln Asn Phe Ser Ser Glu Ser Lys Arg Glu Thr Glu
                180                 185                 190
Tyr Gly Pro Cys Arg Arg Glu Met Glu Asp Thr Leu Asn His Leu Lys
                    195                 200                 205
Phe Leu Asn Val Leu Ser Pro Arg Gly Val His Ile Pro Asn Cys Asp
210                 215                 220
Lys Lys Gly Phe Tyr Lys Lys Lys Gln Cys Arg Pro Ser Lys Gly Arg
225                 230                 235                 240
Lys Arg Gly Phe Cys Trp Cys Val Asp Lys Tyr Gly Gln Pro Leu Pro
                    245                 250                 255
Gly Tyr Thr Thr Lys Gly Lys Glu Asp Val His Cys Tyr Ser Met Gln
                    260                 265                 270
Ser Lys Val Glu Cys Pro Pro Cys Pro Ala Pro Val Ala Gly Pro
                275                 280                 285
Ser Val Phe Leu Phe Pro Pro Lys Pro Lys Asp Gln Leu Met Ile Ser
                290                 295                 300
Arg Thr Pro Glu Val Thr Cys Val Val Asp Val Ser His Glu Asp
305                 310                 315                 320
Pro Glu Val Lys Phe Asn Trp Tyr Val Asp Gly Val Glu Val His Asn
                    325                 330                 335
Ala Lys Thr Lys Pro Arg Glu Glu Gln Tyr Asn Ser Thr Tyr Arg Val
                340                 345                 350
Val Ser Val Leu Thr Val Leu His Gln Asp Trp Leu Asn Gly Lys Glu
                355                 360                 365
Tyr Lys Cys Lys Val Ser Asn Lys Gly Leu Pro Ser Ser Ile Glu Lys
                370                 375                 380
Thr Ile Ser Lys Ala Lys Gly Gln Pro Arg Glu Pro Gln Val Tyr Thr
385                 390                 395                 400
Leu Pro Pro Ser Arg Glu Glu Met Thr Lys Asn Gln Val Ser Leu Thr
                    405                 410                 415
Cys Leu Val Lys Gly Phe Tyr Pro Ser Asp Ile Ala Val Glu Trp Glu
                420                 425                 430
```

```
Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
        450                 455                 460

Ser Arg Trp Gln Gln Gly Asn Val Phe Ser Cys Ser Val Met His Glu
465                 470                 475                 480

Gly Leu His Asn His Tyr Thr Gln Lys Ser Leu Ser Leu Ser Pro Gly
                485                 490                 495

Lys

<210> SEQ ID NO 12
<211> LENGTH: 491
<212> TYPE: PRT
<213> ORGANISM: Artificial Sequence
<220> FEATURE:
<223> OTHER INFORMATION: Synthesized

<400> SEQUENCE: 12

Met Ser Glu Val Pro Val Ala Arg Val Trp Leu Val Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Arg Pro Ala Pro Ala Pro Gly Asn
        115                 120                 125

Ala Ser Glu Ser Glu Glu Asp Arg Ser Ala Gly Ser Val Glu Ser Pro
    130                 135                 140

Ser Val Ser Ser Thr His Arg Val Ser Asp Pro Lys Phe His Pro Lys
145                 150                 155                 160

Gly His Ala Lys Val Asp Tyr Glu Ser Gln Ser Thr Asp Thr Gln Asn
                165                 170                 175

Phe Ser Ser Glu Ser Lys Arg Glu Thr Glu Tyr Gly Pro Cys Arg Arg
            180                 185                 190

Glu Met Glu Asp Thr Leu Asn His Leu Lys Phe Leu Asn Val Leu Ser
        195                 200                 205

Pro Arg Gly Val His Ile Pro Asn Cys Asp Lys Lys Gly Phe Tyr Lys
    210                 215                 220

Lys Lys Gln Cys Arg Pro Ser Lys Gly Arg Lys Arg Gly Phe Cys Trp
225                 230                 235                 240

Cys Val Asp Lys Tyr Gly Gln Pro Leu Pro Gly Tyr Thr Thr Lys Gly
                245                 250                 255

Lys Glu Asp Val His Cys Tyr Ser Met Gln Ser Lys Val Glu Cys Pro
            260                 265                 270

Pro Cys Pro Ala Pro Pro Val Ala Gly Pro Ser Val Phe Leu Phe Pro
        275                 280                 285
```

```
Pro Lys Pro Lys Asp Gln Leu Met Ile Ser Arg Thr Pro Glu Val Thr
    290                 295                 300

Cys Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
                340                 345                 350

Leu His Gln Asp Trp Leu Asn Gly Lys Glu Tyr Lys Cys Lys Val Ser
                355                 360                 365

Asn Lys Gly Leu Pro Ser Ser Ile Glu Lys Thr Ile Ser Lys Ala Lys
370                 375                 380

Gly Gln Pro Arg Glu Pro Gln Val Tyr Thr Leu Pro Pro Ser Arg Glu
385                 390                 395                 400

Glu Met Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
                420                 425                 430

Asn Asn Tyr Lys Thr Thr Pro Pro Val Leu Asp Ser Asp Gly Ser Phe
                435                 440                 445

Phe Leu Tyr Ser Lys Leu Thr Val Asp Lys Ser Arg Trp Gln Gln Gly
450                 455                 460

Asn Val Phe Ser Cys Ser Val Met His Glu Gly Leu His Asn His Tyr
465                 470                 475                 480

Thr Gln Lys Ser Leu Ser Leu Ser Pro Gly Lys
                485                 490

<210> SEQ ID NO 13
<211> LENGTH: 18
<212> TYPE: PRT
<213> ORGANISM: Artificial Sequence
<220> FEATURE:
<223> OTHER INFORMATION: Synthesized

<400> SEQUENCE: 13

Ala Pro Pro Ala Pro Gly Asn Ala Ser Glu Ser Glu Glu Asp Arg Ser
1               5                   10                  15

Ala Gly

<210> SEQ ID NO 14
<211> LENGTH: 685
<212> TYPE: PRT
<213> ORGANISM: Artificial Sequence
<220> FEATURE:
<223> OTHER INFORMATION: Synthesized

<400> SEQUENCE: 14

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
                20                  25                  30

Gly Pro Val Val Arg Cys Glu Pro Cys Asp Ala Arg Ala Leu Ala Gln
                35                  40                  45

Cys Ala Pro Pro Pro Ala Val Cys Ala Glu Leu Val Arg Glu Pro Gly
            50                  55                  60

Cys Gly Cys Cys Leu Thr Cys Ala Leu Ser Glu Gly Gln Pro Cys Gly
65              70                  75                  80
```

-continued

```
Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Lys Gly His Ala Lys Asp Ser Gln Arg
        115                 120                 125

Tyr Lys Val Asp Tyr Glu Ser Gln Ser Thr Asp Thr Gln Asn Phe Ser
    130                 135                 140

Ser Glu Ser Lys Arg Glu Thr Glu Tyr Gly Pro Cys Arg Arg Glu Met
145                 150                 155                 160

Glu Asp Thr Leu Asn His Leu Lys Phe Leu Asn Val Leu Ser Pro Arg
                165                 170                 175

Gly Val His Ile Pro Asn Cys Asp Lys Lys Gly Phe Tyr Lys Lys Lys
            180                 185                 190

Gln Cys Arg Pro Ser Lys Gly Arg Lys Arg Gly Phe Cys Trp Cys Val
        195                 200                 205

Asp Lys Tyr Gly Gln Pro Leu Pro Gly Tyr Thr Thr Lys Gly Lys Glu
    210                 215                 220

Asp Val His Cys Tyr Ser Met Gln Ser Lys Ala Pro Ala Pro Gly
225                 230                 235                 240

Asn Ala Ser Glu Ser Glu Asp Arg Ser Ala Gly Ile Tyr Ile Phe
                245                 250                 255

Ile Ser Asp Thr Gly Arg Pro Phe Val Glu Met Tyr Ser Glu Ile Pro
                260                 265                 270

Glu Ile Ile His Met Thr Glu Gly Arg Glu Leu Val Ile Pro Cys Arg
            275                 280                 285

Val Thr Ser Pro Asn Ile Thr Val Thr Leu Lys Lys Phe Pro Leu Asp
        290                 295                 300

Thr Leu Ile Pro Asp Gly Lys Arg Ile Ile Trp Asp Ser Arg Lys Gly
305                 310                 315                 320

Phe Ile Ile Ser Asn Ala Thr Tyr Lys Glu Ile Gly Leu Leu Thr Cys
                325                 330                 335

Glu Ala Thr Val Asn Gly His Leu Tyr Lys Thr Asn Tyr Leu Thr His
            340                 345                 350

Arg Gln Gly Tyr Arg Ile Tyr Asp Val Val Leu Ser Pro Ser His Gly
        355                 360                 365

Ile Glu Leu Ser Val Gly Glu Lys Leu Val Leu Asn Cys Thr Ala Arg
    370                 375                 380

Thr Glu Leu Asn Val Gly Ile Asp Phe Asn Trp Glu Tyr Pro Ser Ser
385                 390                 395                 400

Lys His Gln His Lys Lys Leu Val Asn Arg Asp Leu Lys Thr Gln Ser
                405                 410                 415

Gly Ser Glu Met Lys Lys Phe Leu Ser Thr Leu Thr Ile Asp Gly Val
            420                 425                 430

Thr Arg Ser Asp Gln Gly Leu Tyr Thr Cys Ala Ala Ser Ser Gly Leu
        435                 440                 445

Met Thr Lys Lys Asn Ser Thr Phe Val Arg Val His Glu Lys Val Glu
    450                 455                 460

Cys Pro Pro Cys Pro Ala Pro Val Ala Gly Pro Ser Val Phe Leu
465                 470                 475                 480

Phe Pro Pro Lys Pro Lys Asp Gln Leu Met Ile Ser Arg Thr Pro Glu
                485                 490                 495

Val Thr Cys Val Val Val Asp Val Ser His Glu Asp Pro Glu Val Lys
```

```
                    500                 505                 510
        Phe Asn Trp Tyr Val Asp Gly Val Glu Val His Asn Ala Lys Thr Lys
                515                 520                 525

Pro Arg Glu Glu Gln Tyr Asn Ser Thr Tyr Arg Val Val Ser Val Leu
                530                 535                 540

Thr Val Leu His Gln Asp Trp Leu Asn Gly Lys Glu Tyr Lys Cys Lys
        545                 550                 555                 560

Val Ser Asn Lys Gly Leu Pro Ser Ser Ile Glu Lys Thr Ile Ser Lys
                        565                 570                 575

Ala Lys Gly Gln Pro Arg Glu Pro Gln Val Tyr Thr Leu Pro Pro Ser
                    580                 585                 590

Arg Glu Glu Met Thr Lys Asn Gln Val Ser Leu Thr Cys Leu Val Lys
                    595                 600                 605

Gly Phe Tyr Pro Ser Asp Ile Ala Val Glu Trp Glu Ser Asn Gly Gln
                610                 615                 620

Pro Glu Asn Asn Tyr Lys Thr Thr Pro Pro Val Leu Asp Ser Asp Gly
        625                 630                 635                 640

Ser Phe Phe Leu Tyr Ser Lys Leu Thr Val Asp Lys Ser Arg Trp Gln
                        645                 650                 655

Gln Gly Asn Val Phe Ser Cys Ser Val Met His Glu Gly Leu His Asn
                    660                 665                 670

His Tyr Thr Gln Lys Ser Leu Ser Leu Ser Pro Gly Lys
                    675                 680                 685

<210> SEQ ID NO 15
<211> LENGTH: 688
<212> TYPE: PRT
<213> ORGANISM: Artificial Sequence
<220> FEATURE:
<223> OTHER INFORMATION: Synthesized

<400> SEQUENCE: 15

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Met Glu Leu Ala Glu Ile Glu Ala Ile Gln Glu Ser Leu Gln Pro Ser
        115                 120                 125

Asp Lys Asp Glu Gly Asp His Pro Asn Asn Ser Phe Ser Pro Cys Ser
    130                 135                 140

Ala His Asp Arg Arg Cys Leu Gln Glu Thr Glu Tyr Gly Pro Cys Arg
145                 150                 155                 160

Arg Glu Met Glu Asp Thr Leu Asn His Leu Lys Phe Leu Asn Val Leu
                165                 170                 175

Ser Pro Arg Gly Val His Ile Pro Asn Cys Asp Lys Lys Gly Phe Tyr
```

-continued

```
            180                 185                 190
Lys Lys Lys Gln Cys Arg Pro Ser Lys Gly Arg Lys Arg Gly Phe Cys
            195                 200                 205
Trp Cys Val Asp Lys Tyr Gly Gln Pro Leu Pro Gly Tyr Thr Thr Lys
210                 215                 220
Gly Lys Glu Asp Val His Cys Tyr Ser Met Gln Ser Lys Ala Pro Pro
225                 230                 235                 240
Ala Pro Gly Asn Ala Ser Glu Ser Glu Asp Arg Ser Ala Gly Ile
            245                 250                 255
Tyr Ile Phe Ile Ser Asp Thr Gly Arg Pro Phe Val Glu Met Tyr Ser
            260                 265                 270
Glu Ile Pro Glu Ile Ile His Met Thr Glu Gly Arg Glu Leu Val Ile
            275                 280                 285
Pro Cys Arg Val Thr Ser Pro Asn Ile Thr Val Thr Leu Lys Lys Phe
            290                 295                 300
Pro Leu Asp Thr Leu Ile Pro Asp Gly Lys Arg Ile Ile Trp Asp Ser
305                 310                 315                 320
Arg Lys Gly Phe Ile Ile Ser Asn Ala Thr Tyr Lys Glu Ile Gly Leu
            325                 330                 335
Leu Thr Cys Glu Ala Thr Val Asn Gly His Leu Tyr Lys Thr Asn Tyr
            340                 345                 350
Leu Thr His Arg Gln Gly Tyr Arg Ile Tyr Asp Val Val Leu Ser Pro
            355                 360                 365
Ser His Gly Ile Glu Leu Ser Val Gly Glu Lys Leu Val Leu Asn Cys
            370                 375                 380
Thr Ala Arg Thr Glu Leu Asn Val Gly Ile Asp Phe Asn Trp Glu Tyr
385                 390                 395                 400
Pro Ser Ser Lys His Gln His Lys Lys Leu Val Asn Arg Asp Leu Lys
            405                 410                 415
Thr Gln Ser Gly Ser Glu Met Lys Lys Phe Leu Ser Thr Leu Thr Ile
            420                 425                 430
Asp Gly Val Thr Arg Ser Asp Gln Gly Leu Tyr Thr Cys Ala Ala Ser
            435                 440                 445
Ser Gly Leu Met Thr Lys Lys Asn Ser Thr Phe Val Arg Val His Glu
            450                 455                 460
Lys Val Glu Cys Pro Pro Cys Pro Ala Pro Val Ala Gly Pro Ser
465                 470                 475                 480
Val Phe Leu Phe Pro Pro Lys Pro Lys Asp Gln Leu Met Ile Ser Arg
            485                 490                 495
Thr Pro Glu Val Thr Cys Val Val Val Asp Val Ser His Glu Asp Pro
            500                 505                 510
Glu Val Lys Phe Asn Trp Tyr Val Asp Gly Val Glu Val His Asn Ala
            515                 520                 525
Lys Thr Lys Pro Arg Glu Glu Gln Tyr Asn Ser Thr Tyr Arg Val Val
            530                 535                 540
Ser Val Leu Thr Val Leu His Gln Asp Trp Leu Asn Gly Lys Glu Tyr
545                 550                 555                 560
Lys Cys Lys Val Ser Asn Lys Gly Leu Pro Ser Ser Ile Glu Lys Thr
            565                 570                 575
Ile Ser Lys Ala Lys Gly Gln Pro Arg Glu Pro Gln Val Tyr Thr Leu
            580                 585                 590
Pro Pro Ser Arg Glu Glu Met Thr Lys Asn Gln Val Ser Leu Thr Cys
            595                 600                 605
```

```
Leu Val Lys Gly Phe Tyr Pro Ser Asp Ile Ala Val Glu Trp Glu Ser
        610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Gly
                660                 665                 670

Leu His Asn His Tyr Thr Gln Lys Ser Leu Ser Leu Ser Pro Gly Lys
            675                 680                 685

<210> SEQ ID NO 16
<211> LENGTH: 736
<212> TYPE: PRT
<213> ORGANISM: Artificial Sequence
<220> FEATURE:
<223> OTHER INFORMATION: Synthesized

<400> SEQUENCE: 16

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Pro Ala Arg Ala Pro Ala Val Ala Glu Glu Asn Pro Lys Glu Ser Lys
        115                 120                 125

Pro Gln Ala Gly Thr Ala Arg Pro Gln Asp Val Asn Arg Arg Asp Gln
    130                 135                 140

Gln Arg Asn Pro Gly Thr Ser Thr Thr Pro Ser Gln Pro Asn Ser Ala
145                 150                 155                 160

Gly Val Gln Asp Thr Glu Met Gly Pro Cys Arg Arg Glu Met Glu Asp
                165                 170                 175

Thr Leu Asn His Leu Lys Phe Leu Asn Val Leu Ser Pro Arg Gly Val
            180                 185                 190

His Ile Pro Asn Cys Asp Lys Lys Gly Phe Tyr Lys Lys Lys Gln Cys
        195                 200                 205

Arg Pro Ser Lys Gly Arg Lys Arg Gly Phe Cys Trp Cys Val Asp Lys
    210                 215                 220

Tyr Gly Gln Pro Leu Pro Gly Tyr Thr Thr Lys Gly Lys Glu Asp Val
225                 230                 235                 240

His Cys Tyr Ser Met Gln Ser Lys Pro Ala Arg Ala Pro Ala Val Ala
                245                 250                 255

Glu Glu Asn Pro Lys Glu Ser Lys Pro Gln Ala Gly Thr Ala Arg Pro
            260                 265                 270

Gln Asp Val Asn Arg Arg Asp Gln Gln Arg Asn Pro Gly Thr Ser Thr
        275                 280                 285
```

-continued

```
Thr Pro Ser Gln Pro Asn Ser Ala Gly Val Gln Asp Thr Glu Met Ile
    290                 295                 300
Tyr Ile Phe Ile Ser Asp Thr Gly Arg Pro Phe Val Glu Met Tyr Ser
305                 310                 315                 320
Glu Ile Pro Glu Ile Ile His Met Thr Glu Gly Arg Glu Leu Val Ile
                325                 330                 335
Pro Cys Arg Val Thr Ser Pro Asn Ile Thr Val Thr Leu Lys Lys Phe
            340                 345                 350
Pro Leu Asp Thr Leu Ile Pro Asp Gly Lys Arg Ile Ile Trp Asp Ser
        355                 360                 365
Arg Lys Gly Phe Ile Ile Ser Asn Ala Thr Tyr Lys Glu Ile Gly Leu
    370                 375                 380
Leu Thr Cys Glu Ala Thr Val Asn Gly His Leu Tyr Lys Thr Asn Tyr
385                 390                 395                 400
Leu Thr His Arg Gln Gly Tyr Arg Ile Tyr Asp Val Val Leu Ser Pro
                405                 410                 415
Ser His Gly Ile Glu Leu Ser Val Gly Glu Lys Leu Val Leu Asn Cys
            420                 425                 430
Thr Ala Arg Thr Glu Leu Asn Val Gly Ile Asp Phe Asn Trp Glu Tyr
        435                 440                 445
Pro Ser Ser Lys His Gln His Lys Lys Leu Val Asn Arg Asp Leu Lys
    450                 455                 460
Thr Gln Ser Gly Ser Glu Met Lys Lys Phe Leu Ser Thr Leu Thr Ile
465                 470                 475                 480
Asp Gly Val Thr Arg Ser Asp Gln Gly Leu Tyr Thr Cys Ala Ala Ser
                485                 490                 495
Ser Gly Leu Met Thr Lys Lys Asn Ser Thr Phe Val Arg Val His Glu
            500                 505                 510
Lys Val Glu Cys Pro Pro Cys Pro Ala Pro Pro Val Ala Gly Pro Ser
        515                 520                 525
Val Phe Leu Phe Pro Pro Lys Pro Lys Asp Gln Leu Met Ile Ser Arg
    530                 535                 540
Thr Pro Glu Val Thr Cys Val Val Val Asp Val Ser His Glu Asp Pro
545                 550                 555                 560
Glu Val Lys Phe Asn Trp Tyr Val Asp Gly Val Glu Val His Asn Ala
                565                 570                 575
Lys Thr Lys Pro Arg Glu Glu Gln Tyr Asn Ser Thr Tyr Arg Val Val
            580                 585                 590
Ser Val Leu Thr Val Leu His Gln Asp Trp Leu Asn Gly Lys Glu Tyr
        595                 600                 605
Lys Cys Lys Val Ser Asn Lys Gly Leu Pro Ser Ser Ile Glu Lys Thr
    610                 615                 620
Ile Ser Lys Ala Lys Gly Gln Pro Arg Glu Pro Gln Val Tyr Thr Leu
625                 630                 635                 640
Pro Pro Ser Arg Glu Glu Met Thr Lys Asn Gln Val Ser Leu Thr Cys
                645                 650                 655
Leu Val Lys Gly Phe Tyr Pro Ser Asp Ile Ala Val Glu Trp Glu Ser
            660                 665                 670
Asn Gly Gln Pro Glu Asn Asn Tyr Lys Thr Thr Pro Pro Val Leu Asp
        675                 680                 685
Ser Asp Gly Ser Phe Phe Leu Tyr Ser Lys Leu Thr Val Asp Lys Ser
    690                 695                 700
```

```
Arg Trp Gln Gln Gly Asn Val Phe Ser Cys Ser Val Met His Glu Gly
705                 710                 715                 720

Leu His Asn His Tyr Thr Gln Lys Ser Leu Ser Leu Ser Pro Gly Lys
            725                 730                 735

<210> SEQ ID NO 17
<211> LENGTH: 731
<212> TYPE: PRT
<213> ORGANISM: Artificial Sequence
<220> FEATURE:
<223> OTHER INFORMATION: Synthesized

<400> SEQUENCE: 17

Met Ser Glu Val Pro Val Ala Arg Val Trp Leu Val Leu Leu Leu Leu
1               5                   10                  15

Thr Val Gln Val Gly Val Thr Ala Gly His His His His His His Gly
            20                  25                  30

Ala Ser Ser Ala Gly Leu Gly Pro Val Val Arg Cys Glu Pro Cys Asp
        35                  40                  45

Ala Arg Ala Leu Ala Gln Cys Ala Pro Pro Pro Ala Val Cys Ala Glu
    50                  55                  60

Leu Val Arg Glu Pro Gly Cys Gly Cys Cys Leu Thr Cys Ala Leu Ser
65                  70                  75                  80

Glu Gly Gln Pro Cys Gly Ile Tyr Thr Glu Arg Cys Gly Ser Gly Leu
                85                  90                  95

Arg Cys Gln Pro Ser Pro Asp Glu Ala Arg Pro Leu Gln Ala Leu Leu
            100                 105                 110

Asp Gly Arg Gly Leu Cys Val Asn Ala Ser Ala Val Ser Arg Pro Ala
        115                 120                 125

Pro Pro Ala Pro Gly Asn Ala Ser Glu Ser Glu Glu Asp Arg Ser Ala
    130                 135                 140

Gly Ser Val Glu Ser Pro Ser Val Ser Ser Thr His Arg Val Ser Asp
145                 150                 155                 160

Pro Lys Phe His Pro Lys His Ala Lys Asp Ser Gln Arg Tyr Lys
                165                 170                 175

Val Asp Tyr Glu Ser Gln Ser Thr Asp Thr Gln Asn Phe Ser Ser Glu
            180                 185                 190

Ser Lys Arg Glu Thr Glu Tyr Gly Pro Cys Arg Arg Glu Met Glu Asp
        195                 200                 205

Thr Leu Asn His Leu Lys Phe Leu Asn Val Leu Ser Pro Arg Gly Val
    210                 215                 220

His Ile Pro Asn Cys Asp Lys Lys Gly Phe Tyr Lys Lys Lys Gln Cys
225                 230                 235                 240

Arg Pro Ser Lys Gly Arg Lys Arg Gly Phe Cys Trp Cys Val Asp Lys
                245                 250                 255

Tyr Gly Gln Pro Leu Pro Gly Tyr Thr Thr Lys Gly Lys Glu Asp Val
            260                 265                 270

His Cys Tyr Ser Met Gln Ser Lys Ala Pro Ala Pro Gly Asn Ala
        275                 280                 285

Ser Glu Ser Glu Glu Asp Arg Ser Ala Gly Ile Tyr Ile Phe Ile Ser
    290                 295                 300

Asp Thr Gly Arg Pro Phe Val Glu Met Tyr Ser Glu Ile Pro Glu Ile
305                 310                 315                 320

Ile His Met Thr Glu Gly Arg Glu Leu Val Ile Pro Cys Arg Val Thr
                325                 330                 335
```

```
Ser Pro Asn Ile Thr Val Thr Leu Lys Lys Phe Pro Leu Asp Thr Leu
                340                 345                 350

Ile Pro Asp Gly Lys Arg Ile Ile Trp Asp Ser Arg Lys Gly Phe Ile
            355                 360                 365

Ile Ser Asn Ala Thr Tyr Lys Glu Ile Gly Leu Leu Thr Cys Glu Ala
        370                 375                 380

Thr Val Asn Gly His Leu Tyr Lys Thr Asn Tyr Leu Thr His Arg Gln
385                 390                 395                 400

Gly Tyr Arg Ile Tyr Asp Val Val Leu Ser Pro Ser His Gly Ile Glu
                405                 410                 415

Leu Ser Val Gly Glu Lys Leu Val Leu Asn Cys Thr Ala Arg Thr Glu
            420                 425                 430

Leu Asn Val Gly Ile Asp Phe Asn Trp Glu Tyr Pro Ser Ser Lys His
        435                 440                 445

Gln His Lys Lys Leu Val Asn Arg Asp Leu Lys Thr Gln Ser Gly Ser
    450                 455                 460

Glu Met Lys Lys Phe Leu Ser Thr Leu Thr Ile Asp Gly Val Thr Arg
465                 470                 475                 480

Ser Asp Gln Gly Leu Tyr Thr Cys Ala Ala Ser Ser Gly Leu Met Thr
                485                 490                 495

Lys Lys Asn Ser Thr Phe Val Arg Val His Glu Lys Val Glu Cys Pro
            500                 505                 510

Pro Cys Pro Ala Pro Pro Val Ala Gly Pro Ser Val Phe Leu Phe Pro
        515                 520                 525

Pro Lys Pro Lys Asp Gln Leu Met Ile Ser Arg Thr Pro Glu Val Thr
    530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Asn Ser Thr Tyr Arg Val Val Ser Val Leu Thr Val
            580                 585                 590

Leu His Gln Asp Trp Leu Asn Gly Lys Glu Tyr Lys Cys Lys Val Ser
        595                 600                 605

Asn Lys Gly Leu Pro Ser Ser Ile Glu Lys Thr Ile Ser Lys Ala Lys
    610                 615                 620

Gly Gln Pro Arg Glu Pro Gln Val Tyr Thr Leu Pro Pro Ser Arg Glu
625                 630                 635                 640

Glu Met Thr Lys Asn Gln Val Ser Leu Thr Cys Leu Val Lys Gly Phe
                645                 650                 655

Tyr Pro Ser Asp Ile Ala Val Glu Trp Glu Ser Asn Gly Gln Pro Glu
            660                 665                 670

Asn Asn Tyr Lys Thr Thr Pro Pro Val Leu Asp Ser Asp Gly Ser Phe
        675                 680                 685

Phe Leu Tyr Ser Lys Leu Thr Val Asp Lys Ser Arg Trp Gln Gln Gly
    690                 695                 700

Asn Val Phe Ser Cys Ser Val Met His Glu Gly Leu His Asn His Tyr
705                 710                 715                 720

Thr Gln Lys Ser Leu Ser Leu Ser Pro Gly Lys
                725                 730

<210> SEQ ID NO 18
<211> LENGTH: 725
<212> TYPE: PRT
```

<213> ORGANISM: Artificial Sequence
<220> FEATURE:
<223> OTHER INFORMATION: Synthesized

<400> SEQUENCE: 18

```
Met Ser Glu Val Pro Val Ala Arg Val Trp Leu Val Leu Leu Leu Leu
1               5                   10                  15

Thr Val Gln Val Gly Val Thr Ala Gly His His His His His His Gly
                20                  25                  30

Ala Ser Ala Gly Leu Gly Pro Val Val Arg Cys Glu Pro Cys Asp
            35                  40                  45

Ala Arg Ala Leu Ala Gln Cys Ala Pro Pro Ala Val Cys Ala Glu
50                  55                  60

Leu Val Arg Glu Pro Gly Cys Gly Cys Cys Leu Thr Cys Ala Leu Ser
65                  70                  75                  80

Glu Gly Gln Pro Cys Gly Ile Tyr Thr Glu Arg Cys Gly Ser Gly Leu
                85                  90                  95

Arg Cys Gln Pro Ser Pro Asp Glu Ala Arg Pro Leu Gln Ala Leu Leu
                100                 105                 110

Asp Gly Arg Gly Leu Cys Val Asn Ala Ser Ala Val Ser Arg Pro Ala
            115                 120                 125

Pro Pro Ala Pro Gly Asn Ala Ser Glu Ser Glu Glu Asp Arg Ser Ala
130                 135                 140

Gly Ser Val Glu Ser Pro Ser Val Ser Ser Thr His Arg Val Ser Asp
145                 150                 155                 160

Pro Lys Phe His Pro Lys Gly His Ala Lys Val Asp Tyr Glu Ser Gln
                165                 170                 175

Ser Thr Asp Thr Gln Asn Phe Ser Ser Glu Ser Lys Arg Glu Thr Glu
            180                 185                 190

Tyr Gly Pro Cys Arg Arg Glu Met Glu Asp Thr Leu Asn His Leu Lys
        195                 200                 205

Phe Leu Asn Val Leu Ser Pro Arg Gly Val His Ile Pro Asn Cys Asp
    210                 215                 220

Lys Lys Gly Phe Tyr Lys Lys Lys Gln Cys Arg Pro Ser Lys Gly Arg
225                 230                 235                 240

Lys Arg Gly Phe Cys Trp Cys Val Asp Lys Tyr Gly Gln Pro Leu Pro
                245                 250                 255

Gly Tyr Thr Thr Lys Gly Lys Glu Asp Val His Cys Tyr Ser Met Gln
            260                 265                 270

Ser Lys Ala Pro Pro Ala Pro Gly Asn Ala Ser Glu Ser Glu Glu Asp
        275                 280                 285

Arg Ser Ala Gly Ile Tyr Ile Phe Ile Ser Asp Thr Gly Arg Pro Phe
    290                 295                 300

Val Glu Met Tyr Ser Glu Ile Pro Glu Ile Ile His Met Thr Glu Gly
305                 310                 315                 320

Arg Glu Leu Val Ile Pro Cys Arg Val Thr Ser Pro Asn Ile Thr Val
                325                 330                 335

Thr Leu Lys Lys Phe Pro Leu Asp Thr Leu Ile Pro Asp Gly Lys Arg
            340                 345                 350

Ile Ile Trp Asp Ser Arg Lys Gly Phe Ile Ile Ser Asn Ala Thr Tyr
        355                 360                 365

Lys Glu Ile Gly Leu Leu Thr Cys Glu Ala Thr Val Asn Gly His Leu
    370                 375                 380

Tyr Lys Thr Asn Tyr Leu Thr His Arg Gln Gly Tyr Arg Ile Tyr Asp
```

```
                385                 390                 395                 400
    Val Val Leu Ser Pro Ser His Gly Ile Glu Leu Ser Val Gly Glu Lys
                    405                 410                 415

Leu Val Leu Asn Cys Thr Ala Arg Thr Glu Leu Asn Val Gly Ile Asp
                420                 425                 430

Phe Asn Trp Glu Tyr Pro Ser Lys His Gln His Lys Lys Leu Val
                435                 440                 445

Asn Arg Asp Leu Lys Thr Gln Ser Gly Ser Glu Met Lys Lys Phe Leu
                450                 455                 460

Ser Thr Leu Thr Ile Asp Gly Val Thr Arg Ser Asp Gln Gly Leu Tyr
    465                 470                 475                 480

Thr Cys Ala Ala Ser Ser Gly Leu Met Thr Lys Lys Asn Ser Thr Phe
                    485                 490                 495

Val Arg Val His Glu Lys Val Glu Cys Pro Cys Pro Ala Pro Pro
                500                 505                 510

Val Ala Gly Pro Ser Val Phe Leu Phe Pro Pro Lys Pro Lys Asp Gln
                515                 520                 525

Leu Met Ile Ser Arg Thr Pro Glu Val Thr Cys Val Val Asp Val
                530                 535                 540

Ser His Glu Asp Pro Glu Val Lys Phe Asn Trp Tyr Val Asp Gly Val
    545                 550                 555                 560

Glu Val His Asn Ala Lys Thr Lys Pro Arg Glu Glu Gln Tyr Asn Ser
                    565                 570                 575

Thr Tyr Arg Val Val Ser Val Leu Thr Val Leu His Gln Asp Trp Leu
                580                 585                 590

Asn Gly Lys Glu Tyr Lys Cys Lys Val Ser Asn Lys Gly Leu Pro Ser
                595                 600                 605

Ser Ile Glu Lys Thr Ile Ser Lys Ala Lys Gly Gln Pro Arg Glu Pro
                610                 615                 620

Gln Val Tyr Thr Leu Pro Pro Ser Arg Glu Glu Met Thr Lys Asn Gln
    625                 630                 635                 640

Val Ser Leu Thr Cys Leu Val Lys Gly Phe Tyr Pro Ser Asp Ile Ala
                    645                 650                 655

Val Glu Trp Glu Ser Asn Gly Gln Pro Glu Asn Asn Tyr Lys Thr Thr
                660                 665                 670

Pro Pro Val Leu Asp Ser Asp Gly Ser Phe Phe Leu Tyr Ser Lys Leu
                675                 680                 685

Thr Val Asp Lys Ser Arg Trp Gln Gln Gly Asn Val Phe Ser Cys Ser
                690                 695                 700

Val Met His Glu Gly Leu His Asn His Tyr Thr Gln Lys Ser Leu Ser
    705                 710                 715                 720

Leu Ser Pro Gly Lys
                725

<210> SEQ ID NO 19
<211> LENGTH: 683
<212> TYPE: PRT
<213> ORGANISM: Artificial Sequence
<220> FEATURE:
<223> OTHER INFORMATION: Synthesized

<400> SEQUENCE: 19

Met Ser Glu Val Pro Val Ala Arg Val Trp Leu Val Leu Leu Leu
1               5                   10                  15

Thr Val Gln Val Gly Val Thr Ala Gly Gly Ala Ser Ser Ala Gly Leu
```

```
                20                  25                  30
Gly Pro Val Val Arg Cys Glu Pro Cys Asp Ala Arg Ala Leu Ala Gln
            35                  40                  45

Cys Ala Pro Pro Ala Val Cys Ala Glu Leu Val Arg Glu Pro Gly
50                  55                  60

Cys Gly Cys Cys Leu Thr Cys Ala Leu Ser Glu Gly Gln Pro Cys
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Lys Gly His Ala Lys Asp Ser Gln Arg
            115                 120                 125

Tyr Lys Val Asp Tyr Glu Ser Gln Ser Thr Asp Thr Gln Asn Phe Ser
            130                 135                 140

Ser Glu Ser Lys Arg Glu Thr Glu Tyr Gly Pro Cys Arg Arg Glu Met
145                 150                 155                 160

Glu Asp Thr Leu Asn His Leu Lys Phe Leu Asn Val Leu Ser Pro Arg
                165                 170                 175

Gly Val His Ile Pro Asn Cys Asp Lys Lys Gly Phe Tyr Lys Lys Lys
            180                 185                 190

Gln Cys Arg Pro Ser Lys Gly Arg Lys Arg Gly Phe Cys Trp Cys Val
            195                 200                 205

Asp Lys Tyr Gly Gln Pro Leu Pro Gly Tyr Thr Thr Lys Gly Lys Glu
            210                 215                 220

Asp Val His Cys Tyr Ser Met Gln Ser Lys Gly Gly Gly Ser Gly
225                 230                 235                 240

Gly Gly Gly Ser Gly Gly Gly Ser Gly Ile Tyr Ile Phe Ile Ser
                245                 250                 255

Asp Thr Gly Arg Pro Phe Val Glu Met Tyr Ser Glu Ile Pro Glu Ile
            260                 265                 270

Ile His Met Thr Glu Gly Arg Glu Leu Val Ile Pro Cys Arg Val Thr
            275                 280                 285

Ser Pro Asn Ile Thr Val Thr Leu Lys Lys Phe Pro Leu Asp Thr Leu
            290                 295                 300

Ile Pro Asp Gly Lys Arg Ile Ile Trp Asp Ser Arg Lys Gly Phe Ile
305                 310                 315                 320

Ile Ser Asn Ala Thr Tyr Lys Glu Ile Gly Leu Leu Thr Cys Glu Ala
                325                 330                 335

Thr Val Asn Gly His Leu Tyr Lys Thr Asn Tyr Leu Thr His Arg Gln
            340                 345                 350

Gly Tyr Arg Ile Tyr Asp Val Leu Ser Pro Ser His Gly Ile Glu
            355                 360                 365

Leu Ser Val Gly Glu Lys Leu Val Leu Asn Cys Thr Ala Arg Thr Glu
            370                 375                 380

Leu Asn Val Gly Ile Asp Phe Asn Trp Glu Tyr Pro Ser Ser Lys His
385                 390                 395                 400

Gln His Lys Lys Leu Val Asn Arg Asp Leu Lys Thr Gln Ser Gly Ser
                405                 410                 415

Glu Met Lys Lys Phe Leu Ser Thr Leu Thr Ile Asp Gly Val Thr Arg
            420                 425                 430

Ser Asp Gln Gly Leu Tyr Thr Cys Ala Ala Ser Ser Gly Leu Met Thr
            435                 440                 445
```

Lys Lys Asn Ser Thr Phe Val Arg Val His Glu Lys Val Glu Cys Pro
450                 455                 460

Pro Cys Pro Ala Pro Pro Val Ala Gly Pro Ser Val Phe Leu Phe Pro
465                 470                 475                 480

Pro Lys Pro Lys Asp Gln Leu Met Ile Ser Arg Thr Pro Glu Val Thr
        485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Gly Leu Pro Ser Ser Ile Glu Lys Thr Ile Ser Lys Ala Lys
                565                 570                 575

Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Gly Leu His Asn His Tyr
            660                 665                 670

Thr Gln Lys Ser Leu Ser Leu Ser Pro Gly Lys
        675                 680

<210> SEQ ID NO 20
<211> LENGTH: 902
<212> TYPE: PRT
<213> ORGANISM: Artificial Sequence
<220> FEATURE:
<223> OTHER INFORMATION: Synthesized

<400> SEQUENCE: 20

Met Ser Glu Val Pro Val Ala Arg Val Trp Leu Val Leu Leu Leu Leu
1               5                   10                  15

Thr Val Gln Val Gly Val Thr Ala Gly Val Gln Pro Ser Asp Ser Gln
            20                  25                  30

Ser Val Cys Ala Gly Thr Glu Asn Lys Leu Ser Ser Leu Ser Asp Leu
        35                  40                  45

Glu Gln Gln Tyr Arg Ala Leu Arg Lys Tyr Tyr Glu Asn Cys Glu Val
    50                  55                  60

Val Met Gly Asn Leu Glu Ile Thr Ser Ile Glu His Asn Arg Asp Leu
65                  70                  75                  80

Ser Phe Leu Arg Ser Val Arg Glu Val Thr Gly Tyr Val Leu Val Ala
                85                  90                  95

Leu Asn Gln Phe Arg Tyr Leu Pro Leu Glu Asn Leu Arg Ile Ile Arg
            100                 105                 110

Gly Thr Lys Leu Tyr Glu Asp Arg Tyr Ala Leu Ala Ile Phe Leu Asn
        115                 120                 125

-continued

```
Tyr Arg Lys Asp Gly Asn Phe Gly Leu Gln Glu Leu Gly Leu Lys Asn
            130                 135                 140

Leu Thr Glu Ile Leu Asn Gly Gly Val Tyr Val Asp Gln Asn Lys Phe
145                 150                 155                 160

Leu Cys Tyr Ala Asp Thr Ile His Trp Gln Asp Ile Val Arg Asn Pro
                165                 170                 175

Trp Pro Ser Asn Leu Thr Leu Val Ser Thr Asn Gly Ser Ser Gly Cys
                180                 185                 190

Gly Arg Cys His Lys Ser Cys Thr Gly Arg Cys Trp Gly Pro Thr Glu
            195                 200                 205

Asn His Cys Gln Thr Leu Thr Arg Thr Val Gly Gly Gly Gly Ser Gly
            210                 215                 220

Gly Gly Gly Ser Gly Gly Gly Ser Gly Gly Gly Gly Ser Gly Gly
225                 230                 235                 240

Gly Gly Gly Ala Ser Ser Ala Gly Leu Gly Pro Val Val Arg Cys Glu
                245                 250                 255

Pro Cys Asp Ala Arg Ala Leu Ala Gln Cys Ala Pro Pro Ala Val
            260                 265                 270

Cys Ala Glu Leu Val Arg Glu Pro Gly Cys Gly Cys Cys Leu Thr Cys
            275                 280                 285

Ala Leu Ser Glu Gly Gln Pro Cys Gly Ile Tyr Thr Glu Arg Cys Gly
290                 295                 300

Ser Gly Leu Arg Cys Gln Pro Ser Pro Asp Glu Ala Arg Pro Leu Gln
305                 310                 315                 320

Ala Leu Leu Asp Gly Arg Gly Leu Cys Val Asn Ala Ser Ala Val Ser
                325                 330                 335

Lys Gly His Ala Lys Asp Ser Gln Arg Tyr Lys Val Asp Tyr Glu Ser
            340                 345                 350

Gln Ser Thr Asp Thr Gln Asn Phe Ser Ser Glu Ser Lys Arg Glu Thr
            355                 360                 365

Glu Tyr Gly Pro Cys Arg Arg Glu Met Glu Asp Thr Leu Asn His Leu
370                 375                 380

Lys Phe Leu Asn Val Leu Ser Pro Arg Gly Val His Ile Pro Asn Cys
385                 390                 395                 400

Asp Lys Lys Gly Phe Tyr Lys Lys Gln Cys Arg Pro Ser Lys Gly
                405                 410                 415

Arg Lys Arg Gly Phe Cys Trp Cys Val Asp Lys Tyr Gly Gln Pro Leu
                420                 425                 430

Pro Gly Tyr Thr Thr Lys Gly Lys Glu Asp Val His Cys Tyr Ser Met
            435                 440                 445

Gln Ser Lys Ala Pro Pro Ala Pro Gly Asn Ala Ser Glu Ser Glu Glu
    450                 455                 460

Asp Arg Ser Ala Gly Ile Tyr Ile Phe Ile Ser Asp Thr Gly Arg Pro
465                 470                 475                 480

Phe Val Glu Met Tyr Ser Glu Ile Pro Glu Ile Ile His Met Thr Glu
                485                 490                 495

Gly Arg Glu Leu Val Ile Pro Cys Arg Val Thr Ser Pro Asn Ile Thr
            500                 505                 510

Val Thr Leu Lys Lys Phe Pro Leu Asp Thr Leu Ile Pro Asp Gly Lys
            515                 520                 525

Arg Ile Ile Trp Asp Ser Arg Lys Gly Phe Ile Ile Ser Asn Ala Thr
530                 535                 540
```

Tyr Lys Glu Ile Gly Leu Leu Thr Cys Glu Ala Thr Val Asn Gly His
545                 550                 555                 560

Leu Tyr Lys Thr Asn Tyr Leu Thr His Arg Gln Gly Tyr Arg Ile Tyr
                565                 570                 575

Asp Val Val Leu Ser Pro Ser His Gly Ile Glu Leu Ser Val Gly Glu
            580                 585                 590

Lys Leu Val Leu Asn Cys Thr Ala Arg Thr Glu Leu Asn Val Gly Ile
        595                 600                 605

Asp Phe Asn Trp Glu Tyr Pro Ser Ser Lys His Gln His Lys Lys Leu
    610                 615                 620

Val Asn Arg Asp Leu Lys Thr Gln Ser Gly Ser Glu Met Lys Lys Phe
625                 630                 635                 640

Leu Ser Thr Leu Thr Ile Asp Gly Val Thr Arg Ser Asp Gln Gly Leu
                645                 650                 655

Tyr Thr Cys Ala Ala Ser Ser Gly Leu Met Thr Lys Lys Asn Ser Thr
            660                 665                 670

Phe Val Arg Val His Glu Lys Val Glu Cys Pro Pro Cys Pro Ala Pro
        675                 680                 685

Pro Val Ala Gly Pro Ser Val Phe Leu Phe Pro Pro Lys Pro Lys Asp
    690                 695                 700

Gln Leu Met Ile Ser Arg Thr Pro Glu Val Thr Cys Val Val Val Asp
705                 710                 715                 720

Val Ser His Glu Asp Pro Glu Val Lys Phe Asn Trp Tyr Val Asp Gly
                725                 730                 735

Val Glu Val His Asn Ala Lys Thr Lys Pro Arg Glu Glu Gln Tyr Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Arg Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Lys
    850                 855                 860

Leu Thr Val Asp Lys Ser Arg Trp Gln Gln Gly Asn Val Phe Ser Cys
865                 870                 875                 880

Ser Val Met His Glu Gly Leu His Asn His Tyr Thr Gln Lys Ser Leu
                885                 890                 895

Ser Leu Ser Pro Gly Lys
            900

<210> SEQ ID NO 21
<211> LENGTH: 740
<212> TYPE: PRT
<213> ORGANISM: Artificial Sequence
<220> FEATURE:
<223> OTHER INFORMATION: Synthesized

<400> SEQUENCE: 21

```
Met Ser Glu Val Pro Val Ala Arg Val Trp Leu Val Leu Leu Leu
1               5                   10                  15

Thr Val Gln Val Gly Val Thr Ala Gly Gly Ser Ser Ala Gly Leu
        20                  25                  30

Gly Pro Val Val Arg Cys Glu Pro Cys Asp Ala Arg Ala Leu Ala Gln
            35                  40                  45

Cys Ala Pro Pro Ala Val Cys Ala Glu Leu Val Arg Glu Pro Gly
50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Arg Leu Arg Ala Tyr Leu Leu Pro Ala
            115                 120                 125

Pro Pro Ala Pro Gly Asn Ala Ser Glu Ser Glu Glu Asp Arg Ser Ala
            130                 135                 140

Gly Ser Val Glu Ser Pro Ser Val Ser Ser Thr His Arg Val Ser Asp
145                 150                 155                 160

Pro Lys Phe His Pro Leu His Ser Lys Ile Ile Ile Lys Lys Gly
                165                 170                 175

His Ala Lys Asp Ser Gln Arg Tyr Lys Val Asp Tyr Glu Ser Gln Ser
            180                 185                 190

Thr Asp Thr Gln Asn Phe Ser Ser Glu Ser Lys Arg Glu Thr Glu Tyr
            195                 200                 205

Gly Pro Cys Arg Arg Glu Met Glu Asp Thr Leu Asn His Leu Lys Phe
210                 215                 220

Leu Asn Val Leu Ser Pro Arg Gly Val His Ile Pro Asn Cys Asp Lys
225                 230                 235                 240

Lys Gly Phe Tyr Lys Lys Gln Cys Arg Pro Ser Lys Gly Arg Lys
                245                 250                 255

Arg Gly Phe Cys Trp Cys Val Asp Lys Tyr Gly Gln Pro Leu Pro Gly
            260                 265                 270

Tyr Thr Thr Lys Gly Lys Glu Asp Val His Cys Tyr Ser Met Gln Ser
            275                 280                 285

Lys Ala Pro Pro Ala Pro Gly Asn Ala Ser Glu Ser Glu Glu Asp Arg
            290                 295                 300

Ser Ala Gly Ile Tyr Ile Phe Ile Ser Asp Thr Gly Arg Pro Phe Val
305                 310                 315                 320

Glu Met Tyr Ser Glu Ile Pro Glu Ile Ile His Met Thr Glu Gly Arg
                325                 330                 335

Glu Leu Val Ile Pro Cys Arg Val Thr Ser Pro Asn Ile Thr Val Thr
            340                 345                 350

Leu Lys Lys Phe Pro Leu Asp Thr Leu Ile Pro Asp Gly Lys Arg Ile
            355                 360                 365

Ile Trp Asp Ser Arg Lys Gly Phe Ile Ile Ser Asn Ala Thr Tyr Lys
370                 375                 380

Glu Ile Gly Leu Leu Thr Cys Glu Ala Thr Val Asn Gly His Leu Tyr
385                 390                 395                 400

Lys Thr Asn Tyr Leu Thr His Arg Gln Gly Tyr Arg Ile Tyr Asp Val
                405                 410                 415

Val Leu Ser Pro Ser His Gly Ile Glu Leu Ser Val Gly Glu Lys Leu
```

```
                420             425             430
Val Leu Asn Cys Thr Ala Arg Thr Glu Leu Asn Val Gly Ile Asp Phe
            435             440             445
Asn Trp Glu Tyr Pro Ser Ser Lys His Gln His Lys Lys Leu Val Asn
            450             455             460
Arg Asp Leu Lys Thr Gln Ser Gly Ser Glu Met Lys Lys Phe Leu Ser
465             470             475             480
Thr Leu Thr Ile Asp Gly Val Thr Arg Ser Asp Gln Gly Leu Tyr Thr
            485             490             495
Cys Ala Ala Ser Ser Gly Leu Met Thr Lys Lys Asn Ser Thr Phe Val
            500             505             510
Arg Val His Glu Lys Val Glu Cys Pro Pro Cys Pro Ala Pro Pro Val
            515             520             525
Ala Gly Pro Ser Val Phe Leu Phe Pro Pro Lys Pro Lys Asp Gln Leu
            530             535             540
Met Ile Ser Arg Thr Pro Glu Val Thr Cys Val Val Val Asp Val Ser
545             550             555             560
His Glu Asp Pro Glu Val Lys Phe Asn Trp Tyr Val Asp Gly Val Glu
            565             570             575
Val His Asn Ala Lys Thr Lys Pro Arg Glu Glu Gln Tyr Asn Ser Thr
            580             585             590
Tyr Arg Val Val Ser Val Leu Thr Val Leu His Gln Asp Trp Leu Asn
            595             600             605
Gly Lys Glu Tyr Lys Cys Lys Val Ser Asn Lys Gly Leu Pro Ser Ser
            610             615             620
Ile Glu Lys Thr Ile Ser Lys Ala Lys Gly Gln Pro Arg Glu Pro Gln
625             630             635             640
Val Tyr Thr Leu Pro Pro Ser Arg Glu Glu Met Thr Lys Asn Gln Val
            645             650             655
Ser Leu Thr Cys Leu Val Lys Gly Phe Tyr Pro Ser Asp Ile Ala Val
            660             665             670
Glu Trp Glu Ser Asn Gly Gln Pro Glu Asn Asn Tyr Lys Thr Thr Pro
            675             680             685
Pro Val Leu Asp Ser Asp Gly Ser Phe Phe Leu Tyr Ser Lys Leu Thr
            690             695             700
Val Asp Lys Ser Arg Trp Gln Gln Gly Asn Val Phe Ser Cys Ser Val
705             710             715             720
Met His Glu Gly Leu His Asn His Tyr Thr Gln Lys Ser Leu Ser Leu
            725             730             735
Ser Pro Gly Lys
            740

<210> SEQ ID NO 22
<211> LENGTH: 674
<212> TYPE: PRT
<213> ORGANISM: Artificial Sequence
<220> FEATURE:
<223> OTHER INFORMATION: Synthesized

<400> SEQUENCE: 22

Met Ser Glu Val Pro Val Ala Arg Val Trp Leu Val Leu Leu Leu Leu
1               5                   10                  15
Thr Val Gln Val Gly Val Thr Ala Gly Val Gln Pro Ser Asp Ser Gln
                20                  25                  30
Ser Val Cys Ala Gly Thr Glu Asn Lys Leu Ser Ser Leu Ser Asp Leu
```

```
            35                  40                  45
Glu Gln Gln Tyr Arg Ala Leu Arg Lys Tyr Tyr Glu Asn Cys Glu Val
 50                  55                  60

Val Met Gly Asn Leu Glu Ile Thr Ser Ile Glu His Asn Arg Asp Leu
 65                  70                  75                  80

Ser Phe Leu Arg Ser Val Arg Glu Val Thr Gly Tyr Val Leu Val Ala
                 85                  90                  95

Leu Asn Gln Phe Arg Tyr Leu Pro Leu Glu Asn Leu Arg Ile Ile Arg
                100                 105                 110

Gly Thr Lys Leu Tyr Glu Asp Arg Tyr Ala Leu Ala Ile Phe Leu Asn
                115                 120                 125

Tyr Arg Lys Asp Gly Asn Phe Gly Leu Gln Glu Leu Gly Leu Lys Asn
130                 135                 140

Leu Thr Glu Ile Leu Asn Gly Gly Val Tyr Val Asp Gln Asn Lys Phe
145                 150                 155                 160

Leu Cys Tyr Ala Asp Thr Ile His Trp Gln Asp Ile Val Arg Asn Pro
                165                 170                 175

Trp Pro Ser Asn Leu Thr Leu Val Ser Thr Asn Gly Ser Ser Gly Cys
                180                 185                 190

Gly Arg Cys His Lys Ser Cys Thr Gly Arg Cys Trp Gly Pro Thr Glu
                195                 200                 205

Asn His Cys Gln Thr Leu Thr Arg Thr Val Gly Gly Gly Ser Gly
210                 215                 220

Gly Gly Gly Ser Gly Gly Gly Ser Gly Gly Gly Ser Gly Gly
225                 230                 235                 240

Gly Gly Gly Ala Ser Ser Ala Gly Leu Gly Pro Val Val Arg Cys Glu
                245                 250                 255

Pro Cys Asp Ala Arg Ala Leu Ala Gln Cys Ala Pro Pro Ala Val
                260                 265                 270

Cys Ala Glu Leu Val Arg Glu Pro Gly Cys Gly Cys Cys Leu Thr Cys
                275                 280                 285

Ala Leu Ser Glu Gly Gln Pro Cys Gly Ile Tyr Thr Glu Arg Cys Gly
                290                 295                 300

Ser Gly Leu Arg Cys Gln Pro Ser Pro Asp Glu Ala Arg Pro Leu Gln
305                 310                 315                 320

Ala Leu Leu Asp Gly Arg Gly Leu Cys Val Asn Ala Ser Ala Val Ser
                325                 330                 335

Lys Gly His Ala Lys Asp Ser Gln Arg Tyr Lys Val Asp Tyr Glu Ser
                340                 345                 350

Gln Ser Thr Asp Thr Gln Asn Phe Ser Ser Glu Ser Lys Arg Glu Thr
                355                 360                 365

Glu Tyr Gly Pro Cys Arg Arg Glu Met Glu Asp Thr Leu Asn His Leu
                370                 375                 380

Lys Phe Leu Asn Val Leu Ser Pro Arg Gly Val His Ile Pro Asn Cys
385                 390                 395                 400

Asp Lys Lys Gly Phe Tyr Lys Lys Lys Gln Cys Arg Pro Ser Lys Gly
                405                 410                 415

Arg Lys Arg Gly Phe Cys Trp Cys Val Asp Lys Tyr Gly Gln Pro Leu
                420                 425                 430

Pro Gly Tyr Thr Thr Lys Gly Lys Glu Asp Val His Cys Tyr Ser Met
                435                 440                 445

Gln Ser Lys Val Glu Cys Pro Pro Cys Pro Ala Pro Pro Val Ala Gly
                450                 455                 460
```

Pro Ser Val Phe Leu Phe Pro Pro Lys Pro Lys Asp Gln Leu Met Ile
465                 470                 475                 480

Ser Arg Thr Pro Glu Val Thr Cys Val Val Val Asp Val Ser His Glu
            485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
530                 535                 540

Glu Tyr Lys Cys Lys Val Ser Asn Lys Gly Leu Pro Ser Ser Ile Glu
545                 550                 555                 560

Lys Thr Ile Ser Lys Ala Lys Gly Gln Pro Arg Glu Pro Gln Val Tyr
                565                 570                 575

Thr Leu Pro Pro Ser Arg Glu Glu Met Thr Lys Asn Gln Val Ser Leu
            580                 585                 590

Thr Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Gly Leu His Asn His Tyr Thr Gln Lys Ser Leu Ser Leu Ser Pro
            660                 665                 670

Gly Lys

<210> SEQ ID NO 23
<211> LENGTH: 376
<212> TYPE: PRT
<213> ORGANISM: Artificial Sequence
<220> FEATURE:
<223> OTHER INFORMATION: Synthesized

<400> SEQUENCE: 23

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
                20                  25                  30

Gly Pro Val Val Arg Cys Glu Pro Cys Asp Ala Arg Ala Leu Ala Gln
            35                  40                  45

Cys Ala Pro Pro Pro Ala Val Cys Ala Glu Leu Val Arg Glu Pro Gly
50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Lys Gly His Ala Lys Asp Ser Gln Arg
            115                 120                 125

Tyr Lys Val Asp Tyr Glu Ser Gln Ser Thr Asp Thr Gln Asn Phe Ser
        130                 135                 140

-continued

Ser Glu Ser Lys Arg Glu Thr Glu Tyr Val Glu Cys Pro Pro Cys Pro
145                 150                 155                 160

Ala Pro Pro Val Ala Gly Pro Ser Val Phe Leu Phe Pro Pro Lys Pro
            165                 170                 175

Lys Asp Gln Leu Met Ile Ser Arg Thr Pro Glu Val Thr Cys Val Val
        180                 185                 190

Val Asp Val Ser His Glu Asp Pro Glu Val Lys Phe Asn Trp Tyr Val
    195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Gly
            245                 250                 255

Leu Pro Ser Ser Ile Glu Lys Thr Ile Ser Lys Ala Lys Gly Gln Pro
        260                 265                 270

Arg Glu Pro Gln Val Tyr Thr Leu Pro Pro Ser Arg Glu Glu Met Thr
    275                 280                 285

Lys Asn Gln Val Ser Leu Thr Cys Leu Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
            325                 330                 335

Ser Lys Leu Thr Val Asp Lys Ser Arg Trp Gln Gln Gly Asn Val Phe
        340                 345                 350

Ser Cys Ser Val Met His Glu Gly Leu His Asn His Tyr Thr Gln Lys
    355                 360                 365

Ser Leu Ser Leu Ser Pro Gly Lys
370                 375

<210> SEQ ID NO 24
<211> LENGTH: 342
<212> TYPE: PRT
<213> ORGANISM: Artificial Sequence
<220> FEATURE:
<223> OTHER INFORMATION: Synthesized

<400> SEQUENCE: 24

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Val Glu Cys Pro Pro Cys Pro Ala Pro
        115                 120                 125

```
Pro Val Ala Gly Pro Ser Val Phe Leu Phe Pro Pro Lys Pro Lys Asp
    130                 135                 140

Gln Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Gly Leu His Asn His Tyr Thr Gln Lys Ser Leu
                325                 330                 335

Ser Leu Ser Pro Gly Lys
            340

<210> SEQ ID NO 25
<211> LENGTH: 346
<212> TYPE: PRT
<213> ORGANISM: Artificial Sequence
<220> FEATURE:
<223> OTHER INFORMATION: Synthesized

<400> SEQUENCE: 25

Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Val Asn
            20                  25                  30

Ala Ser Ala Val Ser Arg Leu Arg Ala Tyr Leu Leu Pro Ala Pro Pro
        35                  40                  45

Ala Pro Gly Asn Ala Ser Glu Ser Glu Glu Asp Arg Ser Ala Gly Ser
    50                  55                  60

Val Glu Ser Pro Ser Val Ser Ser Thr His Arg Val Ser Asp Pro Lys
65                  70                  75                  80

Phe His Pro Leu His Ser Lys Ile Ile Ile Ile Lys Lys Gly His Ala
                85                  90                  95

Lys Asp Ser Gln Arg Tyr Lys Val Asp Tyr Glu Ser Gln Ser Thr Asp
            100                 105                 110

Thr Gln Asn Phe Ser Ser Glu Ser Lys Arg Glu Val Glu Cys Pro Pro
        115                 120                 125

Cys Pro Ala Pro Pro Val Ala Gly Pro Ser Val Phe Leu Phe Pro Pro
    130                 135                 140
```

```
Lys Pro Lys Asp Gln Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Gly Leu His Asn His Tyr Thr
                325                 330                 335

Gln Lys Ser Leu Ser Leu Ser Pro Gly Lys
            340                 345

<210> SEQ ID NO 26
<211> LENGTH: 743
<212> TYPE: PRT
<213> ORGANISM: Artificial Sequence
<220> FEATURE:
<223> OTHER INFORMATION: Synthesized

<400> SEQUENCE: 26

Met Ser Glu Val Pro Val Ala Arg Val Trp Leu Val Leu Leu Leu Leu
1               5                   10                  15

Thr Val Gln Val Gly Val Thr Ala Gly Ala Ala Ala Ser Gly Gly Gly
            20                  25                  30

Ser Gly Gly Gly Gly Ser Gly Gly Gly Gly Ser Gly Gly Gly Gly Pro
        35                  40                  45

Val Ile Thr Ser Ile Ser Pro Lys Tyr Gly Pro Met Ala Gly Gly Thr
    50                  55                  60

Leu Leu Thr Leu Thr Gly Asn Tyr Leu Asn Ser Gly Asn Ser Arg His
65                  70                  75                  80

Ile Ser Ile Gly Gly Lys Thr Cys Thr Leu Lys Ser Val Ser Asn Ser
                85                  90                  95

Ile Leu Glu Cys Tyr Thr Pro Ala Gln Thr Ile Ser Thr Glu Phe Ala
            100                 105                 110

Val Lys Leu Lys Ile Asp Leu Ala Asn Arg Glu Thr Ser Ile Phe Ser
        115                 120                 125

Tyr Arg Glu Asp Pro Ile Val Tyr Glu Ile His Pro Thr Lys Ser Phe
    130                 135                 140

Ile Ser Thr Trp Trp Lys Glu Pro Leu Asn Ile Val Ser Phe Leu Phe
145                 150                 155                 160
```

-continued

```
Cys Phe Ala Ser Gly Gly Ser Thr Ile Thr Gly Val Gly Lys Asn Leu
            165                 170                 175
Asn Ser Val Ser Val Pro Arg Met Val Ile Asn Val His Glu Ala Gly
        180                 185                 190
Arg Asn Phe Thr Val Ala Cys Gln His Arg Ser Asn Ser Glu Ile Ile
    195                 200                 205
Cys Cys Thr Thr Pro Ser Leu Gln Gln Leu Asn Leu Gln Leu Pro Leu
210                 215                 220
Lys Thr Lys Ala Phe Phe Met Leu Asp Gly Ile Leu Ser Lys Tyr Phe
225                 230                 235                 240
Asp Leu Ile Tyr Val His Ser Gly Gly Ser Gly Gly Gly Thr Gly
                245                 250                 255
Gly Ala Ser Ser Ala Gly Leu Gly Pro Val Val Arg Cys Glu Pro Cys
            260                 265                 270
Asp Ala Arg Ala Leu Ala Gln Cys Ala Pro Pro Ala Val Cys Ala
        275                 280                 285
Glu Leu Val Arg Glu Pro Gly Cys Gly Cys Cys Leu Thr Cys Ala Leu
    290                 295                 300
Ser Glu Gly Gln Pro Cys Gly Ile Tyr Thr Glu Arg Cys Gly Ser Gly
305                 310                 315                 320
Leu Arg Cys Gln Pro Ser Pro Asp Glu Ala Arg Pro Leu Gln Ala Leu
                325                 330                 335
Leu Asp Gly Arg Gly Leu Cys Val Asn Ala Ser Ala Val Ser Arg Leu
            340                 345                 350
Arg Ala Tyr Leu Leu Pro Ala Pro Pro Ala Pro Gly Asn Ala Ser Glu
        355                 360                 365
Ser Glu Glu Asp Arg Ser Ala Gly Ser Val Glu Ser Pro Ser Val Ser
    370                 375                 380
Ser Thr His Arg Val Ser Asp Pro Lys Phe His Pro Leu His Ser Lys
385                 390                 395                 400
Ile Ile Ile Ile Lys Lys Gly His Ala Lys Asp Ser Gln Arg Tyr Lys
                405                 410                 415
Val Asp Tyr Glu Ser Gln Ser Thr Asp Thr Gln Asn Phe Ser Ser Glu
            420                 425                 430
Ser Lys Arg Glu Thr Glu Tyr Gly Pro Cys Arg Arg Glu Met Glu Asp
        435                 440                 445
Thr Leu Asn His Leu Lys Phe Leu Asn Val Leu Ser Pro Arg Gly Val
    450                 455                 460
His Ile Pro Asn Cys Asp Lys Lys Gly Phe Tyr Lys Lys Lys Gln Cys
465                 470                 475                 480
Arg Pro Ser Lys Gly Arg Lys Arg Gly Phe Cys Trp Cys Val Asp Lys
                485                 490                 495
Tyr Gly Gln Pro Leu Pro Gly Tyr Thr Thr Lys Gly Lys Glu Asp Val
            500                 505                 510
His Cys Tyr Ser Met Gln Ser Lys Val Glu Cys Pro Pro Cys Pro Ala
        515                 520                 525
Pro Pro Val Ala Gly Pro Ser Val Phe Leu Phe Pro Pro Lys Pro Lys
    530                 535                 540
Asp Gln Leu Met Ile Ser Arg Thr Pro Glu Val Thr Cys Val Val Val
545                 550                 555                 560
Asp Val Ser His Glu Asp Pro Glu Val Lys Phe Asn Trp Tyr Val Asp
                565                 570                 575
Gly Val Glu Val His Asn Ala Lys Thr Lys Pro Arg Glu Glu Gln Tyr
```

```
                 580                 585                 590
Asn Ser Thr Tyr Arg Val Val Ser Val Leu Thr Val Leu His Gln Asp
            595                 600                 605

Trp Leu Asn Gly Lys Glu Tyr Lys Cys Lys Val Ser Asn Lys Gly Leu
        610                 615                 620

Pro Ser Ser Ile Glu Lys Thr Ile Ser Lys Ala Lys Gly Gln Pro Arg
625                 630                 635                 640

Glu Pro Gln Val Tyr Thr Leu Pro Pro Ser Arg Glu Glu Met Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Val Leu Asp Ser Asp Gly Ser Phe Phe Leu Tyr Ser
    690                 695                 700

Lys Leu Thr Val Asp Lys Ser Arg Trp Gln Gln Gly Asn Val Phe Ser
705                 710                 715                 720

Cys Ser Val Met His Glu Gly Leu His Asn His Tyr Thr Gln Lys Ser
                725                 730                 735

Leu Ser Leu Ser Pro Gly Lys
            740

<210> SEQ ID NO 27
<211> LENGTH: 659
<212> TYPE: PRT
<213> ORGANISM: Artificial Sequence
<220> FEATURE:
<223> OTHER INFORMATION: Synthesized

<400> SEQUENCE: 27

Met Ser Glu Val Pro Val Ala Arg Val Trp Leu Val Leu Leu Leu Leu
1               5                   10                  15

Thr Val Gln Val Gly Val Thr Ala Gly Ala Ala Ser Gly Gly Gly Gly
            20                  25                  30

Ser Gly Gly Gly Gly Ser Gly Gly Gly Gly Ser Gly Gly Gly Gly Asp
        35                  40                  45

Pro Ile Val Tyr Glu Ile His Pro Thr Lys Ser Phe Ile Ser Thr Trp
    50                  55                  60

Trp Lys Glu Pro Leu Asn Ile Val Ser Phe Leu Phe Cys Phe Ala Ser
65                  70                  75                  80

Gly Gly Ser Thr Ile Thr Gly Val Gly Lys Asn Leu Asn Ser Val Ser
                85                  90                  95

Val Pro Arg Met Val Ile Asn Val His Glu Ala Gly Arg Asn Phe Thr
            100                 105                 110

Val Ala Cys Gln His Arg Ser Asn Ser Glu Ile Ile Cys Cys Thr Thr
        115                 120                 125

Pro Ser Leu Gln Gln Leu Asn Leu Gln Leu Pro Leu Lys Thr Lys Ala
    130                 135                 140

Phe Phe Met Leu Asp Gly Ile Leu Ser Lys Tyr Phe Asp Leu Ile Tyr
145                 150                 155                 160

Val His Ser Gly Gly Ser Gly Gly Thr Gly Gly Ala Ser Ser
                165                 170                 175

Ala Gly Leu Gly Pro Val Val Arg Cys Glu Pro Cys Asp Ala Arg Ala
            180                 185                 190

Leu Ala Gln Cys Ala Pro Pro Ala Val Cys Ala Glu Leu Val Arg
```

-continued

```
            195                 200                 205
Glu Pro Gly Cys Gly Cys Cys Leu Thr Cys Ala Leu Ser Glu Gly Gln
210                 215                 220

Pro Cys Gly Ile Tyr Thr Glu Arg Cys Gly Ser Gly Leu Arg Cys Gln
225                 230                 235                 240

Pro Ser Pro Asp Glu Ala Arg Pro Leu Gln Ala Leu Leu Asp Gly Arg
                245                 250                 255

Gly Leu Cys Val Asn Ala Ser Ala Val Ser Arg Leu Arg Ala Tyr Leu
            260                 265                 270

Leu Pro Ala Pro Pro Ala Pro Gly Asn Ala Ser Glu Ser Glu Glu Asp
        275                 280                 285

Arg Ser Ala Gly Ser Val Glu Ser Pro Ser Val Ser Ser Thr His Arg
    290                 295                 300

Val Ser Asp Pro Lys Phe His Pro Leu His Ser Lys Ile Ile Ile Ile
305                 310                 315                 320

Lys Lys Gly His Ala Lys Asp Ser Gln Arg Tyr Lys Val Asp Tyr Glu
                325                 330                 335

Ser Gln Ser Thr Asp Thr Gln Asn Phe Ser Ser Glu Ser Lys Arg Glu
            340                 345                 350

Thr Glu Tyr Gly Pro Cys Arg Arg Glu Met Glu Asp Thr Leu Asn His
        355                 360                 365

Leu Lys Phe Leu Asn Val Leu Ser Pro Arg Gly Val His Ile Pro Asn
    370                 375                 380

Cys Asp Lys Lys Gly Phe Tyr Lys Lys Gln Cys Arg Pro Ser Lys
385                 390                 395                 400

Gly Arg Lys Arg Gly Phe Cys Trp Cys Val Asp Lys Tyr Gly Gln Pro
                405                 410                 415

Leu Pro Gly Tyr Thr Thr Lys Gly Lys Glu Asp Val His Cys Tyr Ser
            420                 425                 430

Met Gln Ser Lys Val Glu Cys Pro Pro Cys Pro Ala Pro Pro Val Ala
        435                 440                 445

Gly Pro Ser Val Phe Leu Phe Pro Pro Lys Pro Lys Asp Gln Leu Met
    450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
        515                 520                 525

Lys Glu Tyr Lys Cys Lys Val Ser Asn Lys Gly Leu Pro Ser Ser Ile
    530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Glu Glu Met Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Thr Thr Pro Pro
        595                 600                 605

Val Leu Asp Ser Asp Gly Ser Phe Phe Leu Tyr Ser Lys Leu Thr Val
    610                 615                 620
```

```
Asp Lys Ser Arg Trp Gln Gln Gly Asn Val Phe Ser Cys Ser Val Met
625                 630                 635                 640

His Glu Gly Leu His Asn His Tyr Thr Gln Lys Ser Leu Ser Leu Ser
                645                 650                 655

Pro Gly Lys

<210> SEQ ID NO 28
<211> LENGTH: 737
<212> TYPE: PRT
<213> ORGANISM: Artificial Sequence
<220> FEATURE:
<223> OTHER INFORMATION: Synthesized

<400> SEQUENCE: 28

Met Ser Glu Val Pro Val Ala Arg Val Trp Leu Val Leu Leu Leu Leu
1               5                   10                  15

Thr Val Gln Val Gly Val Thr Ala Gly Ala Ala Ala Asp Pro Ile Val
            20                  25                  30

Tyr Glu Ile His Pro Thr Lys Ser Phe Ile Ser Thr Trp Trp Lys Glu
        35                  40                  45

Pro Leu Asn Ile Val Ser Phe Leu Phe Cys Phe Ala Ser Gly Gly Ser
50                  55                  60

Thr Ile Thr Gly Val Gly Lys Asn Leu Asn Ser Val Ser Val Pro Arg
65                  70                  75                  80

Met Val Ile Asn Val His Glu Ala Gly Arg Asn Phe Thr Val Ala Cys
                85                  90                  95

Gln His Arg Ser Asn Ser Glu Ile Ile Cys Cys Thr Thr Pro Ser Leu
            100                 105                 110

Gln Gln Leu Asn Leu Gln Leu Pro Leu Lys Thr Lys Ala Phe Phe Met
        115                 120                 125

Leu Asp Gly Ile Leu Ser Lys Tyr Phe Asp Leu Ile Tyr Val His Asn
130                 135                 140

Pro Val Phe Lys Pro Phe Glu Lys Pro Val Met Ile Ser Met Gly Asn
145                 150                 155                 160

Glu Asn Val Leu Glu Ile Lys Gly Asn Asp Ile Asp Pro Glu Ala Val
                165                 170                 175

Lys Gly Glu Val Leu Lys Val Gly Asn Lys Ser Cys Glu Asn Ile His
            180                 185                 190

Leu His Ser Glu Ala Val Leu Cys Thr Val Pro Asn Asp Leu Leu Lys
        195                 200                 205

Leu Asn Ser Glu Leu Asn Ile Glu Trp Lys Gln Ala Ile Ser Ser Thr
210                 215                 220

Val Leu Gly Lys Val Ile Val Gln Pro Asp Gln Asn Phe Thr Gly Ser
225                 230                 235                 240

Gly Gly Gly Ser Gly Gly Gly Ser Thr Gly Gly Ala Ser Ser Ala Gly
                245                 250                 255

Leu Gly Pro Val Val Arg Cys Glu Pro Cys Asp Ala Arg Ala Leu Ala
            260                 265                 270

Gln Cys Ala Pro Pro Ala Val Cys Ala Glu Leu Val Arg Glu Pro
        275                 280                 285

Gly Cys Gly Cys Cys Leu Thr Cys Ala Leu Ser Glu Gly Gln Pro Cys
290                 295                 300

Gly Ile Tyr Thr Glu Arg Cys Gly Ser Gly Leu Arg Cys Gln Pro Ser
305                 310                 315                 320
```

```
Pro Asp Glu Ala Arg Pro Leu Gln Ala Leu Leu Asp Gly Arg Gly Leu
            325                 330                 335
Cys Val Asn Ala Ser Ala Val Ser Arg Leu Arg Ala Tyr Leu Leu Pro
        340                 345                 350
Ala Pro Pro Ala Pro Gly Asn Ala Ser Glu Ser Glu Glu Asp Arg Ser
        355                 360                 365
Ala Gly Ser Val Glu Ser Pro Ser Val Ser Ser Thr His Arg Val Ser
    370                 375                 380
Asp Pro Lys Phe His Pro Leu His Ser Lys Ile Ile Ile Lys Lys
385                 390                 395                 400
Gly His Ala Lys Asp Ser Gln Arg Tyr Lys Val Asp Tyr Glu Ser Gln
                405                 410                 415
Ser Thr Asp Thr Gln Asn Phe Ser Ser Glu Ser Lys Arg Glu Thr Glu
            420                 425                 430
Tyr Gly Pro Cys Arg Arg Glu Met Glu Asp Thr Leu Asn His Leu Lys
        435                 440                 445
Phe Leu Asn Val Leu Ser Pro Arg Gly Val His Ile Pro Asn Cys Asp
    450                 455                 460
Lys Lys Gly Phe Tyr Lys Lys Gln Cys Arg Pro Ser Lys Gly Arg
465                 470                 475                 480
Lys Arg Gly Phe Cys Trp Cys Val Asp Lys Tyr Gly Gln Pro Leu Pro
                485                 490                 495
Gly Tyr Thr Thr Lys Gly Lys Glu Asp Val His Cys Tyr Ser Met Gln
            500                 505                 510
Ser Lys Val Glu Cys Pro Pro Cys Pro Ala Pro Pro Val Ala Gly Pro
        515                 520                 525
Ser Val Phe Leu Phe Pro Pro Lys Pro Lys Asp Gln Leu Met Ile Ser
    530                 535                 540
Arg Thr Pro Glu Val Thr Cys Val Val Val Asp Val Ser His Glu Asp
545                 550                 555                 560
Pro Glu Val Lys Phe Asn Trp Tyr Val Asp Gly Val Glu Val His Asn
                565                 570                 575
Ala Lys Thr Lys Pro Arg Glu Glu Gln Tyr Asn Ser Thr Tyr Arg Val
            580                 585                 590
Val Ser Val Leu Thr Val Leu His Gln Asp Trp Leu Asn Gly Lys Glu
        595                 600                 605
Tyr Lys Cys Lys Val Ser Asn Lys Gly Leu Pro Ser Ser Ile Glu Lys
    610                 615                 620
Thr Ile Ser Lys Ala Lys Gly Gln Pro Arg Glu Pro Gln Val Tyr Thr
625                 630                 635                 640
Leu Pro Pro Ser Arg Glu Glu Met Thr Lys Asn Gln Val Ser Leu Thr
                645                 650                 655
Cys Leu Val Lys Gly Phe Tyr Pro Ser Asp Ile Ala Val Glu Trp Glu
            660                 665                 670
Ser Asn Gly Gln Pro Glu Asn Asn Tyr Lys Thr Thr Pro Pro Val Leu
        675                 680                 685
Asp Ser Asp Gly Ser Phe Phe Leu Tyr Ser Lys Leu Thr Val Asp Lys
    690                 695                 700
Ser Arg Trp Gln Gln Gly Asn Val Phe Ser Cys Ser Val Met His Glu
705                 710                 715                 720
Gly Leu His Asn His Tyr Thr Gln Lys Ser Leu Ser Leu Ser Pro Gly
                725                 730                 735
Lys
```

<210> SEQ ID NO 29
<211> LENGTH: 754
<212> TYPE: PRT
<213> ORGANISM: Artificial Sequence
<220> FEATURE:
<223> OTHER INFORMATION: Synthesized

<400> SEQUENCE: 29

```
Met Ser Glu Val Pro Val Ala Arg Val Trp Leu Val Leu Leu Leu Leu
1               5                   10                  15

Thr Val Gln Val Gly Val Thr Ala Gly Gly Ala Ser Ser Ala Gly Leu
            20                  25                  30

Gly Pro Val Val Arg Cys Glu Pro Cys Asp Ala Arg Ala Leu Ala Gln
        35                  40                  45

Cys Ala Pro Pro Pro Ala Val Cys Ala Glu Leu Val Arg Glu Pro Gly
    50                  55                  60

Cys Gly Cys Cys Leu Thr Cys Ala Leu Ser Glu Gly Gln Pro Cys Gly
65                  70                  75                  80

Ile Tyr Thr Glu Arg Cys Gly Ser Gly Leu Arg Cys Gln Pro Ser Pro
                85                  90                  95

Asp Glu Ala Arg Pro Leu Gln Ala Leu Leu Asp Gly Arg Gly Leu Cys
            100                 105                 110

Val Asn Ala Ser Ala Val Ser Arg Leu Arg Ala Tyr Leu Leu Pro Ala
        115                 120                 125

Pro Pro Ala Pro Gly Asn Ala Ser Glu Ser Glu Glu Asp Arg Ser Ala
    130                 135                 140

Gly Ser Val Glu Ser Pro Ser Val Ser Ser Thr His Arg Val Ser Asp
145                 150                 155                 160

Pro Lys Phe His Pro Leu His Ser Lys Ile Ile Ile Lys Lys Gly
                165                 170                 175

His Ala Lys Asp Ser Gln Arg Tyr Lys Val Asp Tyr Glu Ser Gln Ser
            180                 185                 190

Thr Asp Thr Gln Asn Phe Ser Ser Glu Ser Lys Arg Glu Thr Glu Tyr
        195                 200                 205

Gly Pro Cys Arg Arg Glu Met Glu Asp Thr Leu Asn His Leu Lys Phe
    210                 215                 220

Leu Asn Val Leu Ser Pro Arg Gly Val His Ile Pro Asn Cys Asp Lys
225                 230                 235                 240

Lys Gly Phe Tyr Lys Lys Gln Cys Arg Pro Ser Lys Gly Arg Lys
                245                 250                 255

Arg Gly Phe Cys Trp Cys Val Asp Lys Tyr Gly Gln Pro Leu Pro Gly
            260                 265                 270

Tyr Thr Thr Lys Gly Lys Glu Asp Val His Cys Tyr Ser Met Gln Ser
        275                 280                 285

Lys Ala Ala Ser Gly Gly Ser Gly Gly Gly Ser Gly Gly
    290                 295                 300

Gly Gly Ser Gly Gly Asp Pro Ile Val Tyr Glu Ile His Pro Thr Lys
305                 310                 315                 320

Ser Phe Ile Ser Thr Trp Trp Lys Glu Pro Leu Asn Ile Val Ser Phe
                325                 330                 335

Leu Phe Cys Phe Ala Ser Gly Gly Ser Thr Ile Thr Gly Val Gly Lys
            340                 345                 350

Asn Leu Asn Ser Val Ser Val Pro Arg Met Val Ile Asn Val His Glu
        355                 360                 365
```

```
Ala Gly Arg Asn Phe Thr Val Ala Cys Gln His Arg Ser Asn Ser Glu
    370                 375                 380

Ile Ile Cys Cys Thr Thr Pro Ser Leu Gln Gln Leu Asn Leu Gln Leu
385                 390                 395                 400

Pro Leu Lys Thr Lys Ala Phe Phe Met Leu Asp Gly Ile Leu Ser Lys
                405                 410                 415

Tyr Phe Asp Leu Ile Tyr Val His Asn Pro Val Phe Lys Pro Phe Glu
                420                 425                 430

Lys Pro Val Met Ile Ser Met Gly Asn Glu Asn Val Leu Glu Ile Lys
                435                 440                 445

Gly Asn Asp Ile Asp Pro Glu Ala Val Lys Gly Glu Val Leu Lys Val
    450                 455                 460

Gly Asn Lys Ser Cys Glu Asn Ile His Leu His Ser Glu Ala Val Leu
465                 470                 475                 480

Cys Thr Val Pro Asn Asp Leu Leu Lys Leu Asn Ser Glu Leu Asn Ile
                485                 490                 495

Glu Trp Lys Gln Ala Ile Ser Ser Thr Val Leu Gly Lys Val Ile Val
                500                 505                 510

Gln Pro Asp Gln Asn Phe Thr Gly Ser Gly Gly Ser Gly Gly Gly
            515                 520                 525

Ser Thr Gly Val Glu Cys Pro Pro Cys Pro Ala Pro Pro Val Ala Gly
    530                 535                 540

Pro Ser Val Phe Leu Phe Pro Pro Lys Pro Lys Asp Gln Leu Met Ile
545                 550                 555                 560

Ser Arg Thr Pro Glu Val Thr Cys Val Val Asp Val Ser His Glu
                565                 570                 575

Asp Pro Glu Val Lys Phe Asn Trp Tyr Val Asp Gly Val Glu Val His
                580                 585                 590

Asn Ala Lys Thr Lys Pro Arg Glu Glu Gln Tyr Asn Ser Thr Tyr Arg
            595                 600                 605

Val Val Ser Val Leu Thr Val Leu His Gln Asp Trp Leu Asn Gly Lys
    610                 615                 620

Glu Tyr Lys Cys Lys Val Ser Asn Lys Gly Leu Pro Ser Ser Ile Glu
625                 630                 635                 640

Lys Thr Ile Ser Lys Ala Lys Gly Gln Pro Arg Glu Pro Gln Val Tyr
                645                 650                 655

Thr Leu Pro Pro Ser Arg Glu Glu Met Thr Lys Asn Gln Val Ser Leu
            660                 665                 670

Thr Cys Leu Val Lys Gly Phe Tyr Pro Ser Asp Ile Ala Val Glu Trp
        675                 680                 685

Glu Ser Asn Gly Gln Pro Glu Asn Asn Tyr Lys Thr Thr Pro Pro Val
    690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
                725                 730                 735

Glu Gly Leu His Asn His Tyr Thr Gln Lys Ser Leu Ser Leu Ser Pro
            740                 745                 750

Gly Lys

<210> SEQ ID NO 30
<211> LENGTH: 645
<212> TYPE: PRT
```

<213> ORGANISM: Artificial Sequence
<220> FEATURE:
<223> OTHER INFORMATION: Synthesized

<400> SEQUENCE: 30

```
Met Ser Glu Val Pro Val Ala Arg Val Trp Leu Val Leu Leu Leu
1               5                   10                  15

Thr Val Gln Val Gly Val Thr Ala Gly Ala Ala Ser Gly Gly Gly
            20                  25                  30

Ser Gly Gly Gly Gly Ser Gly Gly Gly Ser Gly Gly Asp Leu Ile
        35                  40                  45

Tyr Val His Asn Pro Val Phe Lys Pro Phe Glu Lys Pro Val Met Ile
    50                  55                  60

Ser Met Gly Asn Glu Asn Val Leu Glu Ile Lys Gly Asn Asp Ile Asp
65                  70                  75                  80

Pro Glu Ala Val Lys Gly Val Leu Lys Val Gly Asn Lys Ser Cys
                85                  90                  95

Glu Asn Ile His Leu His Ser Glu Ala Val Leu Cys Thr Val Pro Asn
                100                 105                 110

Asp Leu Leu Lys Leu Asn Ser Glu Leu Asn Ile Glu Trp Lys Gln Ala
                115                 120                 125

Ile Ser Ser Thr Val Leu Gly Lys Val Ile Val Gln Pro Asp Gln Asn
                130                 135                 140

Phe Thr Gly Ser Gly Gly Gly Ser Gly Gly Gly Ser Thr Gly Gly Ala
145                 150                 155                 160

Ser Ser Ala Gly Leu Gly Pro Val Val Arg Cys Glu Pro Cys Asp Ala
                165                 170                 175

Arg Ala Leu Ala Gln Cys Ala Pro Pro Ala Val Cys Ala Glu Leu
                180                 185                 190

Val Arg Glu Pro Gly Cys Gly Cys Cys Leu Thr Cys Ala Leu Ser Glu
                195                 200                 205

Gly Gln Pro Cys Gly Ile Tyr Thr Glu Arg Cys Gly Ser Gly Leu Arg
                210                 215                 220

Cys Gln Pro Ser Pro Asp Glu Ala Arg Pro Leu Gln Ala Leu Leu Asp
225                 230                 235                 240

Gly Arg Gly Leu Cys Val Asn Ala Ser Ala Val Ser Arg Leu Arg Ala
                245                 250                 255

Tyr Leu Leu Pro Ala Pro Pro Ala Pro Gly Asn Ala Ser Glu Ser Glu
                260                 265                 270

Glu Asp Arg Ser Ala Gly Ser Val Glu Ser Pro Ser Val Ser Ser Thr
                275                 280                 285

His Arg Val Ser Asp Pro Lys Phe His Pro Leu His Ser Lys Ile Ile
                290                 295                 300

Ile Ile Lys Lys Gly His Ala Lys Asp Ser Gln Arg Tyr Lys Val Asp
305                 310                 315                 320

Tyr Glu Ser Gln Ser Thr Asp Thr Gln Asn Phe Ser Ser Glu Ser Lys
                325                 330                 335

Arg Glu Thr Glu Tyr Gly Pro Cys Arg Arg Glu Met Glu Asp Thr Leu
                340                 345                 350

Asn His Leu Lys Phe Leu Asn Val Leu Ser Pro Arg Gly Val His Ile
                355                 360                 365

Pro Asn Cys Asp Lys Lys Gly Phe Tyr Lys Lys Gln Cys Arg Pro
                370                 375                 380

Ser Lys Gly Arg Lys Arg Gly Phe Cys Trp Cys Val Asp Lys Tyr Gly
```

```
385                 390                 395                 400
Gln Pro Leu Pro Gly Tyr Thr Thr Lys Gly Lys Glu Asp Val His Cys
                405                 410                 415

Tyr Ser Met Gln Ser Lys Val Glu Cys Pro Cys Pro Ala Pro Pro
            420                 425                 430

Val Ala Gly Pro Ser Val Phe Leu Phe Pro Pro Lys Pro Lys Asp Gln
                435                 440                 445

Leu Met Ile Ser Arg Thr Pro Glu Val Thr Cys Val Val Val Asp Val
            450                 455                 460

Ser His Glu Asp Pro Glu Val Lys Phe Asn Trp Tyr Val Asp Gly Val
465                 470                 475                 480

Glu Val His Asn Ala Lys Thr Lys Pro Arg Glu Gln Tyr Asn Ser
                485                 490                 495

Thr Tyr Arg Val Val Ser Val Leu Thr Val Leu His Gln Asp Trp Leu
            500                 505                 510

Asn Gly Lys Glu Tyr Lys Cys Lys Val Ser Asn Lys Gly Leu Pro Ser
                515                 520                 525

Ser Ile Glu Lys Thr Ile Ser Lys Ala Lys Gly Gln Pro Arg Glu Pro
            530                 535                 540

Gln Val Tyr Thr Leu Pro Pro Ser Arg Glu Glu Met Thr Lys Asn Gln
545                 550                 555                 560

Val Ser Leu Thr Cys Leu Val Lys Gly Phe Tyr Pro Ser Asp Ile Ala
                565                 570                 575

Val Glu Trp Glu Ser Asn Gly Gln Pro Glu Asn Asn Tyr Lys Thr Thr
            580                 585                 590

Pro Pro Val Leu Asp Ser Asp Gly Ser Phe Phe Leu Tyr Ser Lys Leu
                595                 600                 605

Thr Val Asp Lys Ser Arg Trp Gln Gln Gly Asn Val Phe Ser Cys Ser
            610                 615                 620

Val Met His Glu Gly Leu His Asn His Tyr Thr Gln Lys Ser Leu Ser
625                 630                 635                 640

Leu Ser Pro Gly Lys
                645

<210> SEQ ID NO 31
<211> LENGTH: 623
<212> TYPE: PRT
<213> ORGANISM: Artificial Sequence
<220> FEATURE:
<223> OTHER INFORMATION: Synthesized

<400> SEQUENCE: 31

Met Ser Glu Val Pro Val Ala Arg Val Trp Leu Val Leu Leu Leu
1               5                   10                  15

Thr Val Gln Val Gly Val Thr Ala Gly Ala Ala Ala Glu Ser Ile Arg
            20                  25                  30

Glu Thr Glu Val Ile Asp Pro Gln Asp Leu Leu Glu Gly Arg Tyr Phe
        35                  40                  45

Ser Gly Ala Leu Pro Asp Asp Glu Asp Val Val Gly Pro Gly Gln Glu
    50                  55                  60

Ser Asp Asp Phe Glu Leu Ser Gly Ser Gly Asp Leu Asp Leu Glu
65                  70                  75                  80

Asp Ser Met Ile Gly Pro Glu Val Val His Pro Leu Val Pro Leu Asp
                85                  90                  95

Asn His Ile Pro Glu Arg Ala Gly Ser Gly Ser Gln Val Pro Thr Glu
```

```
                100             105             110
Pro Lys Lys Leu Glu Glu Asn Glu Val Ile Pro Lys Arg Ile Ser Pro
            115                 120             125

Val Glu Glu Ser Glu Asp Thr Gly Ala Ser Ala Gly Leu Gly
        130              135             140

Pro Val Val Arg Cys Glu Pro Cys Asp Ala Arg Ala Leu Ala Gln Cys
145             150              155                         160

Ala Pro Pro Ala Val Cys Ala Glu Leu Val Arg Glu Pro Gly Cys
            165              170             175

Gly Cys Cys Leu Thr Cys Ala Leu Ser Glu Gly Gln Pro Cys Gly Ile
            180              185             190

Tyr Thr Glu Arg Cys Gly Ser Gly Leu Arg Cys Gln Pro Ser Pro Asp
        195             200             205

Glu Ala Arg Pro Leu Gln Ala Leu Leu Asp Gly Arg Gly Leu Cys Val
        210             215             220

Asn Ala Ser Ala Val Ser Arg Leu Arg Ala Tyr Leu Leu Pro Ala Pro
225             230             235             240

Pro Ala Pro Gly Asn Ala Ser Glu Ser Glu Glu Asp Arg Ser Ala Gly
            245             250             255

Ser Val Glu Ser Pro Ser Val Ser Ser Thr His Arg Val Ser Asp Pro
            260             265             270

Lys Phe His Pro Leu His Ser Lys Ile Ile Ile Lys Lys Gly His
            275             280             285

Ala Lys Asp Ser Gln Arg Tyr Lys Val Asp Tyr Glu Ser Gln Ser Thr
        290             295             300

Asp Thr Gln Asn Phe Ser Ser Glu Ser Lys Arg Glu Thr Glu Tyr Gly
305             310             315             320

Pro Cys Arg Arg Glu Met Glu Asp Thr Leu Asn His Leu Lys Phe Leu
            325             330             335

Asn Val Leu Ser Pro Arg Gly Val His Ile Pro Asn Cys Asp Lys Lys
            340             345             350

Gly Phe Tyr Lys Lys Lys Gln Cys Arg Pro Ser Lys Gly Arg Lys Arg
            355             360             365

Gly Phe Cys Trp Cys Val Asp Lys Tyr Gly Gln Pro Leu Pro Gly Tyr
            370             375             380

Thr Thr Lys Gly Lys Glu Asp Val His Cys Tyr Ser Met Gln Ser Lys
385             390             395             400

Val Glu Cys Pro Pro Cys Pro Ala Pro Pro Val Ala Gly Pro Ser Val
            405             410             415

Phe Leu Phe Pro Pro Lys Pro Lys Asp Gln Leu Met Ile Ser Arg Thr
            420             425             430

Pro Glu Val Thr Cys Val Val Val Asp Val Ser His Glu Asp Pro Glu
            435             440             445

Val Lys Phe Asn Trp Tyr Val Asp Gly Val Glu Val His Asn Ala Lys
            450             455             460

Thr Lys Pro Arg Glu Glu Gln Tyr Asn Ser Thr Tyr Arg Val Val Ser
465             470             475             480

Val Leu Thr Val Leu His Gln Asp Trp Leu Asn Gly Lys Glu Tyr Lys
            485             490             495

Cys Lys Val Ser Asn Lys Gly Leu Pro Ser Ser Ile Glu Lys Thr Ile
            500             505             510

Ser Lys Ala Lys Gly Gln Pro Arg Glu Pro Gln Val Tyr Thr Leu Pro
            515             520             525
```

```
Pro Ser Arg Glu Glu Met Thr Lys Asn Gln Val Ser Leu Thr Cys Leu
    530                 535                 540

Val Lys Gly Phe Tyr Pro Ser Asp Ile Ala Val Glu Trp Glu Ser Asn
545                 550                 555                 560

Gly Gln Pro Glu Asn Asn Tyr Lys Thr Thr Pro Pro Val Leu Asp Ser
                565                 570                 575

Asp Gly Ser Phe Phe Leu Tyr Ser Lys Leu Thr Val Asp Lys Ser Arg
            580                 585                 590

Trp Gln Gln Gly Asn Val Phe Ser Cys Ser Val Met His Glu Gly Leu
            595                 600                 605

His Asn His Tyr Thr Gln Lys Ser Leu Ser Leu Ser Pro Gly Lys
    610                 615                 620
```

<210> SEQ ID NO 32
<211> LENGTH: 395
<212> TYPE: PRT
<213> ORGANISM: Artificial Sequence
<220> FEATURE:
<223> OTHER INFORMATION: Synthesized

<400> SEQUENCE: 32

```
Met Ser Glu Val Pro Val Ala Arg Val Trp Leu Val Leu Leu Leu Leu
1               5                   10                  15

Thr Val Gln Val Gly Val Thr Ala Gly Ala Ala Ser Gly Gly Gly
            20                  25                  30

Ser Gly Gly Gly Gly Ser Gly Gly Gly Gly Ser Gly Gly Gly Gly Asp
            35                  40                  45

Pro Ile Val Tyr Glu Ile His Pro Thr Lys Ser Phe Ile Ser Thr Trp
50                  55                  60

Trp Lys Glu Pro Leu Asn Ile Val Ser Phe Leu Phe Cys Phe Ala Ser
65                  70                  75                  80

Gly Gly Ser Thr Ile Thr Gly Val Gly Lys Asn Leu Asn Ser Val Ser
            85                  90                  95

Val Pro Arg Met Val Ile Asn Val His Glu Ala Gly Arg Asn Phe Thr
            100                 105                 110

Val Ala Cys Gln His Arg Ser Asn Ser Glu Ile Ile Cys Cys Thr Thr
        115                 120                 125

Pro Ser Leu Gln Gln Leu Asn Leu Gln Leu Pro Leu Lys Thr Lys Ala
    130                 135                 140

Phe Phe Met Leu Asp Gly Ile Leu Ser Lys Tyr Phe Asp Leu Ile Tyr
145                 150                 155                 160

Val His Ser Gly Gly Ser Gly Gly Gly Thr Gly Val Glu Cys Pro
            165                 170                 175

Pro Cys Pro Ala Pro Pro Val Ala Gly Pro Ser Val Phe Leu Phe Pro
            180                 185                 190

Pro Lys Pro Lys Asp Gln Leu Met Ile Ser Arg Thr Pro Glu Val Thr
        195                 200                 205

Cys Val Val Val Asp Val Ser His Glu Asp Pro Glu Val Lys Phe Asn
    210                 215                 220

Trp Tyr Val Asp Gly Val Glu Val His Asn Ala Lys Thr Lys Pro Arg
225                 230                 235                 240

Glu Glu Gln Tyr Asn Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270
```

-continued

```
Asn Lys Gly Leu Pro Ser Ser Ile Glu Lys Thr Ile Ser Lys Ala Lys
        275                 280                 285

Gly Gln Pro Arg Glu Pro Gln Val Tyr Thr Leu Pro Pro Ser Arg Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Gly Leu His Asn His Tyr
    370                 375                 380

Thr Gln Lys Ser Leu Ser Leu Ser Pro Gly Lys
385                 390                 395
```

RECOMBINANT PROTEINS AND USES THEREOF

CROSS-REFERENCE TO RELATED APPLICATION

This application relates to and claims the benefit of U.S. Provisional Application No. 62/454,902, filed Feb. 6, 2017, the disclosure of the application is incorporated herein by reference in its entirety.

SEQUENCE LISTING

The present application is being filed along with a Sequence Listing in electronic format. The Sequence Listing is provided as a file entitled 2019-08-02-SequenceListing.txt, created Aug. 2, 2019, which is 138 Kb in size. The information in the electronic format of the Sequence Listing is incorporated herein by reference in its entirety.

BACKGROUND OF THE INVENTION

1. Field of the Invention

The present disclosure relates to recombinant proteins. More particularly, the disclosed invention relates to recombinant proteins containing the insulin-like growth factor-binding protein-3 (IGFBP3) and an IgG Fc portion.

2. Description of Related Art

The IGF pathway is also regulated by a family of six insulin-like growth factor-binding proteins (IGFBPs) (1). All six IGFBP family members bind IGF-1 and IGF-2 and share a structure of a highly conserved, disulfide-bonded N-terminal and C-terminal domain linked by a non-conserved linker domain. Both the N- and C-terminal domains participate in IGF binding, which is controlled by proteolysis of the middle linker domain (2, 3). By binding with IGF-1 and IGF-2, IGFBPs play an important role in regulating proliferation. The binding affinity of IGFBPs toward IGFs is higher than the binding affinity between IGFs and IGF receptors, and IGFs bound with IGFBPs will only be released after being cleaved by proteases (4). The proteolysis is regulated, and the concentrations of active proteases are increased in conditions such as pregnancy, wound healing, and cancer. Accordingly, the sequestration of IGF can result in the inhibition of the cellular proliferation and the stimulation of the apoptosis, while the release of IGFs from IGFBPs after the proteolysis can result in increased proliferation. Overexpression of IGFBP-3 in transgenic mice results in physical and metabolic changes, but notably transgenic animals are healthy and fertile (5) (6), (7).

IGFBPs also exhibit an IGF-1 independent inhibition of the proliferation or induction of apoptosis (8). For example, IGFBP3 inhibits the growth of fibroblasts that lack the IGF-1 receptor. Further, some mutated IGFBPs that cannot bind with IGFs still exhibit anti-proliferative effects. Because of the complexity associated with the regulation of IGFBPs, there is no clear consensus between IGFBP expression levels and cancer incidence, disease severity, or prognostic survival.

The insulin-like growth factor (IGF) system has been implicated in the carcinogenesis and tumor progression of various cell types. Many cancers have been shown to overexpress the IGF-1 receptor and/or its ligands (IGF-1 and IGF-2). Multiple groups have suggested the use of IGFBP-3 in cancer. therapy (9, 10, 11).

The understanding of proliferation pathways has led to the development of many successful targeted therapies for cancer (12, 13, 14). These targeted therapies can cause remarkable cancer regression with milder side effects, compared to those associated with the standard chemotherapy. However, resistance to the drug used in the targeted therapy frequently develops because of mutations in the target itself or mutations in another pathway that circumvents the drug's target. Growth factors fuel bypass signaling pathways and can rescue cancer cells from targeted therapies (15) and conversely, resistant cancer cells often exhibit growth factor pathway activation (16, 17). The origin of these growth factors can be from the tumor or the stroma surrounding the tumor. Resistance to the BRAF tyrosine kinase inhibitor (TKI) vemurafenib has been linked to the up-regulation of epidermal growth factor and IGF-1 and the down-regulation of insulin-like growth factor-binding proteins (IGFBPs) (18) (19).

Double or triple combinations of targeted therapeutics and cytotoxic agents should improve the efficacy of therapy, as well as postpone the occurrence of the resistance (20). In addition, single tumors have been shown to be heterogeneous, and hence, multiple targeted therapies may exhibit increased efficacy by attacking a broader spectrum of tumor cells that may be unrepresented from single biopsy specimens (21).

Despite the efforts of many researchers in the related art, novel therapeutics and methods are still being sought to combat cancer, in particular those resistant to targeted therapies.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

Briefly, the present disclosure provides several recombinant proteins that comprise an insulin-like growth factor-binding protein-3 (IGFBP3) or a biologically active fragment thereof. The present recombinant proteins are advantageous in that they not only retain the binding affinity toward the insulin-like growth factor, but also bind with various growth factors in the nanomolar range. This multiple-targeting effect translates into a more effective cancer therapy that might broaden the therapeutic efficacy and postpone the development of resistance. According to aspects of the present disclosure, these recombinant proteins can be administered alone or in combination with existing treatments to treat cancer.

In one aspect, the present disclosure is directed to a recombinant IGFBP3 protein.

According to one embodiment of the present disclosure, the recombinant IGFBP3 comprises an IGFBP3 variant and an IgG Fc portion that is linked to the C-terminus of the IGFBP3 variant.

According to certain optional embodiments of the present disclosure, the IGFBP3 variant comprises one or more mutations to amino acid residues 114 to 185 of SEQ ID NO: 1, wherein the mutation confers an increased potency of the IGFBP3 variant in binding at least one first growth factor, as compared with the wild-type IGFBP3. In some embodiments, the mutation comprises one or more of the following, the deletion of amino acid residues 121 to 126 of SEQ ID NO: 1, the deletion of amino acid residues 166 to 174 of SEQ ID NO: 1, and the deletion of amino acid residues 180 to 185 of SEQ ID NO: 1. According to some embodiments of the present disclosure, the IGFBP3 variant comprises amino acid residues 175 to 179 and/or 134 to 136 of SEQ ID NO: 1. Some examples of the IGFBP3 variant according to the present disclosure include those having the sequence of SEQ ID NO: 2, 5 or 6.

According to some optional embodiments of the present disclosure, the first growth factor is a vascular endothelial growth factor B (VEGF-B), neuregulin, platelet-derived growth factor (PDGF), hepatocyte growth factor (HGF), or basic fibroblast growth factor (bFGF).

In optional embodiments of the present disclosure, the recombinant IGFBP3 further comprises a binding domain specific for a second growth factor, wherein the binding domain is linked to the N-terminus of the IGFBP3 variant or between the IGFBP3 variant and the IgG Fc portion. For example, the binding domain may be one specific for VEGF, neuregulin, PDGF, HGF, bFGF, or HB-EGF. According to various embodiments, the first growth factor and the second growth factor may be the same growth factor or different growth factors. According to some optional embodiments of the present disclosure, the second growth factor is VEGF. In certain embodiments, the VEGF binding domain is linked to the N-terminus of the IGFBP3 variant. Alternatively, in other embodiments, the VEGF binding domain is linked to the C-terminus of the IGFBP3 variant, and the IgG Fc portion linked to the C-terminus of the VEGF binding domain. Still alternatively, the VEGF binding domain is linked to the C-terminal of the Fc domain, according to other optional embodiments. According to certain embodiments of the present disclosure, the VEGF binding domain is VEGF receptor 1 domain 2 or VEGF receptor 2 domain 3. In one embodiment, the VEGF binding domain comprises both the VEGF receptor 1 domain 2 and VEGF receptor 2 domain 3.

In some optional embodiments, the recombinant IGFBP3 further comprises a linker that is inserted between the IGFBP3 variant and the VEGF binding domain. For example, the linker comprises an amino acid sequence having the sequence of SEQ ID NO: 13.

Still optionally, the second growth factor is neuregulin. In certain cases, the binding domain of neuregulin receptor is linked to the N-terminus of the IGFBP3 variant; alternatively, the neuregulin binding domain is inserted between to the C-terminus of the IGFBP3 variant and the IgG Fc portion. According to certain embodiments of the present disclosure, the neuregulin binding domain is a receptor tyrosine-protein kinase ErbB4 domain 1.

In some embodiments where the recombinant IGFBP3 comprises both the VEGF binding domain and the ErbB4 domain 1 (i.e., the recombinant IGFBP3-FC-VEGF-ErbB4 protein), it comprises, from the N-terminus to the C-terminus, the ErbB4 domain 1, the IGFBP3 variant, the linker, the VEGF binding domain, and the IgG Fc portion.

According to optional embodiments of the present disclosure, the recombinant IGFBP3 is a dimeric fusion protein.

In some other optional embodiments, the recombinant IGFBP3 is PEGylated.

In yet another aspect, the present disclosure is directed to a method for treating tumor.

According to certain embodiments, the method comprises the step of administering to a subject in need thereof an effective amount of a recombinant IGFBP3 protein according to any of the above-mentioned aspect/embodiments.

In still another aspect, the present disclosure is directed to a method for treating tumor to prevent or postpone resistance to a targeted therapy.

According to certain embodiments, the method comprises the steps of administering to a subject in need thereof an effective amount of a recombinant IGFBP3 protein according to any of the above-mentioned aspect/embodiments, and administering to the subject an effective amount of a targeted therapy agent.

According to various optional embodiments of the present disclosure, the target therapy agent is erlotinib, vemurafenib, afatinib, crizotinib, osimertinib or sorafenib.

In some optional embodiments, the tumor is hepatocellular carcinoma, lung carcinoma or colon cancer.

In yet another aspect, the present disclosure is directed to a method for treating tumor to enhance effects of chemotherapy.

According to certain embodiments, the method comprises the steps of administering to a subject in need thereof an effective amount of a recombinant IGFBP3 protein according to any of the above-mentioned aspect/embodiments, and administering to the subject an effective amount of a chemotherapy agent.

According to various optional embodiments of the present disclosure, the target therapy agent is gemcitabine, cisplatin, or doxorubicin.

In some optional embodiments, the tumor is hepatocellular carcinoma, lung cancer or colon cancer.

In yet still another aspect, the present disclosure is directed to a method for treating wet age-related macular degeneration (wet AMD) or diabetic retinopathy.

According to certain embodiments, the method comprises the step of administering to a subject in need thereof an effective amount of a recombinant IGFBP3 protein according to any of the above-mentioned aspect/embodiments.

Subject matters that are also included in other aspects of the present disclosure include the use of the present recombinant IGFBP3 protein in the manufacture of a medicament for use in the treatment of tumor (including tumor that is resistant to the targeted therapy or chemotherapy) or wet AMD, as well as the present recombinant IGFBP3 protein for use in the treatment of the above-mentioned diseases.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 18A provides experimental results showing the effect of the chimera D3 on the proliferation of A549 cells treated with AZD9291 or trametinib;

FIG. 18B provides experimental results showing the effect of the chimera D3 on the proliferation of A549 cells treated with cisplatin;

DESCRIPTION

Figure 1:
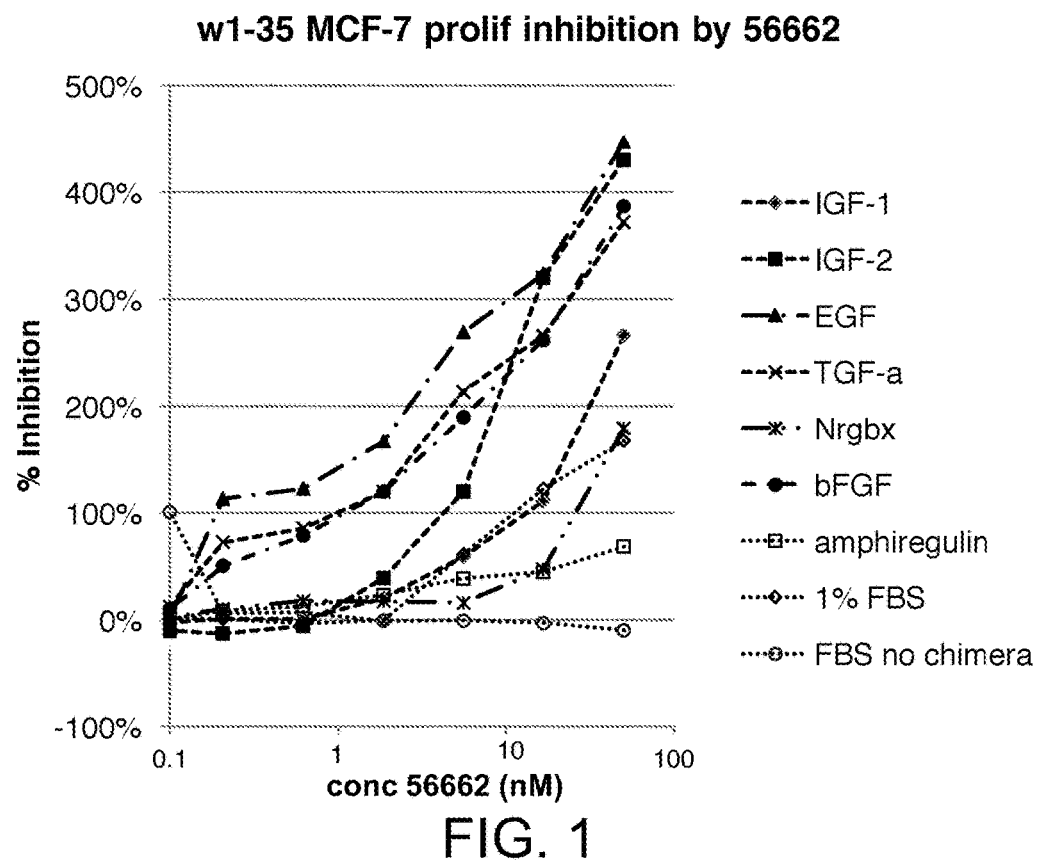
FIG. 1 is a line graph illustrating the effect of 56662 (BP3/Fc) on the proliferation of MCF-7 breast cancer cells in the presence of various growth factors.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

Throughout the present disclosure, some acronyms are used when describing the recombinant proteins to facilitate the understanding of the present invention. However, as could be appreciated, the elements comprised in the acronyms are only used to denote the domain/region present in the recombinant proteins under discussion, and the order in which the elements are recited in the acronym does not imply the structural relationship of the elements. For example, an acronym of a recombinant X-Y-Z protein does not mean that the X, Y, and Z domains/regions are arranged from the N-terminus to the C-terminus in the order of X-Y-Z. Accordingly, these acronyms should not be construed as a limitation to the present invention.

The term "potency" is generally used to refer to relative affinities or efficacies. An IGFBP3 variant has an increased or a higher potency if it exhibits a higher binding efficacy than the wild-type IGFP3 when the two are compared at the same molar concentration, or if it produces the same effect at a lower concentration.

The term "linked," as used herein, refers to the joining or connecting of two or more elements (e.g., amino acid sequences). The term "linked" may mean directly fused by a peptide bond, indirectly fused with a spacer, as well as hooked together by means other than a peptide bond, e.g., through disulfide bonds or a non-peptide moiety. For example, a first amino acid sequence and a second amino acid sequence may be directly linked with each other without other intervening sequences. Alternatively, the first and second amino acid sequences may be indirectly linked with one or more amino acid sequences being inserted therebetween.

As used herein, the term "binding domain" is referred to a domain of a polypeptide (or a portion of said domain) that specifically binds to/interacts with a given target. For example, said binding domain is able to specifically bind and/or interact with a growth factor that could be the target of clinical medicine.

The term "Fc portion" or "Fc domain" refers to a C-terminal non-antigen binding region of an immunoglobulin heavy chain that contains at least a portion of the constant region. Also, the term "dimeric fusion protein" refers to a homodimer that comprises two recombinant IGFBP3 fusion proteins in which the two heavy chains are held together by disulfide bonds.

"Percentage (%) amino acid sequence identity" with respect to the amino acid sequences identified herein is defined as the percentage of amino acid residues in a candidate sequence that are identical with the amino acid residues in the specific amino acid sequence (i.e., the subject sequence), after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by National Center for Biotechnology Information (NCBI). The percentage amino acid sequence identity of a given amino acid sequence A to a subject amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in the subject amino acid sequence B.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present recombinant protein or a pharmaceutical composition comprising the same to a subject, who has a medical condition associated a particular disease (e.g., tumor), a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present recombinant protein that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, as the total mass of ester prodrug (e.g., in grams, milligrams or micrograms) or a ratio of mass of ester prodrug to body mass, e.g., as milligrams per kilogram (mg/kg).

The terms "application" and "administration" are used interchangeably herein to mean the application of a recombinant protein or a pharmaceutical composition of the present invention to a subject.

The terms "subject" and "patient" are used interchangeably herein and are intended to mean an animal including the human species that is treatable by the recombinant protein, pharmaceutical composition and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

As used herein, a "pharmaceutically acceptable" component is one that is suitable for use with humans and/or animals without undue adverse side effects (such as toxicity, irritation, and allergic response) commensurate with a reasonable benefit/risk ratio. In a specific embodiment, the term "pharmaceutically acceptable" means approved by a regulatory agency or other generally recognized pharmacopoeia for use in animals, and more particularly in humans. Each component must be "acceptable" in the sense of being compatible with the other ingredients of the formulation.

The term "carrier" refers to a diluent, adjuvant, excipient, or vehicle with which the therapeutic is administered. The carrier can be in the form of a solid, semi-solid or liquid diluent, cream or a capsule. These pharmaceutical preparations are a further object of the invention.

The present invention is based, at least, on the finding that some IGFBP3 variants can bind multiple growth factors in addition to insulin-like growth factors 1 and II (IGF-1 and IGF-2). For example, the experimental data provided herein established that the IGFBP3 variant binds the neuregulin, platelet-derived growth factor (PDGF), hepatocyte growth factor (HGF), vascular endothelial cell growth factor-B (VEGF-B), and/or basic fibroblast growth factor (bFGF) with a nanomolar affinity. In addition to growth factors, the IGFBP3 variant also binds with chemokines like Regulated upon Activation Normal T cell Express Sequence (RANTES), which is also a target in cancer therapy. Recombinant proteins having the IGFBP3 variant have been constructed by the present inventor to improve the physical properties and expand growth factor binding and inhibition capabilities. Notably, the present recombinant proteins inhibit the proliferation, angiogenesis and/or metastasis of tumor cells.

Briefly, the present disclosure provides several recombinant proteins that comprise an IGFBP3 variant. The present recombinant proteins are advantageous in that they not only retain the binding affinity toward the insulin-like growth factor, but also bind with multiple growth factors in the nanomolar range. This multiple-targeting effect translates into a more effective cancer therapy that might broaden the therapeutic efficacy and postpone the development of resistance. Another advantage of the present disclosure lies in that the IGFBP3 variant may be used as a platform, to which one or more binding domains may be attached, thereby resulting a recombinant IGFBP3 with versatile binding capabilities. According to aspects of the present disclosure, these recombinant proteins can be administered alone or in combination with existing treatments to treat cancer.

In one aspect, the present disclosure is directed to a recombinant insulin-like growth factor-binding protein-3 (IGFBP3) protein.

According to one embodiment of the present disclosure, the recombinant IGFBP3 comprises an IGFBP3 variant and an IgG Fc portion linked to the C-terminus of the IGFBP3 variant.

As could be appreciated, in some embodiments, the recombinant IGFBP3 may be a single chain polypeptide (that is, a monomeric Fc fusion protein), while in other embodiments, the recombinant IGFBP3 may be a dimeric fusion protein consisting of two monomeric Fc fusion proteins bridged by disulfide bonds.

To enhance the serum half-life of the present recombinant IGFBP3, it may be optionally PEGylated, according to some embodiments of the present disclosure.

According to the inventive concept of the present disclosure, the present IGFBP3 variant may be designed to retain, or optionally to improve, its binding affinity toward IGFs, while reducing its susceptibility of the recombinant IGFBP3 protein to proteolysis and/or increasing its potency in binding one or more growth factors other than IGFs, such as neuregulin, PDGF, HGF, VEGF-B, and bFGF. According to some working examples provided herein, the IGFBP3 variant comprises one or more mutations to amino acid residues 114 to 185 of SEQ ID NO: 1, wherein the mutation confers an increased potency of the IGFBP3 variant in binding at least one first growth factor, as compared with the wild-type IGFBP3. For example, the mutation may be one or more of the following, the deletion of amino acid residues 121 to 126 of SEQ ID NO: 1, the deletion of amino acid residues 166 to 174 of SEQ ID NO: 1, and the deletion of amino acid residues 180 to 185 of SEQ ID NO: 1. According to some embodiments of the present disclosure, the IGFBP3 variant comprises amino acid residues 175 to 179 and/or 134 to 136 of SEQ ID NO: 1. Some examples of the IGFBP3 variant according to the present disclosure include those having the sequence of SEQ ID NO: 2, 5 or 6.

According to various embodiments of the present disclosure, the recombinant IGFBP3 comprising the IGFBP3 variant and the Fc region (i.e., the recombinant IGFBP3-Fc protein) may have the sequence of sequence of SEQ ID NO: 8, 11, or 12.

The recombinant IGFBP3 may further comprise the binding domain specific for a wide variety of growth factors so as to improve the binding efficacy of the recombinant IGFBP3 toward said growth factor(s). As discussed above, the IGFBP3 variant is designed to have an increased potency in binding at least one additional growth factors, and the incorporation of an additional binding domain specific for the same growth factor may further improve its binding efficacy toward said growth factor; on the other hand, the incorporation of an additional binding domain specific for a different growth factor may expand its binding versatility. This additional binding domain may be attached to the N- or C-terminus of the IGFBP3 variant. Examples of the binding domain suitable for used herein include, but are not limited to the binding domain specific for the VEGF, neuregulin, PDGF, HGF, bFGF, or HB-EGF. For example, the binding domain specific for HB-EGF may include the binding domain derived from human epidermal growth factor receptor 1 (Her1, also known as ErbB1). On the other hand, the binding domain specific for neuregulin may include the binding domain derived from ErbB3 or ErbB4.

According to some optional embodiments of the present disclosure, the recombinant IGFBP3 further comprises a VEGF binding domain (that is, a recombinant IGFBP3-Fc-VEGF protein). By incorporating a VEGF binding domain, the binding affinity of the recombinant IGFBP3 toward VEGF-B is further increased and binding to VEGF-A and PlGF is created. This VEGF binding domain may target the tumor stroma by inhibiting vascularization.

According to embodiments of the present disclosure, the VEGF binding domain is a high affinity VEGF binding domain, such as VEGF receptor 1 (VEGFR-1) domain 2 or VEGF receptor 2 (VEGFR-2) domain 3. In one embodiment, the VEGF binding domain comprises both the VEGFR-1 domain 2 and the VEGFR-2 domain 3.

In certain embodiments, the VEGF binding domain is linked to the N-terminus of the IGFBP3 variant. Alternatively, in other embodiments, the VEGF binding domain is linked to the C-terminus of the IGFBP3 variant, and the IgG Fc portion is linked to the C-terminus of the VEGF binding domain; i.e., the VEGF binding domain is inserted between the IGFBP3 variant and the IgG Fc portion. In other alternative embodiments, the VEGF binding domain is linked to the C-terminal of the Fc domain.

According to various embodiments, the VEGF binding domain may link directly with the IGFBP3 variant, or indirectly with a linker interposed therebetween. Therefore, in some optional embodiments, the recombinant IGFBP3 protein further comprises a linker that is inserted between the IGFBP3 variant and the VEGF binding domain. For example, the linker may be a short peptide (e.g., 10 to 30 a.a.) selected from the non-conserved middle linker domain of IGFBP3 and include an N-glycosylation site. One example of such linker is an 18-a.a. short peptide having the sequence of SEQ ID NO: 13.

According to various embodiments of the present disclosure, the recombinant IGFBP3-Fc-VEGF protein has the sequence of SEQ ID NO: 14, 17, or 18.

Still optionally, the recombinant IGFBP3 further comprises an ErbB4 domain 1 (aka, a recombinant IGFBP3-Fc-VEGF-ErbB4 protein) according to some embodiments. In certain cases, the ErbB4 domain 1 is linked to the N-terminus of the IGFBP3 variant; alternatively, the ErbB4 domain 1 is inserted between to the C-terminus of the IGFBP3 variant and the IgG Fc portion.

In some embodiments, the recombinant IGFBP3-FC-VEGF-ErbB4 protein comprises, from the N-terminus to the C-terminus, the ErbB4 domain 1, the IGFBP3 variant, the linker, the VEGF binding domain, and the IgG Fc portion. For example, the recombinant IGFBP3-Fc-VEGF-ErbB4 protein has the sequence of SEQ ID NO: 20.

In yet another aspect, the present disclosure is directed to a method for treating tumor. The present disclosure is further advantageous in that the recombinant IGFBP3 is effective for treating tumor that is resistant to a targeted therapy or chemotherapy; in particular the resistance caused by the bFGF, HGF, IGF, neuregulin or PDGF activation of its receptor. It is also expected that the present method may prolong the duration of response.

According to certain embodiments, the method comprises the step of administering to a subject in need thereof an effective amount of a recombinant IGFBP3 protein according to any of the above-mentioned aspect/embodiments.

According to various embodiments of the present disclosure, the recombinant IGFBP3 protein is administered to a mouse in a dose of about 0.1 mg/kg to 1,000 mg/kg; preferable, about 1 mg/kg to 100 mg/kg, when used alone or in combination with one or more therapeutic agent (such as a targeted therapy agent or a chemotherapy agent). Specifically, the effective dose for mice may be about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1,000 mg/kg.

In the embodiments where the subject is a human, the effective dose may be determined using the "Guidance for Industry—Estimating the Maximum Safe Starting Dose in Initial Clinical Trials for Therapeutics in Adult Healthy Volunteers" p proposed by the Food and Drug Administration (FDA) of U.S. Department of Health and Human Services. For example, one may convert the mice dose into a human equivalent dose (HED) by multiply the mice dose with 0.081. According to embodiments of the present disclosure, the recombinant IGFBP3 protein is administered to an adult human in a dose of about 0.01 mg/kg to 1,000 mg/kg; preferable, about 0.1 mg/kg to 100 mg/kg, when used alone or in combination with one or more therapeutic agent (such as a targeted therapy agent or a chemotherapy agent). Specifically, the effective dose for an adult human may be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1,000 mg/kg. The dose for children may be half or one-fourth of the adult human dose specified above.

In some embodiments, the recombinant IGFBP3 protein may be provided in a pharmaceutical composition, which comprises an effective amount of the recombinant IGFBP3 protein and a pharmaceutically acceptable carrier. Usually, the amount of the active compound (i.e., the recombinant IGFBP3 protein) is between 0.1-95% by weight of the composition, preferably between 0.2-20% by weight in preparations for parenteral use and preferably between 1 and 50% by weight in preparations for oral administration. For the clinical use of the methods of the present invention, the pharmaceutical composition of the invention is formulated into dosage forms suitable for the intended route of administration.

According to certain embodiments, the method for treating tumor or tumor that is resistant to a targeted therapy or chemotherapy further comprises the step of administering to the subject in need thereof an effective amount of a targeted therapy agent or a chemotherapy agent. As could be appreciated, the present recombinant IGFBP3 (or the pharmaceutical composition comprising the same) may be administered to the subject before, concurrently with, or after the administration of the targeted therapy agent or chemotherapy agent.

According to various optional embodiments of the present disclosure, the target therapy agent is erlotinib, osimertinib (AZD9291), vemurafenib, afatinib, trametinib, or sorafenib. Also, the chemotherapy agents can be, but are not limited to, gemcitabine, cisplatin and doxorubicin.

In some optional embodiments, the tumor is hepatocellular carcinoma, lung cancer or colon cancer.

In yet still another aspect, the present disclosure is directed to a method for treating wet age-related macular degeneration (wet AMD) or diabetic retinopathy. According to certain embodiments, the method comprises the step of administering to a subject in need thereof an effective amount of a recombinant IGFBP3 protein according to any of the above-mentioned aspect/embodiments (or a pharmaceutical composition comprising the same).

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLES

Materials and Methods

Growth factors, IGFBPs, and antibodies were purchased from R&D Sciences or SinoBiologicals. Secondary antibodies were purchased from Jackson Immunoresearch. Biotinylated IGF-1 was obtained from GroPep (Australia).

Chimera Construction and Protein Expression

Genes, based on human protein sequence, were synthesized by DNA2.0 and the sequence optimized for human codon usage. The DNA was then cloned into a DNA2.0 proprietary mammalian expression vector pJ603. The expression vector was then transfected into a production host. Culturing of the resulting transfectant yields the dimeric fusion protein as a secreted product that was then harvested and purified by with Protein-A Sepharose all in general accordance with established practice.

Table 1 below summarizes the elements (e.g., domains/regions and linkers) comprised in each recombinant protein (i.e., chimera).

TABLE 1

| Name | Structure (from N-terminus to C-terminus) | SEQ ID NO. |
|---|---|---|
| IGFBP3-Fc (56662 or BP3) | IGFBP3-Fc | 7 |
| IGFBP3-Fc-1 (h3t33fc) | IGFBP3 with IGFBP3 linker deletion 1-Fc | 8 |
| IGFBP3/4-del-Fc (105795) | IGFBP3 with IGFBP4 linker deletion-Fc | 9 |
| IGFBP3/6-Fc (68260) | IGFBP3 with IGFBP6 linker-Fc | 10 |
| IGFBP3-Fc-2 (3(del2)3) | IGFBP3 with IGFBP3 linker deletion 2-Fc | 11 |
| IGFBP3-Fc-3 (3(del3)3 or chimera D3) | IGFBP3 with IGFBP3 linker deletion 3-Fc | 12 |
| IGFBP3-Fc-VEGF-1 (chimera A) | IGFBP3 with IGFBP3 linker deletion 1-gly 3 linker-v1v2-Fc | 14 |
| IGFBP3/4-del-Fc-VEGF (chimera D) | IGFBP3 with IGFBP4 linker deletion-gly 3 linker-v1v2-Fc | 15 |
| IGFBP3/6-Fc-VEGF (80716) | IGFBP3 with IGFBP6 linker-gly 6 linker-v1v2-Fc | 16 |
| IGFBP3-Fc-VEGF-2 (D2V1V2Fc) | IGFBP3 with IGFBP3 linker deletion 2-gly 3 linker-v1v2-Fc | 17 |
| IGFBP3-Fc-VEGF-3 (3(del3)3V1V2) | IGFBP3 with IGFBP3 linker deletion 3-gly 3 linker-v1v2-Fc | 18 |
| IGFBP3-GS16-VEGF-Fc (Chimera B or 3-t3-3-GS16-V1V2) | IGFBP3 with IGFBP3 linker deletion 1-GS 16 linker-v1v2-Fc | 19 |
| IGFBP3-Fc-VEGF-ErbB4 (ErbB4-BP3-VEGF-trap) | ErbB4-GS-IGFBP3-gly 3 linker-v1v2-Fc | 20 |
| IGFBP3-Fc-VEGF (BP3-VEGF-trap) | IGFBP3-gly 3 linker-v1v2-Fc | 21 |
| IGFBP3-Fc-ErbB4 | ErbB4-GS-IGFBP3-gly 3 linker-Fc | 22 |

293T Cells Transfection

Plasmids were produced in E. coli. and purified with NucleoBond Xtra Midi Plus Kit (Machevey-Nagel). 293T cells were transfected using Mirus Transit per the manufacturer's protocol. After 24 hours, medium was changed to opti-MEM containing 0.5% FBS, 2 mM valproic acid, and 50 ng/ml longR3-IGF-1. Other additives such as heparin may increase yield of some IGFBP3 variants. Conditioned medium was harvested every 2 days. Concentrated conditional medium was purified by proteinA Sepharose and elution with 0.1 M glycine, pH 3 or 5 M guanidinium chloride in PBS. In general, purified chimera was diafiltered against buffer (PBS, PBS with 0.5-1.0 M NaCl, 50 mM succinate, 50 mM succinate with 0.5-1.0 M NaCl) adjusted to at least 1 pH unit lower than the isoelectric point of the chimera before use. Chimeras were analyzed on a Superdex equilibrated in 50 mM sodium succinate in 1 M NaCl (pH 6.0) to assess aggregation.

Fc ELISA Assay

Grenier high binding ELISA plates were coated with 1 ug/ml goat anti-human Fc antibody (Jackson Immunoresearch) in PBS overnight, and then blocked with Assay Buffer (Invitrogen). Plates were incubated for 2 hours with Chimera or human Fc (Jackson Immunoresearch) as standard; followed by HRP-conjugated anti-human Fc antibody (Jackson Immunoresearch) for 60 minutes. HRP substrate, tetramethyl benzidine, was added; the reaction was stopped with 2 N H2SO4, and then the plate was read at 450 nm.

IGF-1/VEGF Binding Assay

Plates were coated with goat anti-human Fc antibody, blocked and then incubated with chimera as in the Fc ELISA. Biotinylated IGF-1 (GroPep) or VEGF-Biotin (R&D Systems VEGF biotinylated with sulfo-NHS-LC-biotin as per instructions (Pierce) was added for 2 hours followed by streptavidin-HRP (Jackson Immunoresearch) for 30 minutes. Chromogenic development with tetramethyl benzidine was performed as described above.

Growth Factor ELISA Assay

ELISA plates were coated with 0.5 µg/ml growth factor (IGF-1, IGF-2, VEGF, etc.) in PBS overnight and blocked as described above. After overnight incubation with chimera, chimera binding was detected with anti-human Fc-HRP and development with tetramethyl benzidine as described above.

Proliferation Assays

MCF-7 cells (a breast cancer cell line) were maintained in MEM (GIBCO) plus insulin and NEAA and 10% FBS (Hyclone). MDA-MB-231 cells (a breast cancer cell line) were maintained in DMEM (GIBCO) with 10% FBS, Hep3B cells (a liver cancer cell line) were maintained in MEM (GIBCO) with 10% FBS; BXPC-3 (a pancreatic carcinoma cell line) were maintained in RPMI (GIBCO) plus NEAA, 10% FBS; HT29 (a colorectal carcinoma) or NIH3T3 cells were maintained in McCoy's 5A (GIBCO) plus 10% FBS; HUVEC cells were maintained in endothelial cell medium (ScienCell); other cell lines, including hep3B, Huh-7 (a liver cancer cell line), PC-9 (a lung carcinoma cell line), A549 (a lung carcinoma cell line), A431 (a squamous carcinoma cell line) and H1975 (a T790M NSCLC cell line), were maintained as suggested by the American Type Culture Collection.

For the proliferation assay, cells except for HUVEC were seeded at a density of 1,000 to 6,000 in 96 wells in an assay buffer of DMEM/F12 plus 0.2% BSA and 10 ug/ml transferrin. Chemical inhibitors were added after 16-20 hours after plating; IGF-1 or other growth factors or test chimeras in assay buffer were added at the time of plating or 16-20 hours after plating. 5,000 HUVEC ells were plated in poly-L-lysine coated 96 wells in M199 with 1%/FBS and HEPES. After 3 to 4 days of culture, growth was determined by incubating cells with Alamar blue for 4 to 6 hours and then the fluorescence (RFU) at 544/590 nm was read. For long term proliferation assays, cells were plated in the growth media with 5% or 10% FBS at densities of 500 to 10,000 cells per cm² growth area and grown for 7 to 21 days. Inhibitors and effectors were added 1-4 days after plating. Cells were exposed to cisplatin or gemcitabine for two days. Medium was renewed twice weekly. At completion, cells were fixed and then stained with Giemsa.

Biacore Binding

Biacore binding was performed at David Myszka's laboratory at the University of Utah or at the Genomic Research Center at Academia Sinica. Surfaces of binding protein chimera were made via chemical immobilization on a CM4 chip using standard amine coupling chemistry. Some growth factors showed high background binding to control surfaces and were immobilized to CM4 chips, and experiments using growth factor as ligand is noted. Excess surface carboxyl activated sites on all four flow cells was blocked using the doubly positively charged species ethylenediamine. Binding experiments (but not immobilizations) in HBS-P (10 mM HEPES pH 7.4, 150 mM NaCl, 0.05% P20), The HBS-P was supplemented with BSA at 0.2 mg/mL, or HBS-P was supplemented with 500 mM NaCl (650 mM NaCl, final concentration). Analytes were also reconstituted in the corresponding buffer. All experiments were performed at 25° C. 1/150 dilutions of phosphoric acid were used to regenerate IGFBP3-Fc surfaces and a sequence of 3 M $MgCl_2$ followed by 5 M GuCl was used to regenerate surfaces immobilized with growth factor. Dissociation constants reported below used immobilized binding protein unless noted. Differences between binding constants may be expected between growth factor immobilization and chimera immobilization.

Pharmacokinetic Assay

Mice were injected subcutaneously with 100 ug chimera 56662 (4 mg/kg). Two mice per group were used. Serum samples were taken at 0, 4, 24, 48, 72 hours after injection. The concentration of 56662 in serum was determined by use of the hu fc ELISA.

Example 1

IGFBP Variant Binds Growth Factors in Addition to IGF-1 and IGF-2

Table 2 below summarizes the growth factor binding to different fragments of BP3 tested in 0.65 M NaCl. 4141 (SEQ ID NO: 23) is a fragment comprising the N-terminus and the linker region from h3t33; 4142 (SEQ ID NO: 24) is the N-terminus only; 4382 (SEQ ID NO: 25) is the complete link region. These data indicated that the N-terminus alone (ligand 4142) and the linker region alone (ligand 4382) were unable to bind nrgbx, bFGF, VEGFB and PDGF, but the N-terminus plus partial linker (ligand 4141) was sufficient to bind nrgbx, bFGF, VEGFB and PDGF. These data suggested that the partial linker sequence contributed to non-IGF growth factor binding. These data suggested that interaction of the N-terminus and the linker region is involved in non-IGF growth factor binding.

TABLE 2

| | growth factor tested in .65M NaCL | | | | | |
|---|---|---|---|---|---|---|
| ligand | igf1 | igf2 | nrgbx | bFGF | VEGF B | PDGF AB |
| 4141 | + | + | + | + | + | + |
| 4142 | + | + | − | − | − | − |
| 4382 | − | − | − | − | − | − |

Example 2

Construction of Fc Dimers and IGFBP Chimeras

All six IGFBP family members bind IGF-1 and IGF-2 and share a structure of a highly conserved, disulfide-bonded N-terminal and C-terminal domain linked by a non-conserved linker domain. Both the N- and C-terminal domains participate in IGF binding, which is controlled by the proteolysis of the middle linker domain. Because of the discrete, almost modular domain structure of the IGFBPs, we could easily make chimeras with the three distinct domains. Accordingly, the Fc portion of IgG1 was added to the C-terminus of IGFBP3, thereby forming a chimera that could streamline the purification of binding protein. Dimerization by Fc has also been reported to increase the binding affinity for about 2- to 10-fold and increase the serum half-life. Based on the binding profile of human IGFBP3 obtained from Biacore analysis, we first studied the Fc dimer of IGFBP3 (i.e., 56662).

Example 3

BP3/Fc (56662) Inhibits Proliferation Induced by Multiple Growth Factors

We next examined the effect of 56662 (BP3/Fc) on the proliferation induced by growth factors that interacted with the IGFBP3. The proliferation of MCF-7 breast cancer cells was induced in serum-free medium by individual growth factors like IGF-1, IGF-2, EGF, TGF-a, Nrgbx, b-FGF, and amphiregulin (FIG. 1). It should also be noted that 56662 also inhibited MCF-7 proliferation in the presence of fetal bovine serum (FIG. 1).

Figure 2:
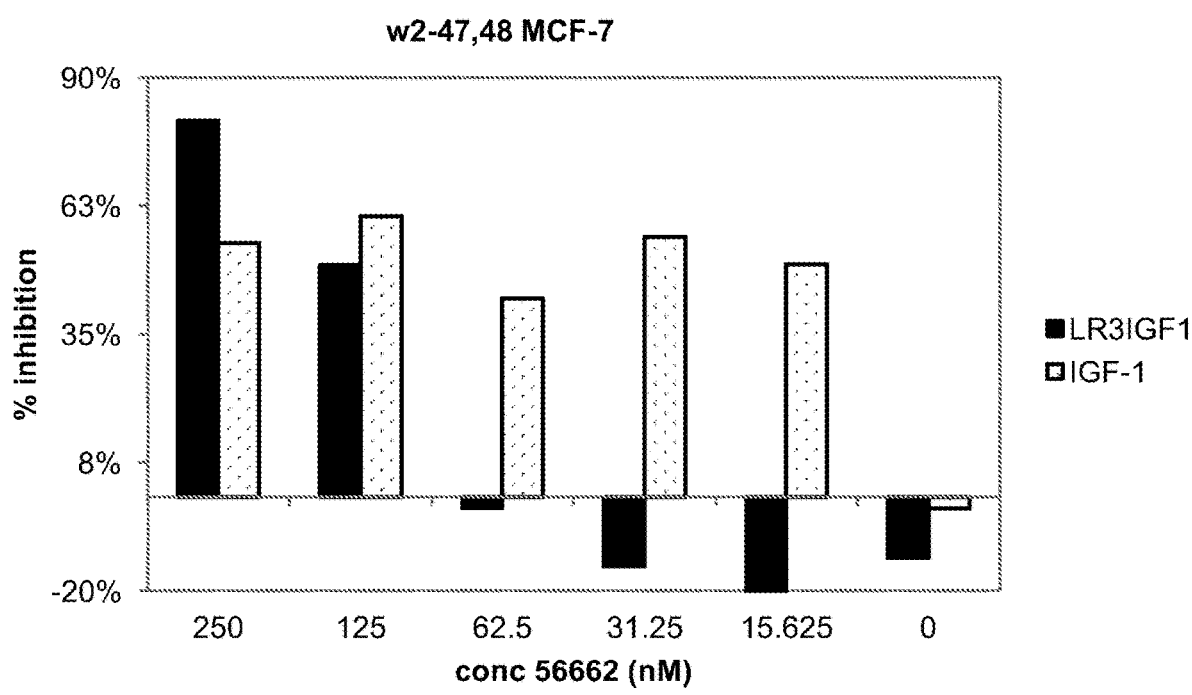
FIG. 2 is a bar graph illustrating the effect of 56662 (BP3/Fc) on the proliferation of MCF-7 breast cancer cells in the presence of IGF-1 or long-R3-IGF-1.

Addition of 56662 in the assay medium inhibited MCF-7 proliferation to a level below that in the absence of any stimulant (FIG. 1). The observed inhibition is most likely a combination of the growth factor sequestration and the IGF-independent inhibition, since high concentrations of 56662 can inhibit proliferation induced by long-R3-IGF-1 (LR3IGF1), an IGF-1 analogue that is not bound by IGFBP3 (FIG. 2).

TABLE 3

| | In vitro inhibition of proliferation (BP3/Fc dimer) |
|---|---|
| IGF-1 | yes |
| IGF-2 | yes |
| neuregulin | yes |
| HGF | yes (hep3B, HUVEC) |
| PDGF-AB | yes (3t3) |
| VEGF-B (167) | not tested |
| VEGF-165 | no |
| EGF | yes |
| TGF-α | yes |
| bFGF | yes |

Proliferation tested on MCF-7 cells except as noted.

Table 3 lists the correlation between the IGFBP3 growth factor binding as determined by the inhibition of the proliferation by 56662. The observed inhibitory effects may derive from the growth factor sequestration, and/or IGFBP3 independent effects. For example, 56662 did not bind to EGF but would inhibit the EGF-stimulated proliferation.

Example 4

Recombinant IGFBP3 Protein with Modified Linker Region Exhibits Enhanced Stability To test the stability of the present chimeras, some purified chimeras (see, Table 4) were incubated with PBS or a conditioned medium from the MCF-7 cell line overnight at 37° C. and PBS overnight at 4° C. The IGF-1 binding and VEGF binding were measured using the biotinylated IGF-1 and VEGF. As summarized in Table 4, 56662 (i.e., the unmodified IGFBP3 fused with the IgG Fc portion) exhibited the greatest loss in the IGF-1 binding activity.

TABLE 4

| 3-192 | IGF-1 binding remaining over controls | | | VEGF binding remaining over control | | |
|---|---|---|---|---|---|---|
| | mcf7 | 37 con | 4 control | mcf7 | 37 con | 4 control |
| 56662 | 24% | 41% | 100% | na | na | na |
| h3t33fc | 54% | 99% | 100% | na | na | na |
| Chimera A | 77% | 94% | 100% | 94% | 94% | 100% |
| Chimera B | 82% | 167% | 100% | 73% | 101% | 100% |
| 4-81 | Mcf7 | 37 con | 4 con | Na | Na | na |
| 56662 | 28% | 80% | 100% | | | |
| 3(del2)3 | 43% | 72% | 100% | | | |
| 3(del3)3 | 49% | 84% | 100% | | | |
| H3t33 | 51% | 101% | 100% | | | |

Example 5

Evaluation of Engineered Chimeras by In Vitro Proliferation

Figure 3:
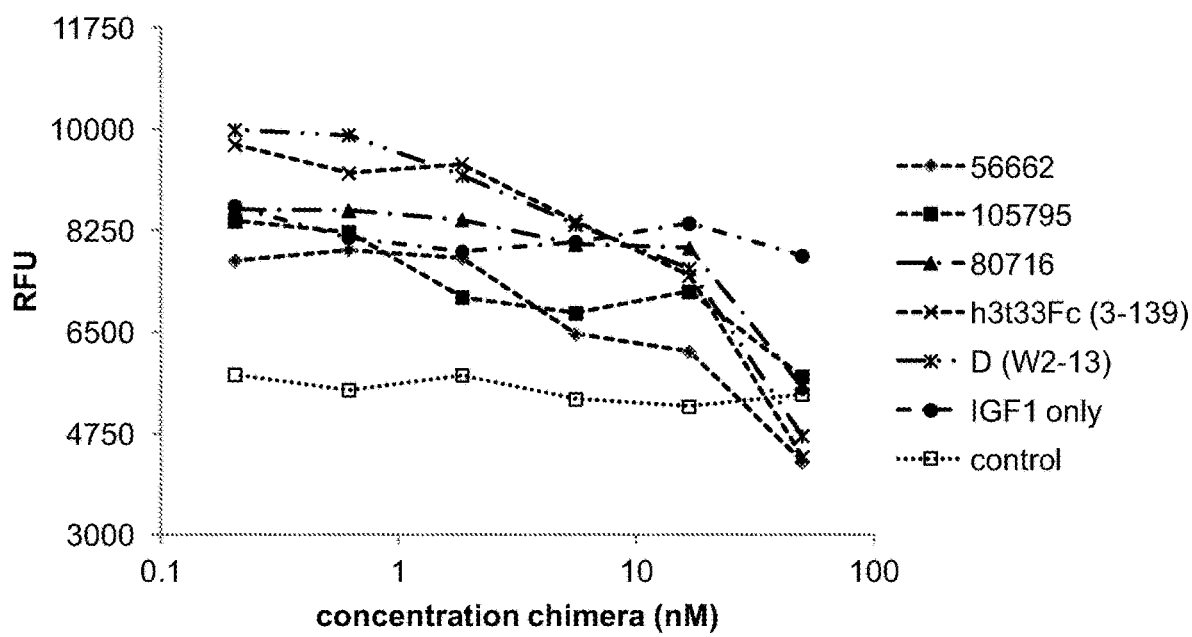
FIG. 3 is a line graph illustrating the effect of various chimeras on the IGF-1-induced proliferation of MCF-7 breast cancer cells.
Figure 4:
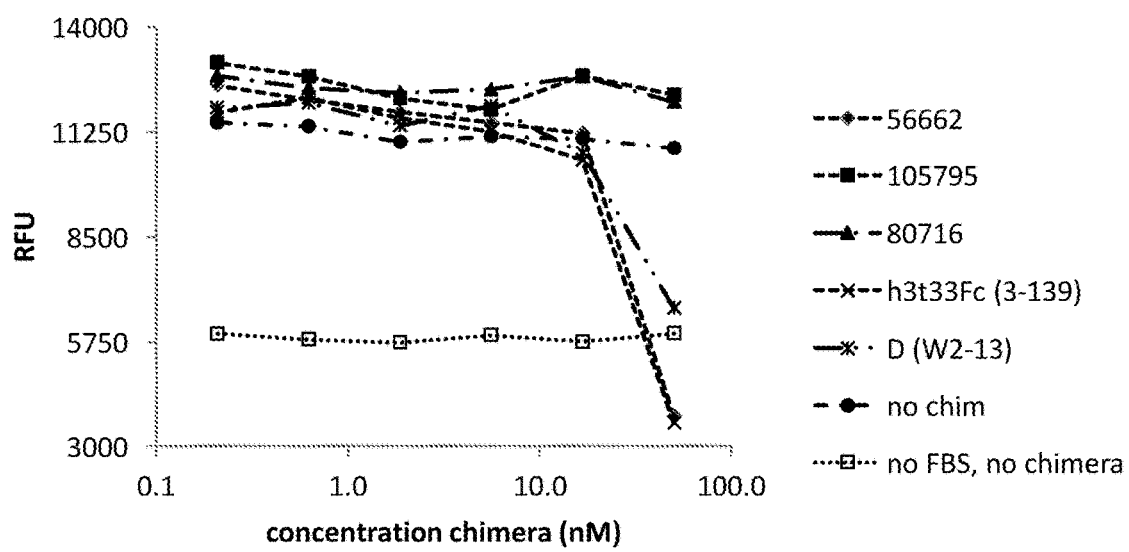
FIG. 4 is a line graph illustrating the effect of various chimeras on the FBS-induced proliferation of MCF-7 breast cancer cells.

The results of two proliferation assays are provided below. FIG. 3 depicts the chimera inhibition of IGF-1-induced proliferation, and FIG. 4 depicts the FBS-induced proliferation in the breast cancer cell line MCF-7. Unexpectedly, constructs 105795 (SEQ ID NO: 9) and 80716 (SEQ ID NO: 16) were unable to inhibit the FBS-induced proliferation in this assay and were eliminated from further study. These results demonstrated the importance of the linker domain.

Figure 5:
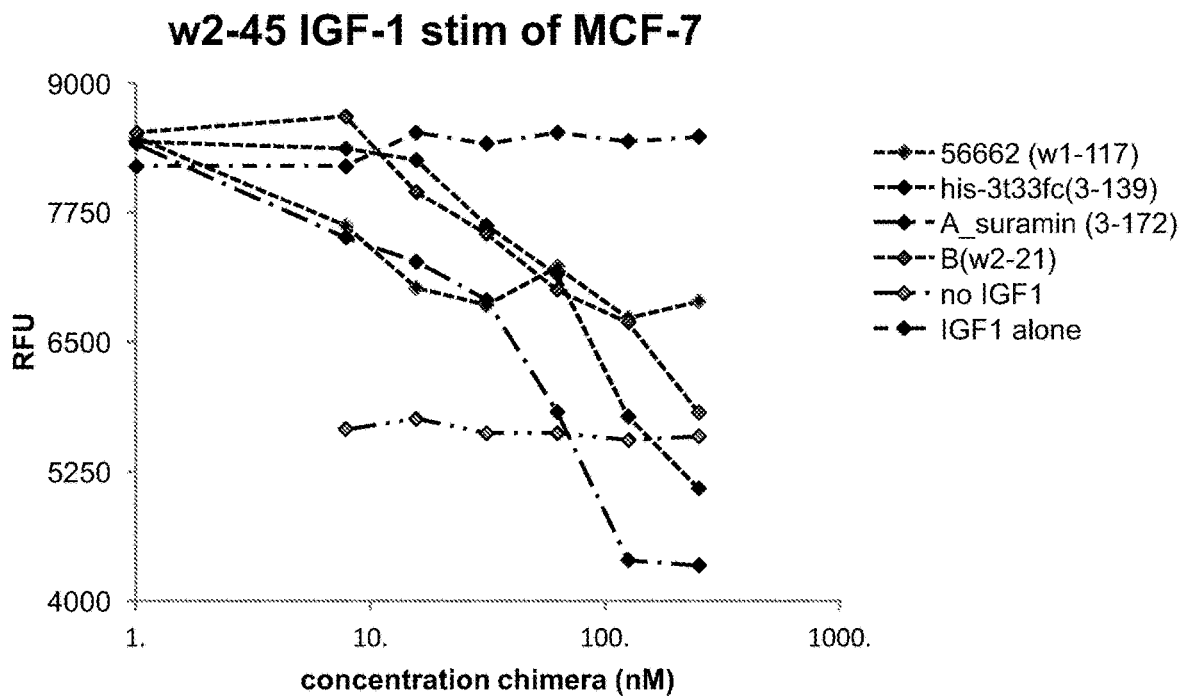
FIG. 5 is a line graph illustrating the effect of various chimeras on the IGF-1-induced proliferation of MCF-7 breast cancer cells.

FIG. 5 demonstrates that chimera A and his3t33fc tended to exhibit a smaller EC50 and a higher maximal inhibition, compared to other bp3 constructs such as 56662 and chimera B. The increased stability in the modified linker region may contribute to the higher activity.

Figure 6:
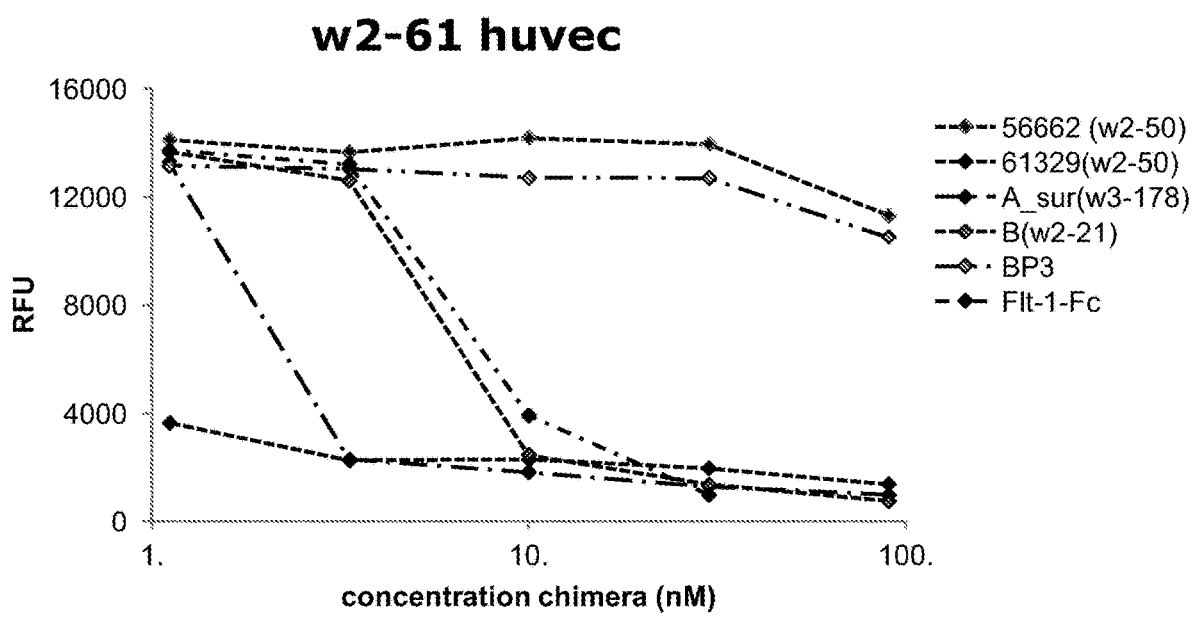
FIG. 6 is a line graph illustrating the effect of various chimeras on the VEGF-induced proliferation of HUVEC cells.
Figure 7:
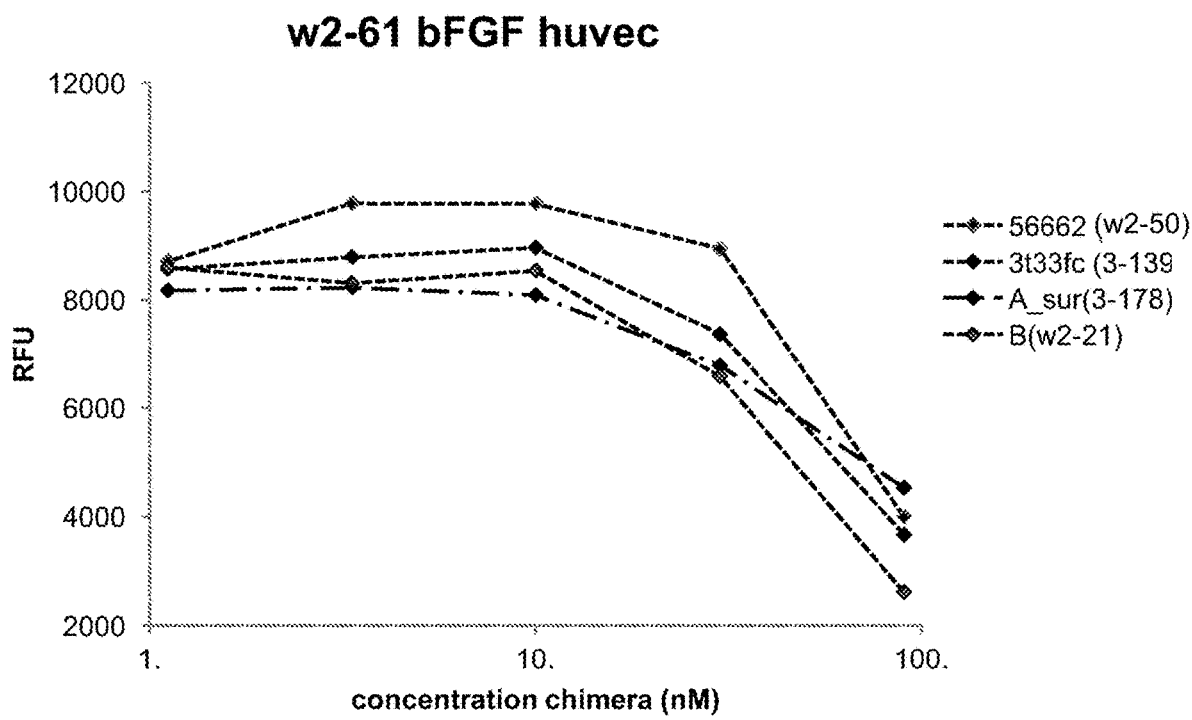
FIG. 7 is a line graph illustrating the effect of various chimeras on the bFGF-induced proliferation of HUVEC cells.

FIG. 6 illustrates the potent inhibition of the VEGF-induced proliferation of HUVEC cells by chimeras containing the VEGF binding domain (e.g., chimera A and chimera B), and FIG. 7 demonstrates that the IGFBP domain inhibited the bFGF-induced proliferation of HUVEC cells.

Example 6

Growth Factor Binding Analysis
6.1 Biacore Analysis

We selected his3t33Fc and chimera A for further analysis and examined their growth factor binding by Biacore and ELISA competition assays. Table 5 below lists the dissociation constants of the chimeras with individual growth factors. It is interesting to note that unlike IGFBP3 and the native IGFBP3 Fc dimer 56662, the chimera with truncated linker domains his3t33fc bound to bFGF with a lower affinity. This result supports the hypothesis that the regions in the linker domain may be necessary for the bFGF binding.

6.2 bFGF Binding

As noted in Table 1, above, we deleted 55 amino acids from the linker region of constructs h3t33Fc and chimera A to eliminate several protease cleavage sites and a hotspot of aggregation. The binding of bFGF was decreased with h3t33Fc (see, Table 5). We made two new constructs with smaller deletions with the hope of retaining the bFGF binding, while at the same time removing the protease sensitive sites and the hotspot for aggregation. These two constructs, 3(del2)3Fc and 3(del3)3Fc have been analyzed for the aggregation, growth factor binding, stability, and in vitro inhibition of proliferation.

TABLE 5

| Dissociation Constants (M) | | |
|---|---|---|
| | his3t33fc | chimeraA |
| IGF-1 | 1.61E−10 | 2.45E−11 |
| IGF-2 | 1.745E−10 | 3.89E−11 |
| nrgbx | 5.98E−09 | 4.88E−09 |
| VEGF | no binding | 3.8E−12* |
| VEGFB | 3E−9 | 5E−10 |
| bFGF | 1.3E−8[#] | 1.92E−9[#] |
| HGF** | 6.08E−10[#] | 2.18E−11[#] |
| PIGF | not done | 9.99E−10 |
| TGF-α | no binding | 9.25E−06 |
| mIGF-1 | 2.1E−10 | 1.37E−10 |
| mIGF-2 | 1.4E−10 | 5.13E−11 |

*The kd is very low and difficult to measure.
**The extent of protease cleavage to generate the active two chain HGF molecule may vary between commercial HGF preparations.
[#]Immobilized growth factor.

As seen below in Table 6, the smaller deletions in 3(del2)3 and 3(del3)3 exhibited higher affinity binding to bFGF, while their affinities to IGF-1 was approximately the same as the wild-type IGFBP3 (KD=3.63E-10).

TABLE 6

| KD (M) 4-79 | bFGF[#] | IGF-1 |
|---|---|---|
| 3(del2)3 | 4.32E−09 | 3.20E−10 |
| 3(del3)3 | 3.44E−09 | 3.71E−10 |
| h3t33 | 1.33E−08 | 5.75E−10 |

[#]Immobilized bFGF 6.3 Chimera A Binds Both VEGF and IGF-1 Simultaneously

Figure 8:
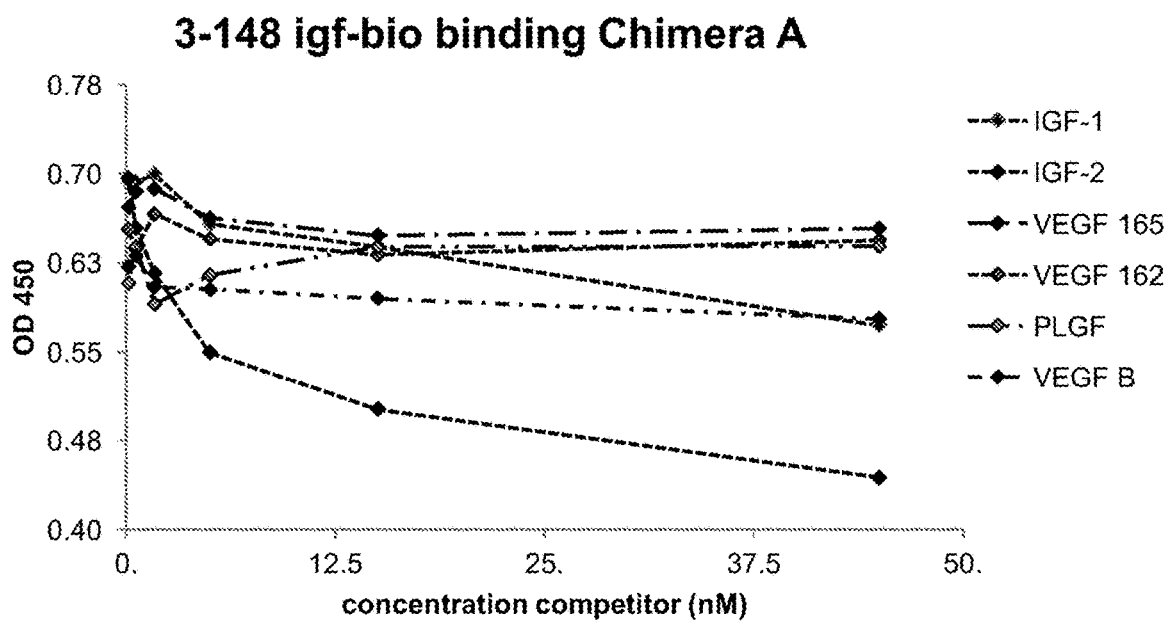
FIG. 8 is a line graph illustrating the competition ELISA of biotinylated IGF-1 for binding to Chimera A and growth factor domains.
Figure 9:
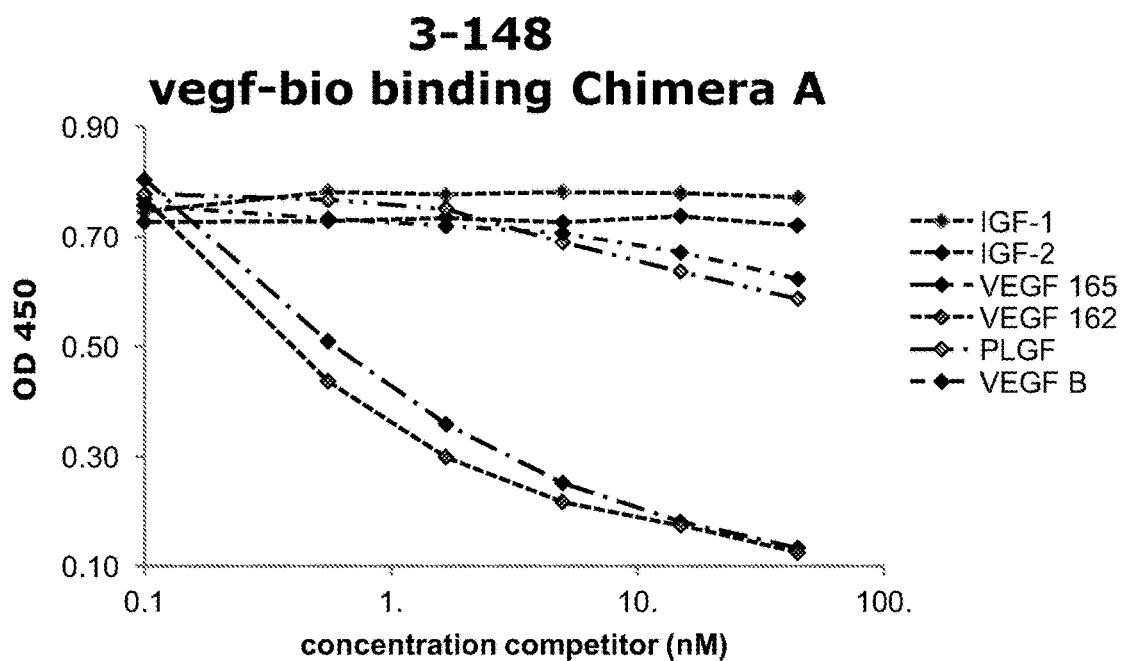
FIG. 9 is a line graph illustrating the competition ELISA of biotinylated VEGF for binding to Chimera A and growth factor domains.
Figure 10:
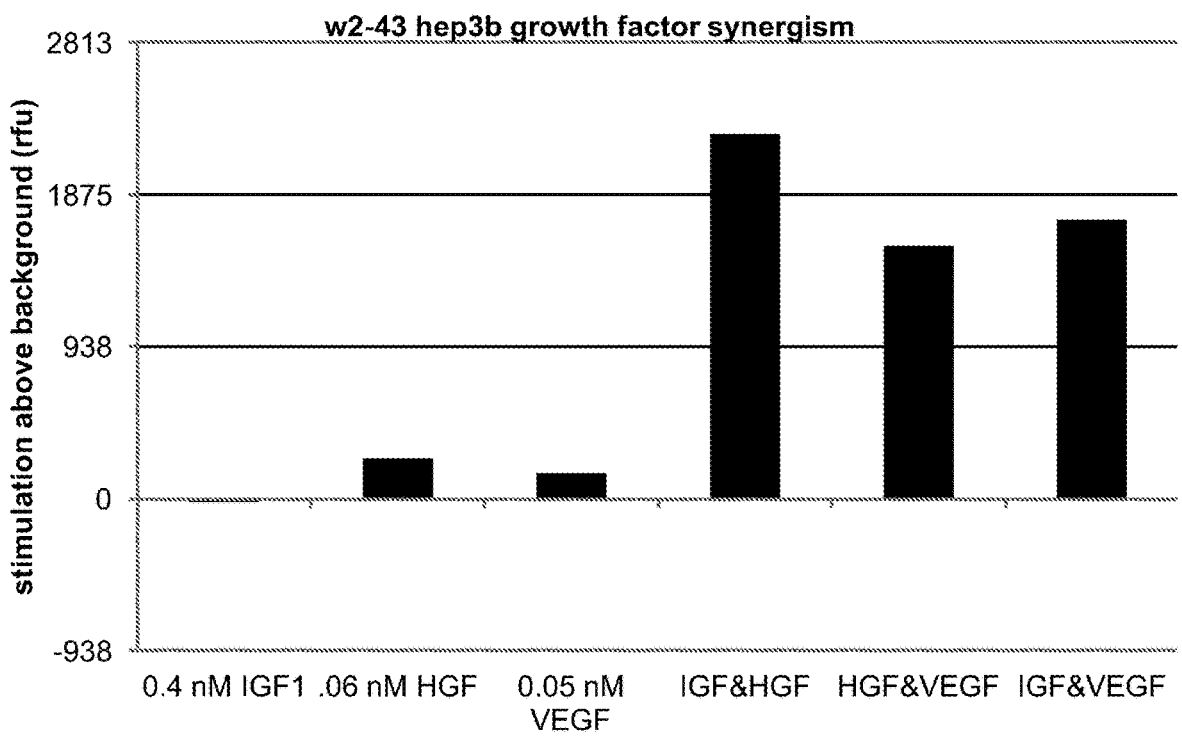
FIG. 10 is a bar graph illustrating the effect of various growth factors, alone or in combination, on the proliferation of hepatoma cell line hep3B.
Figure 11A:
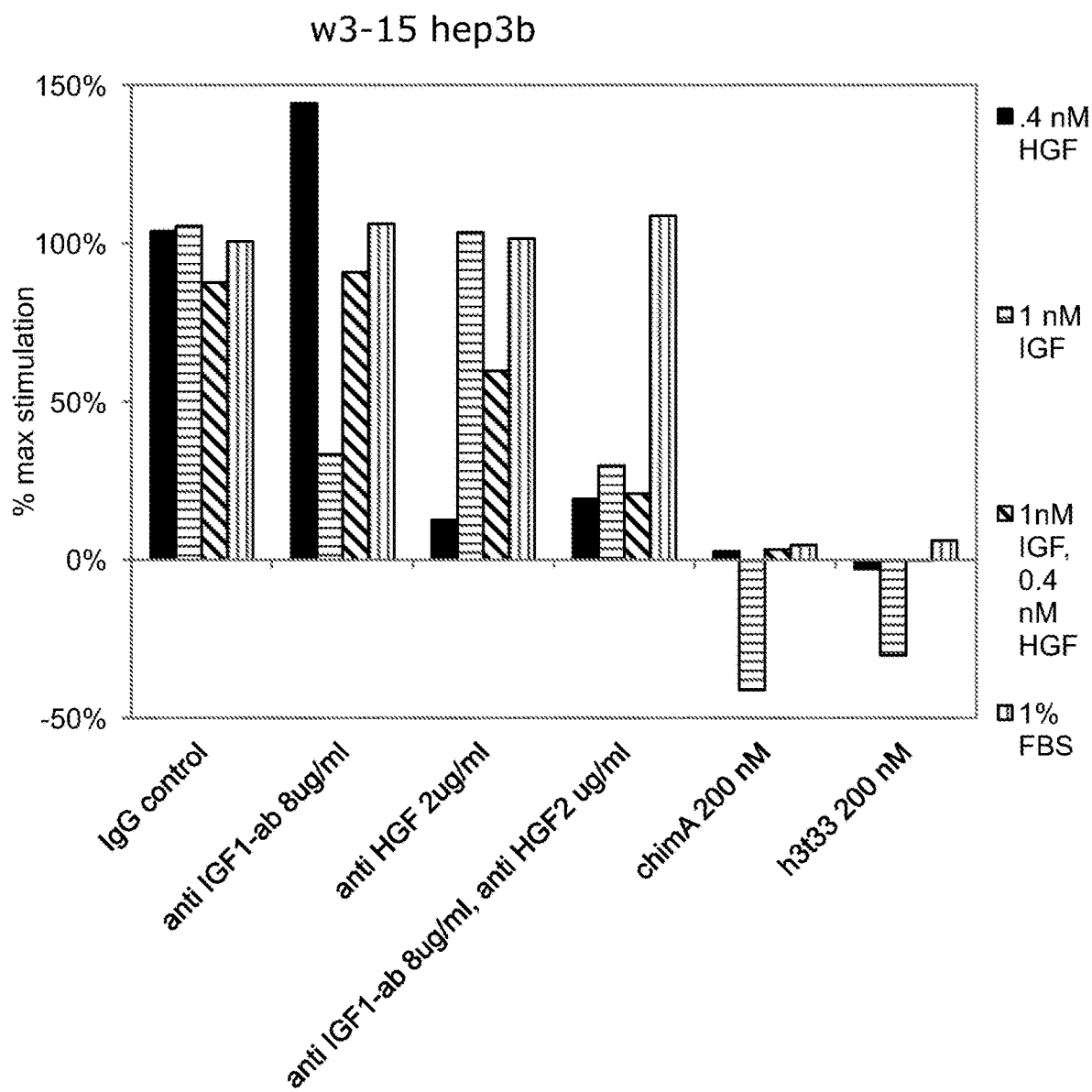
FIG. 11A is a bar graph illustrating the effect of various chimeras on the IGF1-induced and/or HGF-induced proliferation of hepatoma cell line hep3B.
Figure 11B:
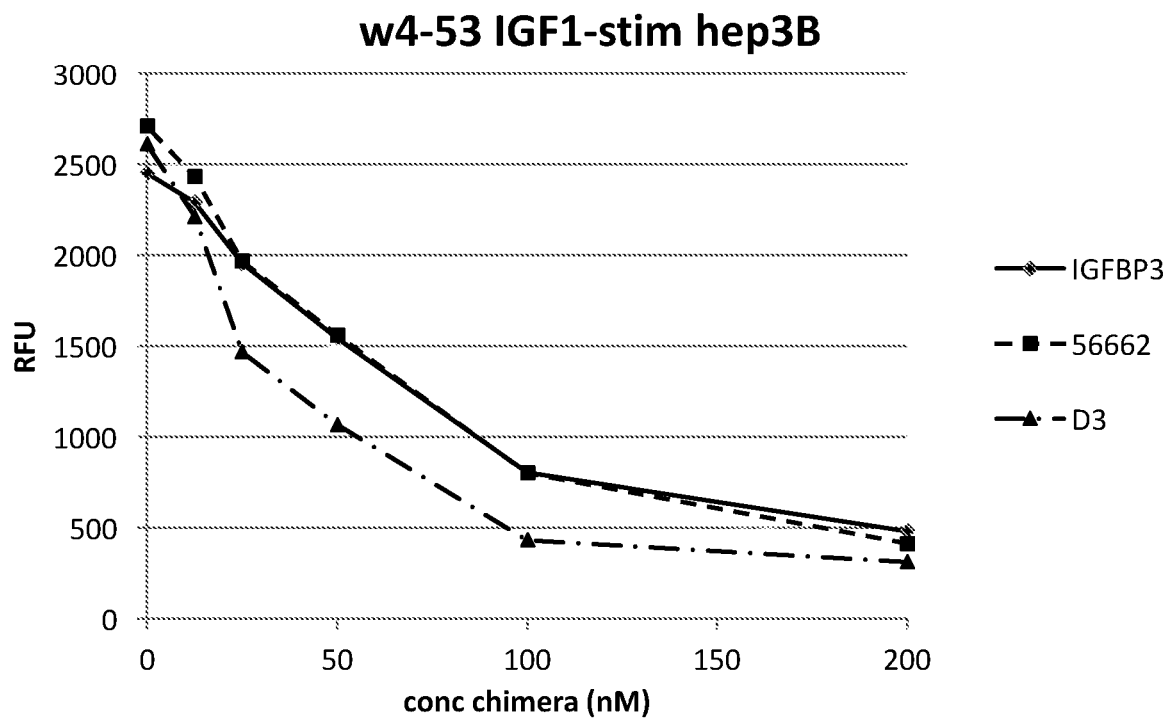
FIG. 11B and FIG. 11C are line graphs respectively illustrating the effect of various chimeras on the IGF1-induced and FBS-induced proliferation of hepatoma cell line hep3B.
Figure 11C:
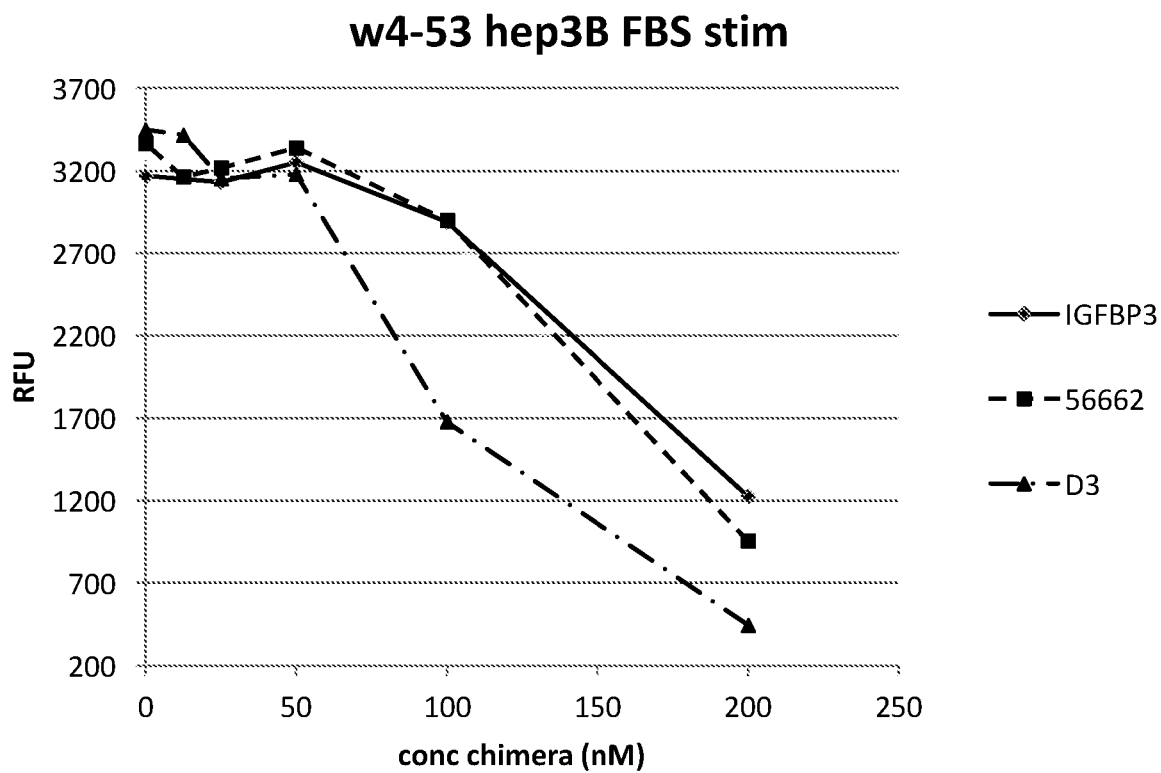
Figure 11D:
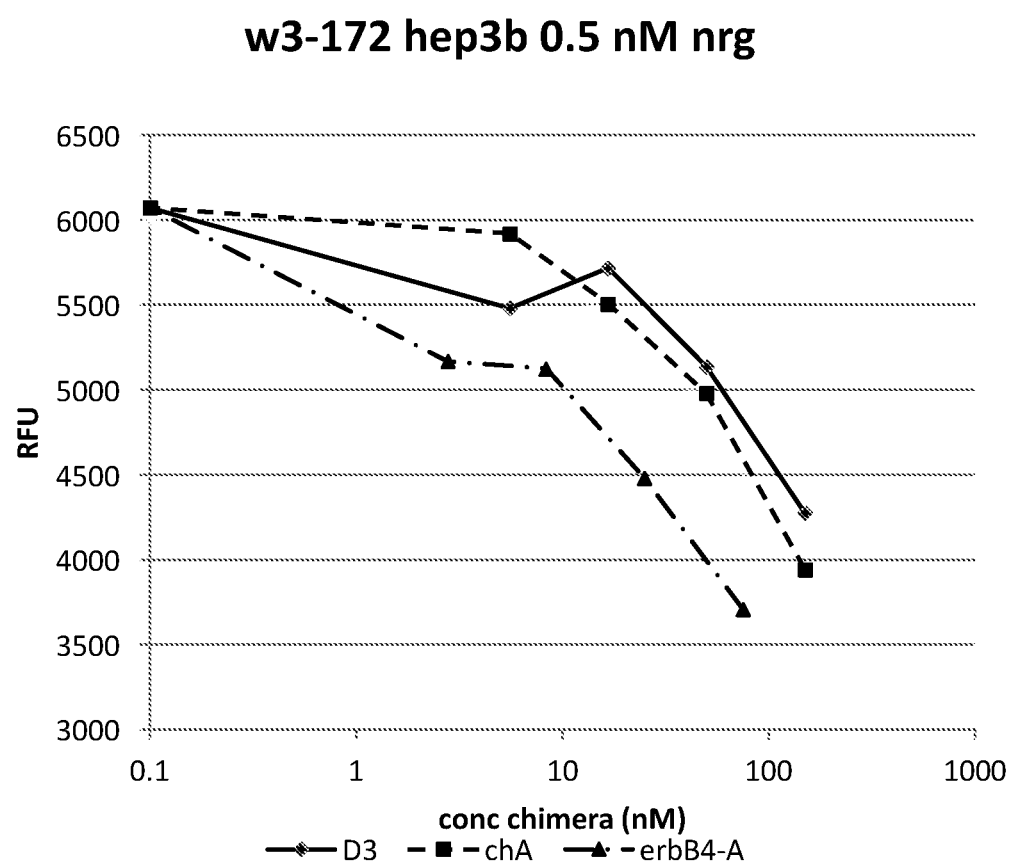
FIG. 11D is a line graph illustrating the increased potency of IGFBP3 variant with the neuregulin binding domain.
Figure 12:
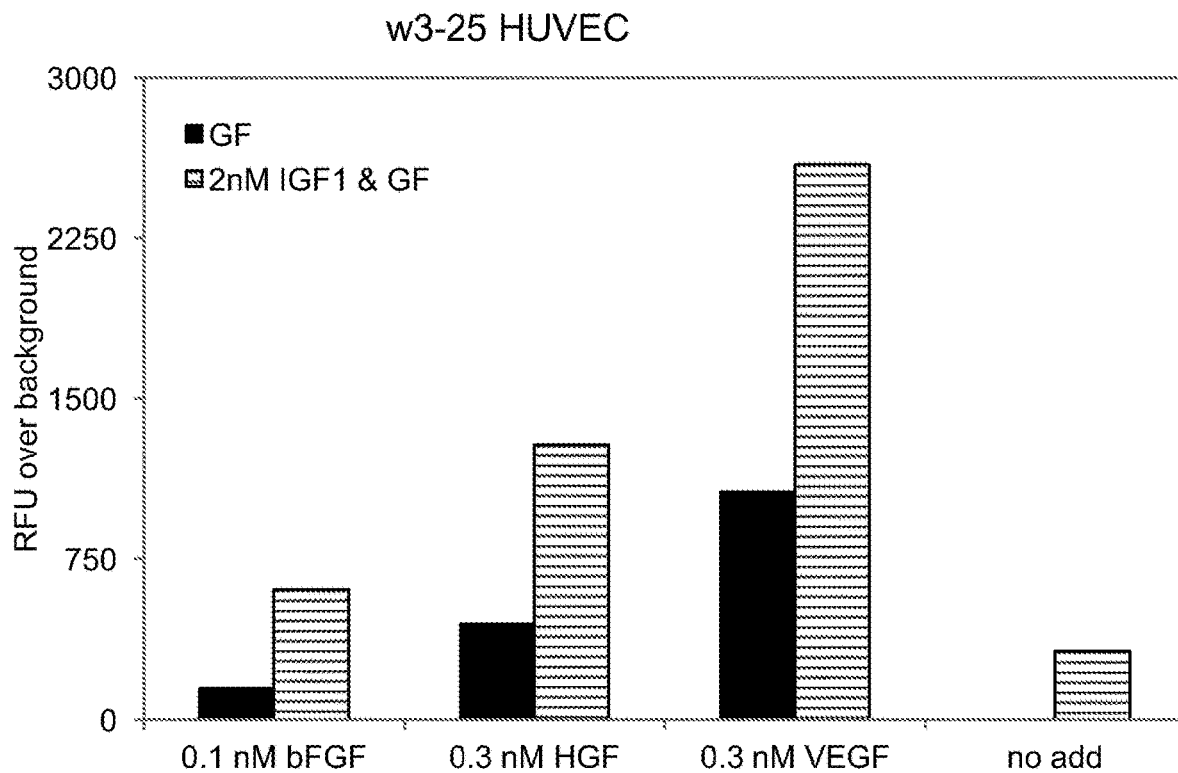
FIG. 12 is a bar graph illustrating the effect of various growth factors in combination with IGF1 in stimulating the proliferation of HUVEC cells.
Figure 13:
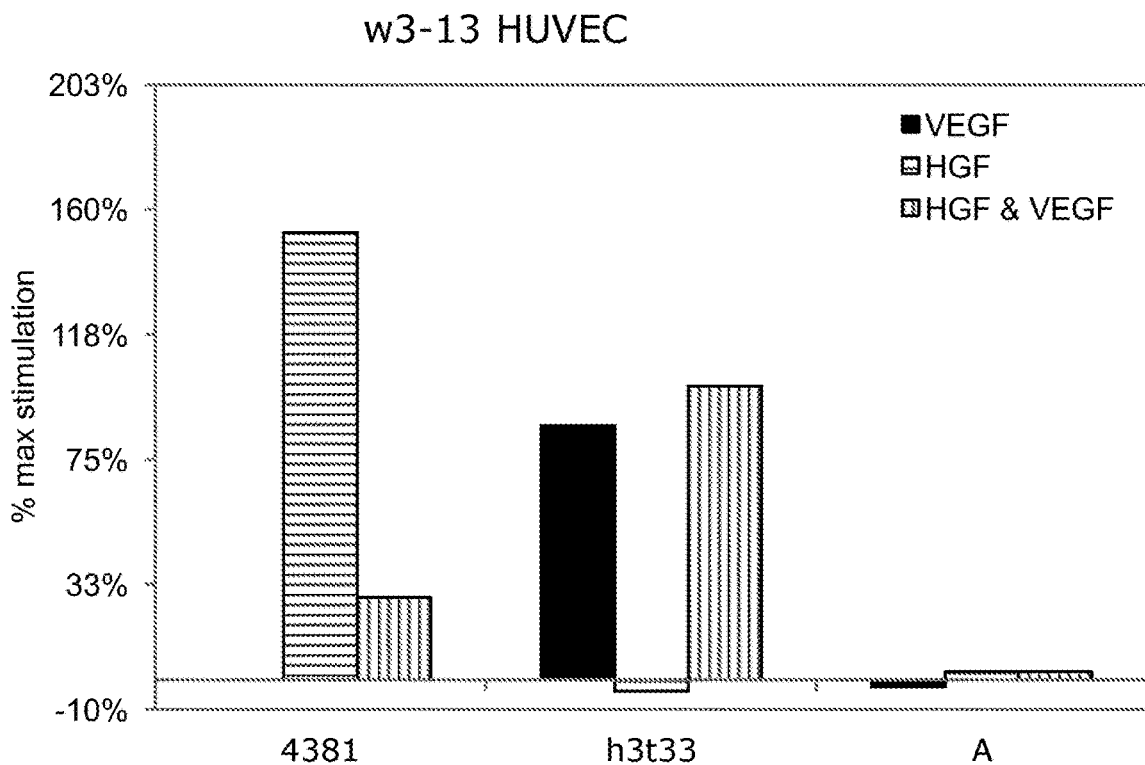
FIG. 13 is a bar graph illustrating the effect of various chimeras on the VEGF-induced and/or HGF-induced proliferation of HUVEC cells.
Figure 14:
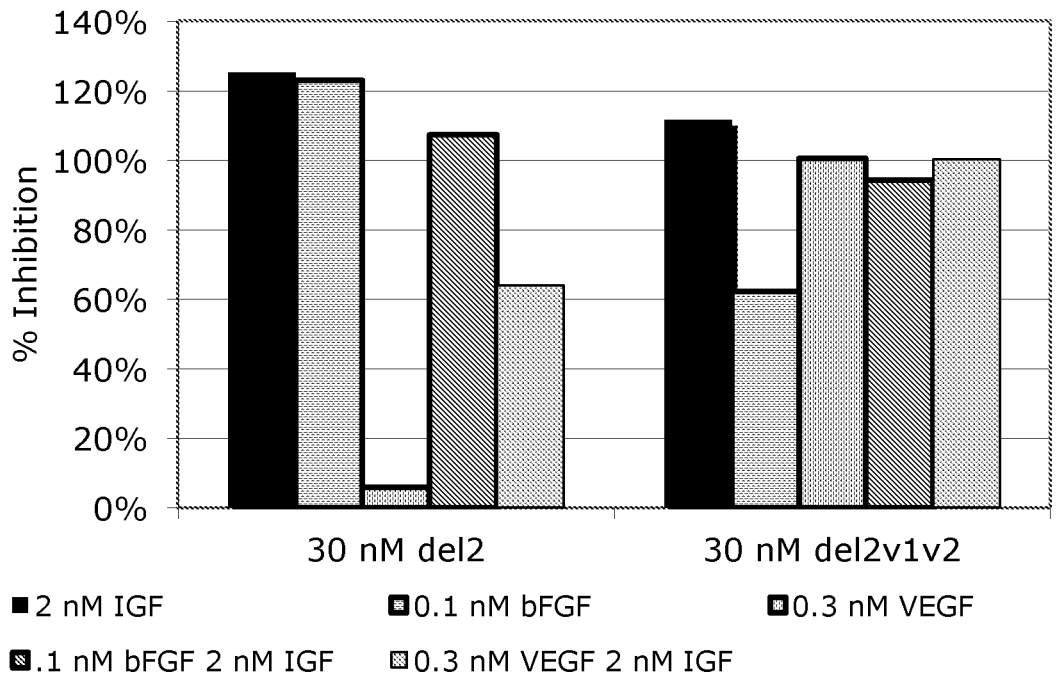
FIG. 14 is a bar graph illustrating the effect of various chimeras on the growth factor-induced proliferation of HUVEC cells.
Figure 15:
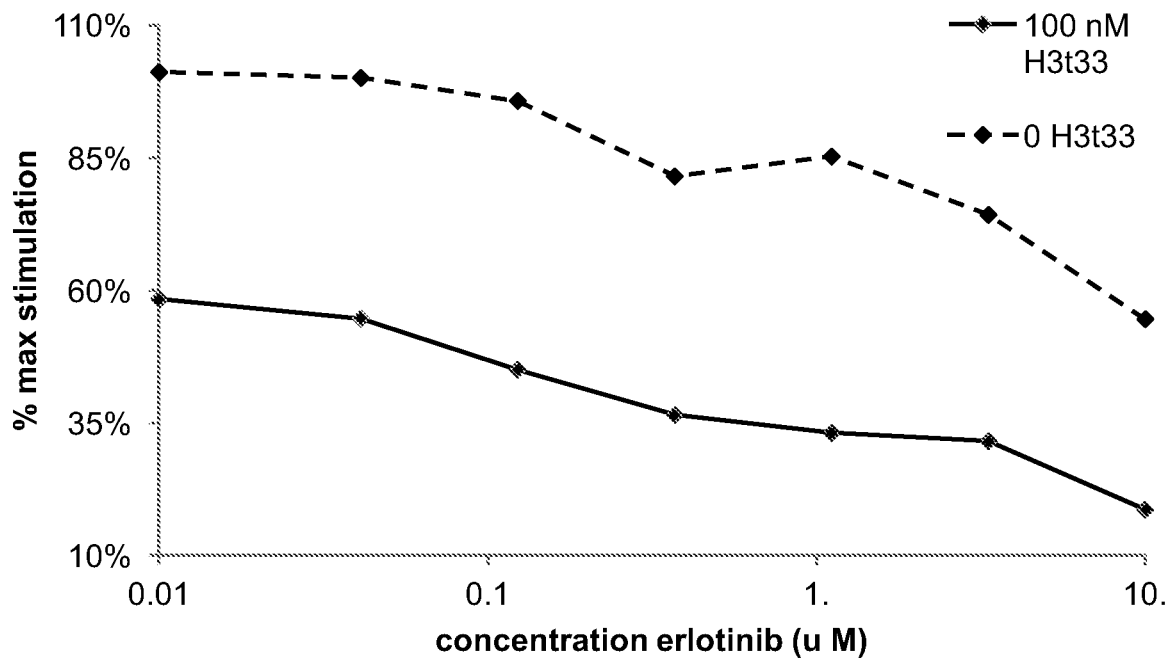
FIG. 15 is a line graph illustrating the effect of chimera H3t33 on the proliferation of EGFR-wildtype hep3B cells treated with erlotinib.
Figures 16A, 16B:
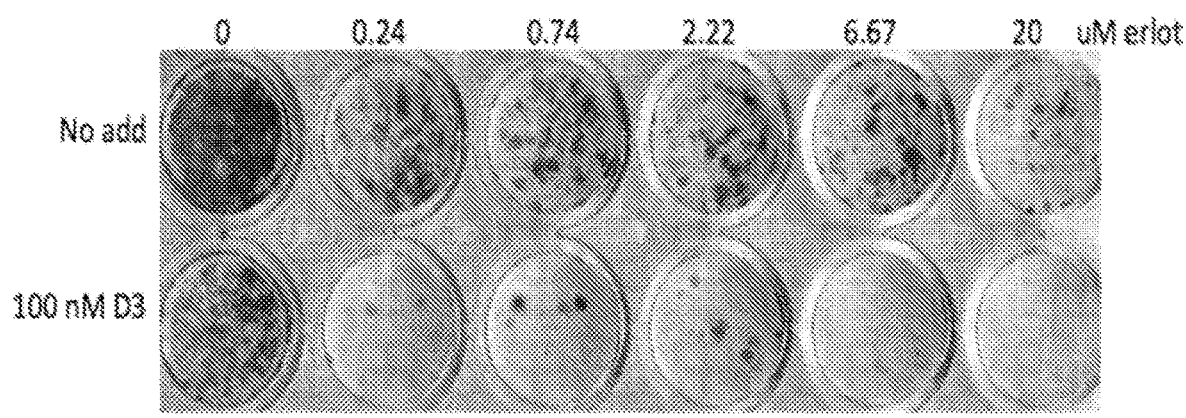
FIG. 16A and FIG. 16B provide experimental results showing the effect of the chimera D3 (3del33) on the proliferation of EGFR-wildtype hep3B cells treated with erlotinib, sorafenib, afatinib, or doxorubicin.

Binding specificity was also studied by competition binding assays using biotinylated IGF-1 (IGF-1-bio) or biotinylated VEGF (VEGF-bio) in the growth factor ELISA assay. As shown in FIG. 8, IGF-1 and IGF-2 competed with IGF-1-bio. VEGF-B, which bound to IGFBP3, partially inhibited the IGF-1-bio binding. VEGF 165, VEGF 162, and PlGF did not affect the IGF-1-bio binding. FIG. 9 shows that VEGF 165, VEGF 162, and PlGF inhibited the VEGF-bio binding. VEGF-B, which bound to IGFBP3 and to the VEGF-trap domain, partially inhibited the VEGF-B binding. IGF-1 and IGF-2 did not affect the VEGF-bio binding. The competitive inhibition data suggest that the IGF and VEGF could bind simultaneously with the chimera A.

To further examine the nature of the VEGF and IGF binding to chimera A, simultaneous binding was examined using the surface plasmon resonance. The results demonstrated that chimera A, which contained a VEGF binding domain, is the only chimera showed an increase in response units in binding VEGF, whereas all chimeras bound to IGF-1 (data not shown). The KD of chimera A for IGF-1 remained the same in the absence (0.4 nM) and the presence (0.2 nM) of 3 nM VEGF.

Example 7

Addition of erbB4 Domain Enhances Neuregulin Binding

In this example, erbB4 domain 1 was attached to the N-terminus of the recombinant IGFBP3-Fc or the recombinant IGFBP3-v1v2-Fc. The experimental data, as summarized in Table 7 below, indicated that the addition of a single domain from erbB4 enhanced the binding to neuregulin. These data establish that by combining a suitable receptor domain with the IGFBP3, it is feasible to enhance the binding efficacy toward the specific growth factor, while at the same time keep the multiple binding capabilities.

TABLE 7

| | Sequence ID | Kd nrgECD# | Kd nrgEGF |
|---|---|---|---|
| IGFBP3-Fc | 7 | 5.3 E−9 | No binding |
| IGFBP3-erbB4-Fc | 22 | 4.0 E−12 | 6.0 E−9 |
| IGFBP3-v1v2-Fc | 21 | 1.8 E−10 | No binding |
| IGFBP3-v1v2-erbB4-Fc | 20 | 1.1 E−13 | 1.1 E−8 |

Immobilized nrgECD nrgEGF comprises amino acids Thr176-Lys246 of neuregulin-beta 1; nrgECD comprises amino acids Ser2-Lys246 of neuregulin beta 1.

Example 8

IGFBP3 Chimeras Inhibit In Vitro Proliferation Stimulated by the Growth Factors it Binds The BP3-fc construct inhibited the proliferation of cancer cells that had been stimulated by IGF-1, IGF-2, neuregulin, HGF, and bFGF. In addition, the construct also inhibited the proliferation induced by PDGF BB in fibroblasts.

TABLE 8

| | IGF-1 | IGF-2 | nrgbx | bFGF | HGF | PDGF BB | VEGF | PIGF |
|---|---|---|---|---|---|---|---|---|
| BP3-FC | inh | inh | inh | inh | inh | inh | no | no |
| VEGF-trap | no | no | no | no | no | no | inh | inh |
| BP-3-VEGF-trap-Fc | inh | inh | inh | inh | inh | inh | inh | inh |

The BP3-VEGF-trap-fc (including the IGFBP3 domains, the VEGFR1 domain 2 and VEGFR2 domain 3 (VEGF-trap (22)), and human immunoglobulin Fc region) broadened the binding to include VEGF-A, VEGF-B, and placental growth factor (PIGF). This BP3-VEGF-trap chimera could inhibit the proliferation stimulated by IGF-1, IGF-2, neuregulin, PDGF-BB, HGF, bFGF, VEGF-A, and PIGF (see, Table 8).

Example 9

Inhibition by Chimera is Superior to a Combination of Antibodies

Although the growth factor stimulation of proliferation in vitro is most conveniently studied by the addition of a single growth factor, this method does not reflect the in vivo complexity of interacting factors. The human hepatoma cell line hep3B could be stimulated by many growth factors including IGF-1, IGF-2, HGF, bFGF, VEGF, and neuregulin. We demonstrated that a combination of growth factors could synergistically stimulate cell proliferation (see, FIG. 10).

The bar graph in FIG. 11A indicates that proliferation stimulated by the combination of IGF-1 and HGF in hep3b cells was inhibited by chimeras containing the IGFBP3 domain. In contrast, the inhibition of IGF-1/HGF proliferation required a combination of anti-IGF-1 and anti-HGF antibodies. Additionally, the chimera inhibited the proliferation induced by 1% fetal bovine serum while even a combination of these two antibodies did not reduce the proliferation.

FIG. 11B and FIG. 11C respectively depict the chimera inhibition of IGF-1-induced or FBS-induced proliferation in the human hepatoma cell line hep3B. These data indicated that the present chimera D3 was more effective in inhibiting the proliferation induced by either IGF-1 or FBS. Specifically, the $EC_{50}$ of the chimera D3 in inhibiting IGF-1 induced proliferation was 21 nM, which was much lower than that for IGFBP3 (44 nM) and chimera 56662 (47 nM). Similarly, for FBS-induced proliferation, the ECK for chimera D3, IGFBP3 and chimera 56662 was 85, 200, and 201 nM, respectively.

FIG. 11D is a line graph demonstrating that the chimera erbB4-A (a chimera having the neuregulin binding domain) was more effective in inhibiting the proliferation induced by neuregulin. Specifically, the $IC_{50}$ of the chimera D3, chimera A, and chimera erbB4-A in inhibiting neuregulin-induced proliferation were 80, 47, and 14 nM, respectively.

Example 10

IGFBP3-V1V2 Chimera Inhibits HUVEC Proliferation Induced by Multiple Growth Factors Growth factor synergism can also be observed in the proliferation of HUVEC cells. The individual growth factors bFGF, HGF, IGF-1, and VEGF stimulated the proliferation of HUVEC cells, and the graph in FIG. 12 demonstrates that IGF-1 further enhanced the proliferation induced by bFGF, HGF or VEGF.

As expected, chimeras containing only an IGFBP3 (h3t33 and 3(del2) 3) domain inhibited the proliferation induced by IGF, bFGF, HGF or a combination but did not inhibit VEGF-induced proliferation (FIG. 13). A control protein consisting only of the VEGF binding domain (4381) inhibited only the VEGF-induced proliferation and therefore partially inhibited VEGF+HGF (FIG. 13). Chimeras containing both an IGFBP3 and VEGF binding domain (chimA and 3(del2)3V1V2), inhibited proliferation stimulated by IGF-1, bFGF, HGF, VEGF, and combinations (FIG. 14).

Example 11

Chimera Enhances Inhibition of Cancer Cells by Targeted Therapy or Chemotherapy

Rational combinations of drugs targeting different pathways may kill, either additively or synergistically, a higher percentage of cancer cells. Combinations may more effectively challenge the heterogeneity of tumors and decrease the resistance. The results in FIG. 15 and FIG. 16A showed that the present chimera h3t33Fc or D3 (3del33) synergistically inhibited hep3B cells treated with erlotinib. Specifically, in cells not treated with chimera h3t33Fc, the $IC_{50}$ of erlotinib to EGFR-wildtype hep3B cells were about 10 μM (FIG. 15). In contrast, with the addition of 100 nM chimera h3t33Fc, the $IC_{50}$ of erlotinib to EGFR-wildtype hep3B cells were reduced to about 0.1 μM (FIG. 15). In other words, the inhibitory activity of erlotinib was increased by about 100-fold when the present chimera was administered.

The proliferation analysis, as summarized in FIG. 16B indicated that proliferation of cells treated with the present chimera D3 (3del33) was reduced significantly, as compared to cells that were not treated by any inhibitor. Hep3B cells were also treated with 2 uM erlotinib, 2 uM sorafenib, or 0.15 uM afatinib (approximate therapeutic concentrations) with or without the co-treatment of the present chimera D3, and the co-treatment with the present chimera D3 further reduced cell proliferation. The proliferation of hep3B cells was also greatly inhibited by the 0.01 uM doxorubicin, and co-treatment of doxorubicin and the chimera D3 reduced proliferation even further.

Figures 17A, 17B:
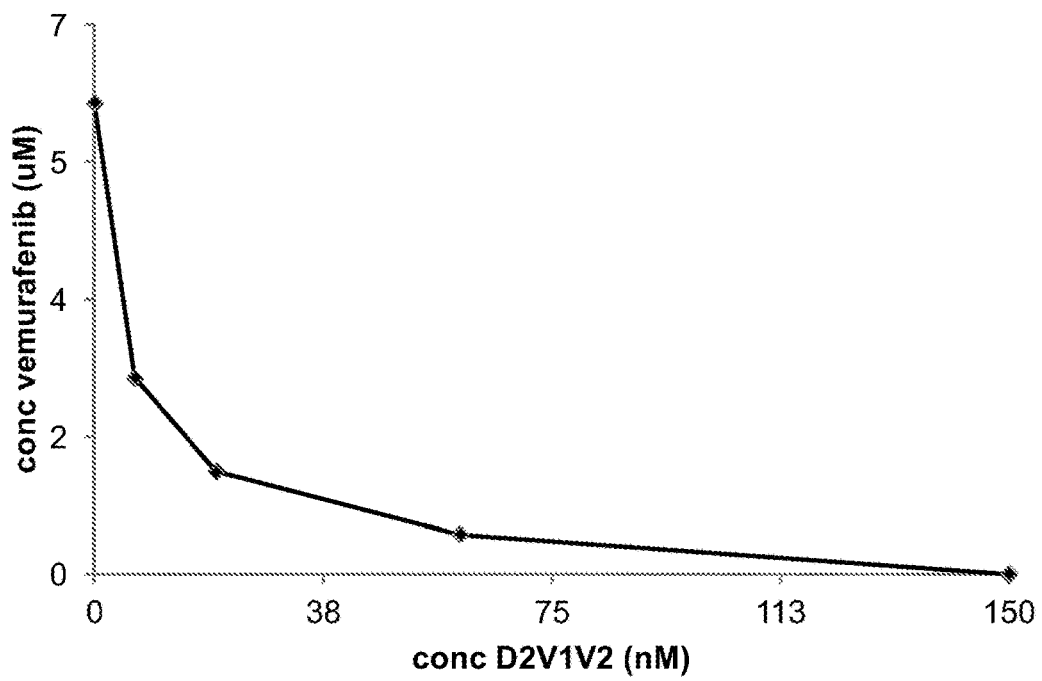
FIG. 17A is an isobologram demonstrating the synergistic inhibition of chimera D2V1V2Fc with vemurafenib in HT29 cells.
FIG. 17B provides experimental results showing the synergistic inhibition of chimera D3 with vemurafenib in HT29 cells.

The combination of drug (erlotinib and vemurafenib in hep3b and HT29 cells, respectively) and chimera can be synergistic; so, in addition to enhancing the inhibition, the chimera addition may also lower drug concentration requirements and reduce side effects. FIG. 17A is an isobologram demonstrating the synergistic inhibition of chimera D2V1V2Fc with vemurafenib in HT29 cells. The photographs in FIG. 17B also indicate the synergistic inhibition of D3 chimera with vemurafenib in HT29 cells.

Since the A549 cell line contains a KRAS mutation, it is expected that A549 cells be resistant to TKIs such as AZD9291 and erlotinib. MEK inhibitors such as trametinib were designed to target the RAS/MEK/ERK pathway. The results in FIG. 18A demonstrated that the administration of the present D3 chimera, alone, or in combination with the TK, reduced the growth of A549 lung carcinoma cells. KRAS tumors are commonly treated with chemotherapeutic agents like cisplatin. FIG. 18B demonstrated that the addition of D3 to cisplatin further inhibited A549 growth.

Example 12

IGFBP3 Chimeras in Combination with Receptor Tyrosine Kinase Inhibitors Reduce the Number of Drug Tolerant Persisters Treating cancer cells with inhibitors is known to stimulate cellular changes; these cellular changes support the survival of some cancer cells, which are known as drug tolerant persisters (DTPs) (23). It is believed that mutations resulting in acquired resistance evolve from these DTPs; hence, the reduction of DTP's will likely postpone the development of resistance. It is also known that growth factors can rescue cancer cells from targeted therapy and increase the number of drug tolerant persisters and thus promote resistance. These DTP's are less than 5% of the control population in the standard 96-well 4-day assay and therefore not quantifiable.

Figure 19A:
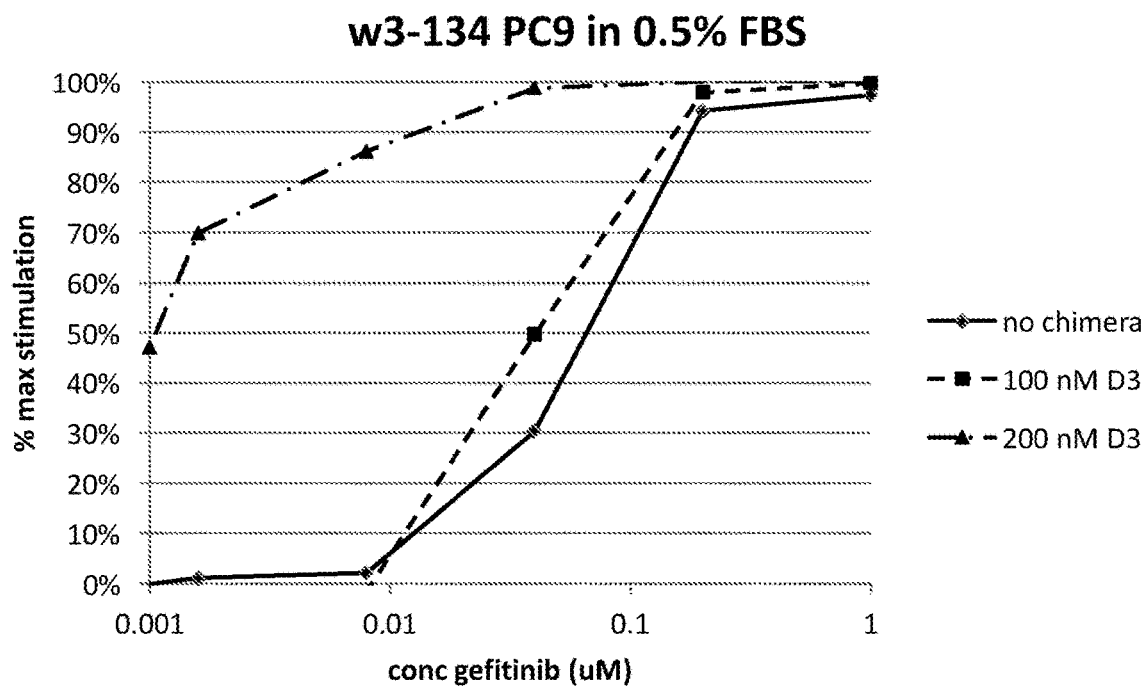
FIG. 19A is a line graph showing the effect of the chimera D3 on the proliferation of PC-9 cells treated with gefitinib.
Figure 19B:
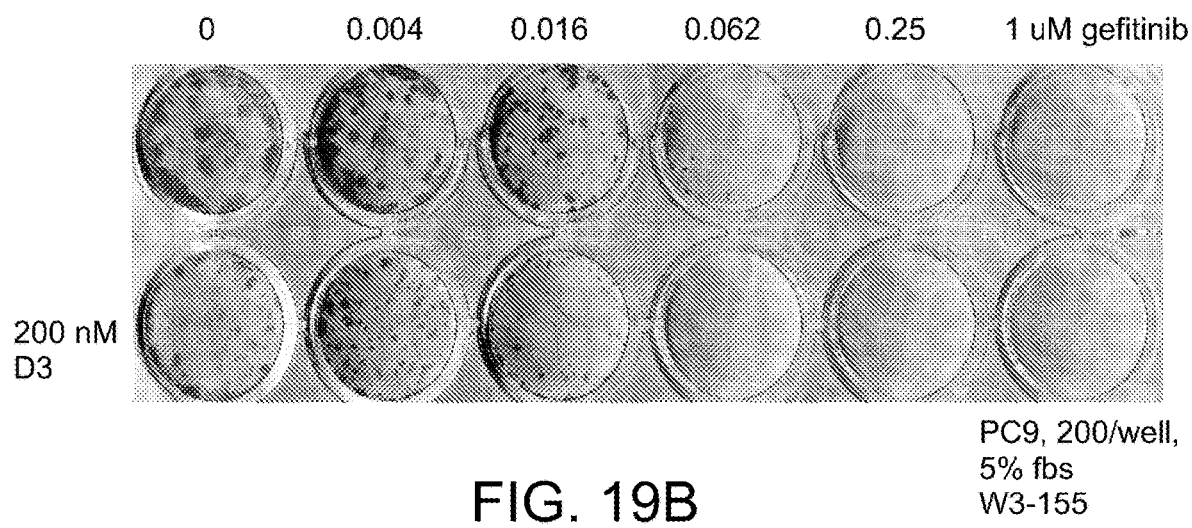
FIG. 19B provides experimental results showing the effect of chimera D3 on the proliferation of PC-9 cells treated with gefitinib.

Proliferation assays at clonal densities allows measurement of these DTPs. PC-9 cells are a human non-small cell lung cancer line with a EGFR deletion with high sensitivity to EGFR TKI's (24). As shown in FIG. 19A, the addition of 200 nM D3Fc to gefitinib decreased the $IC_{50}$ of gefitinib by 70-fold in a four-day assay; the clonal density assay in FIG. 19B also demonstrated that D3 decreased the $IC_{50}$ and reduced surviving cells.

Figure 20:
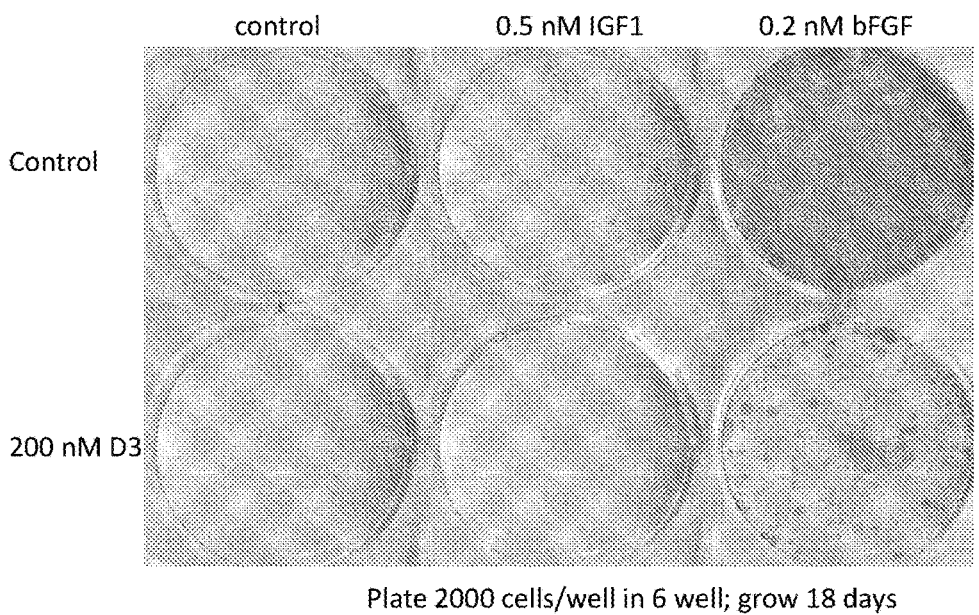
FIG. 20 provides experimental results showing the effect of chimera D3 on the proliferation of PC-9 cells treated with gefitinib and/or IGF1 and bFGF.
Figure 21:
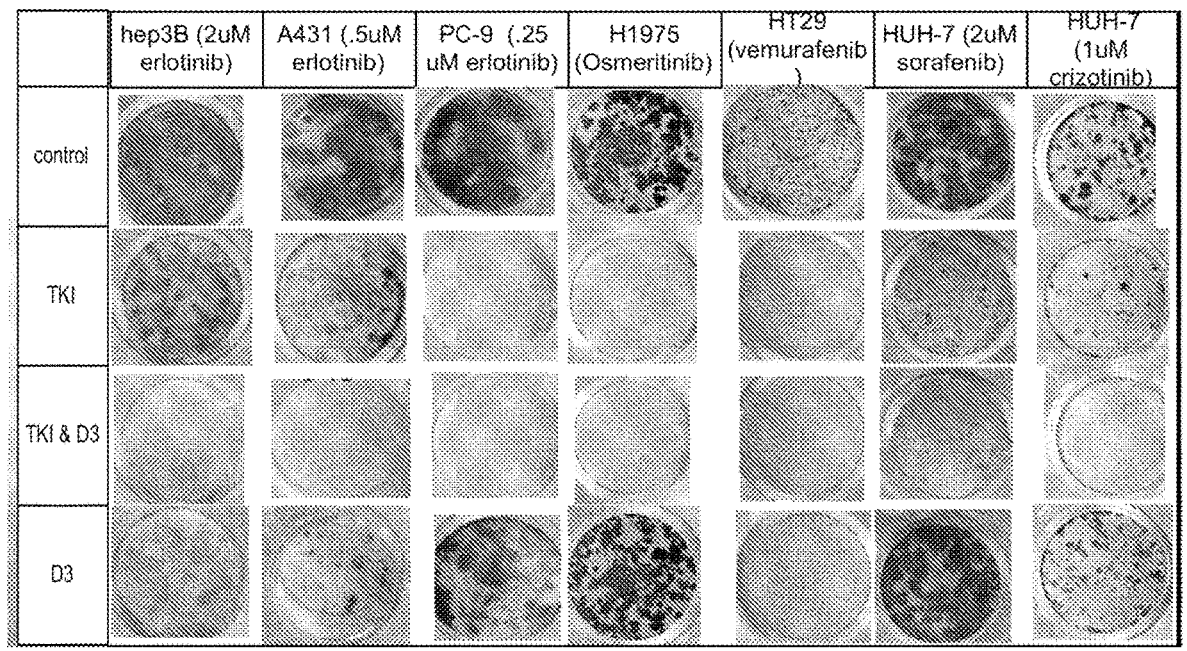
FIG. 21 provides experimental results showing the effect of the chimera D3 on the proliferation of cancer cells treated with erlotinib, osimertinib (AZD9291), vemurafenib, sorafenib, or crizotinib.

Clonal density assays optimized to show survival showed that about 0.4 to 4% of PC-9 cells (number of colonies/total cells plated) survived the treatment with 2 μM gefitinib. The addition of chimera D3 to gefitinib reduced this number by about 100-fold. Moreover, the growth factor IGF1 increased the number of cells surviving gefitinib treatment; the addition of chimera D3 dramatically reduced IGF1-induced cell survival. Furthermore, the addition of bFGF increased the number of surviving cells and increased the growth rate significantly, whereas the addition of chimera D3 substantially reduced cell growth (FIG. 20). The addition of chimera D3 to various TKI's further inhibited cancer cell survival and growth in cell lines representative of human hepatoma, (hep3B and HUH7); head and neck cancer (A431); non-small cell lung cancer (PC-9), non-small cell lung cancer (H1975-T790M gefitinib-resistant); and colon cancer (HT29) (FIG. 21).

Figure 22A:
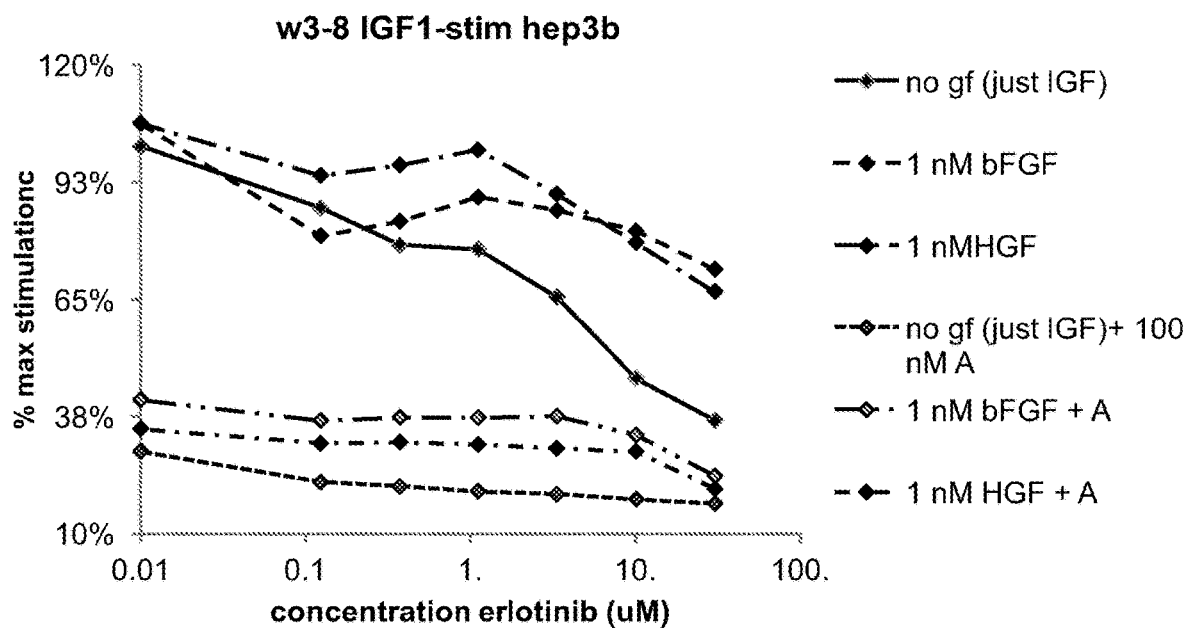
FIG. 22A is a line graph showing the effect of the chimera D3 on the proliferation of hep3B cells treated with erlotinib and various growth factors.

HGF, bFGF, IGF, neuregulin, PDGF, and EGF are widely expressed in tumors and have been studied in growth factor rescue of oncogene addicted cancers (15). Rescue growth factors vary on the TKI used as well as cancer cell types, and multiple growth factors may rescue the treated cell. The chimera A decreased the rescue by HGF, bFGF, or IGF in hep3b cells treated with erlotinib (FIG. 22A).

Figure 22B:
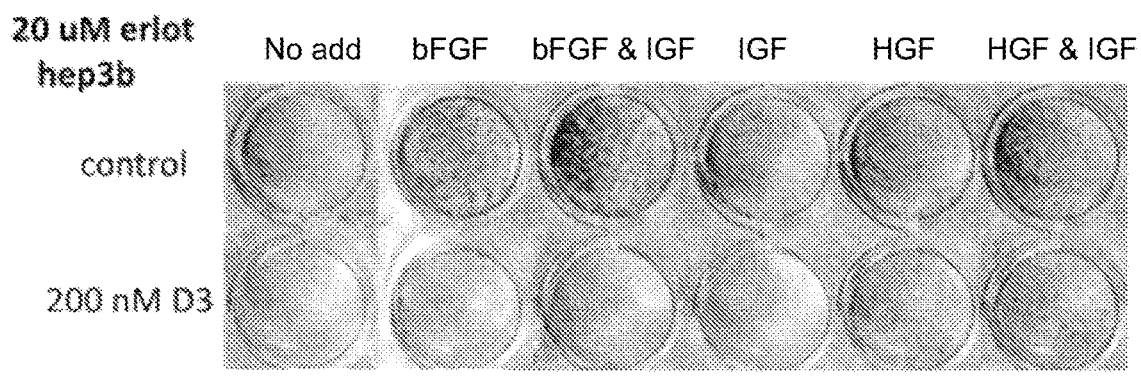
FIG. 22B provides experimental result showing that chimera D3 reversed the effect of bFGF and HGF on erlotinib-treated hep3B cells.
Figure 23:
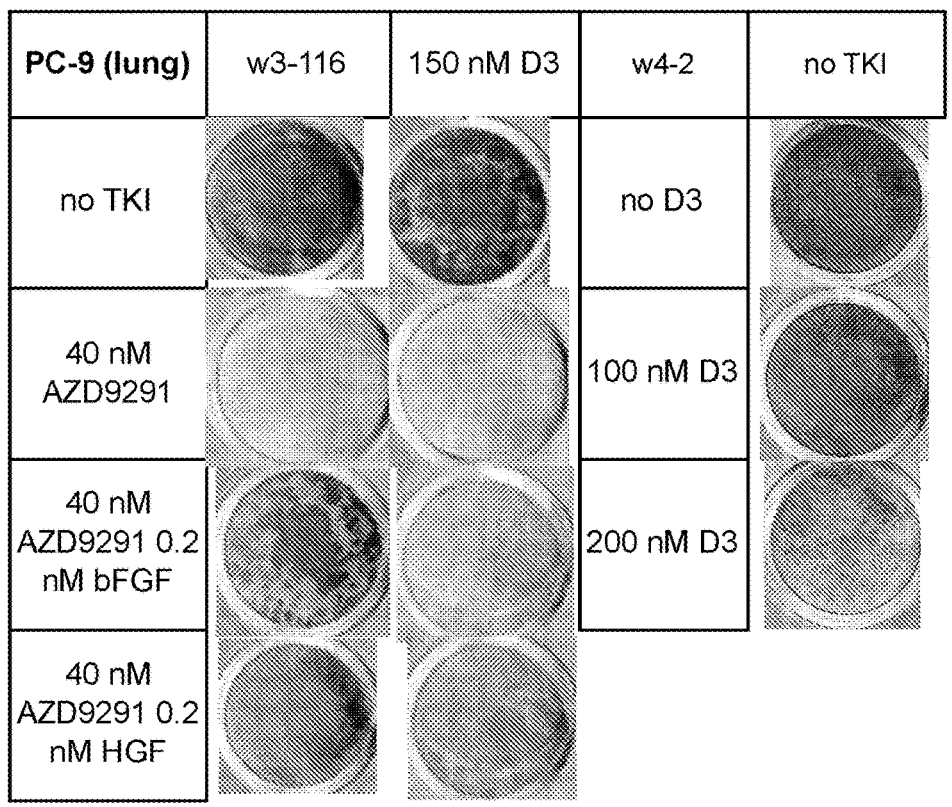
FIG. 23 provides experimental results showing the effect of the chimera D3 on the proliferation of PC-9 cells treated with AZD9291 and various growth factors.

The clonal proliferation assay results provided in FIG. 22B demonstrated the growth factor rescue of erlotinib-treated hep3b hepatocellular carcinoma cells (in control wells), and that the addition of chimera D3 inhibited the bFGF, IGF1, bFGF/IGF1, HGF and HGF/IGF rescue. Also, the results in FIG. 23 demonstrated that bFGF and HGF rescued the osimertinib-treated PC-9 non-small cell lung cancer cells (in control wells), and the addition of chimera D3Fc inhibited such rescue.

Example 13

Figure 24A:
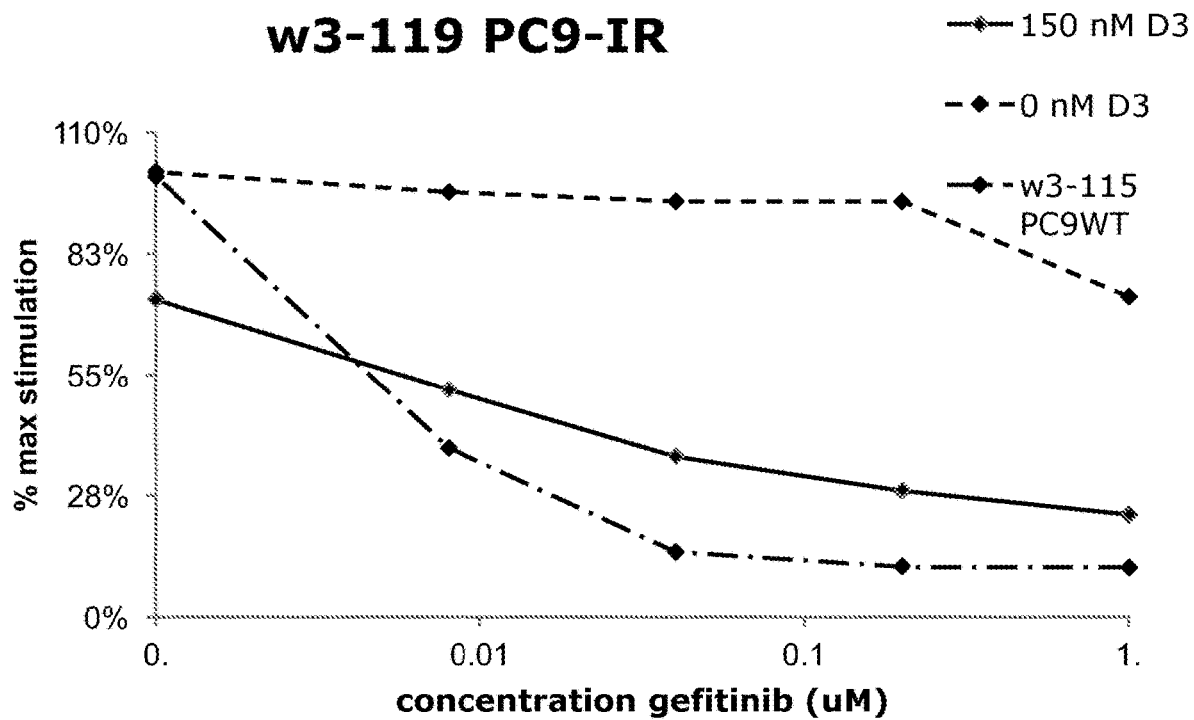
FIG. 24A and FIG. 24B provide experimental results showing the effect of the chimera D3 on the proliferation of gefitinib-resistant PC-91R cells treated with gefitinib.
Figure 24B:
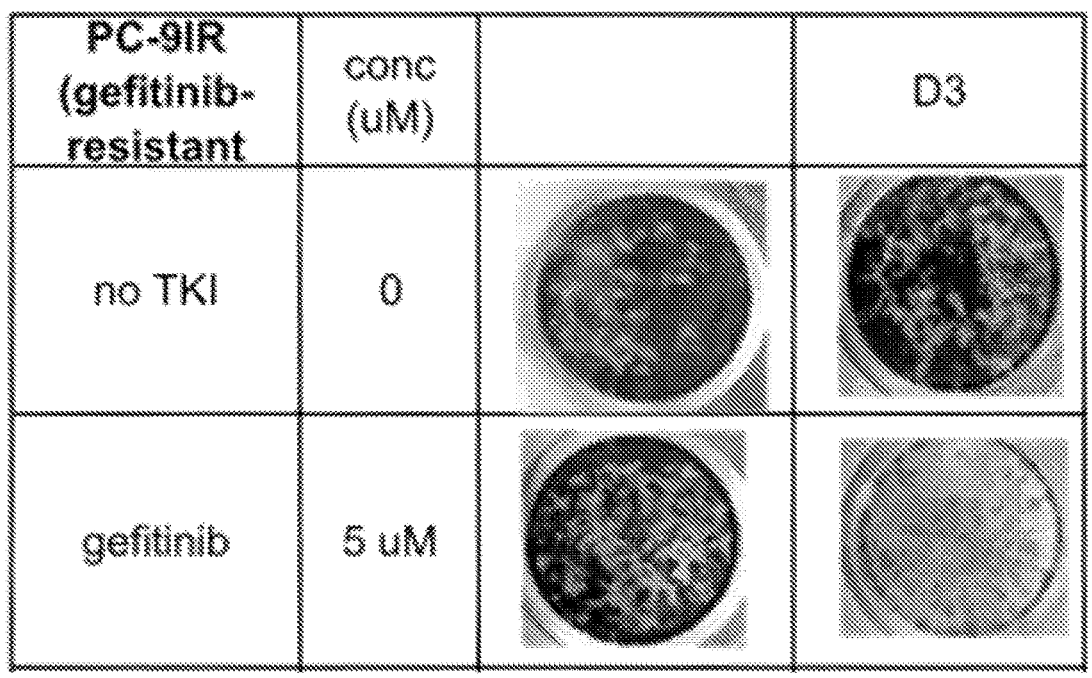

Addition of BP3-Fc Restores Gefitinib Sensitivity to Gefitinib-Resistant Non-Small Cell Cancer Line One mechanism of EGFR TKI resistance is the transition from an epithelial to mesenchymal phenotype (16). PC-91R is a non-small cell carcinoma cell line derived from PC-9 that is resistant to the EGFR TKI gefitinib; it retains the original EGFR mutation but exhibits a mesenchymal phenotype (25). As shown in FIG. 24A and FIG. 24B, the addition of chimera D3 (i.e., the 3(del3)3 chimera) restored the cancer cells' sensitivity to gefitinib. Consequently, a combination of chimera D3 and TKI may limit the resistance caused by epithelial to mesenchymal transition.

Example 14

IGFBP3 Chimera Causes Tumor Regression

Figure 25:
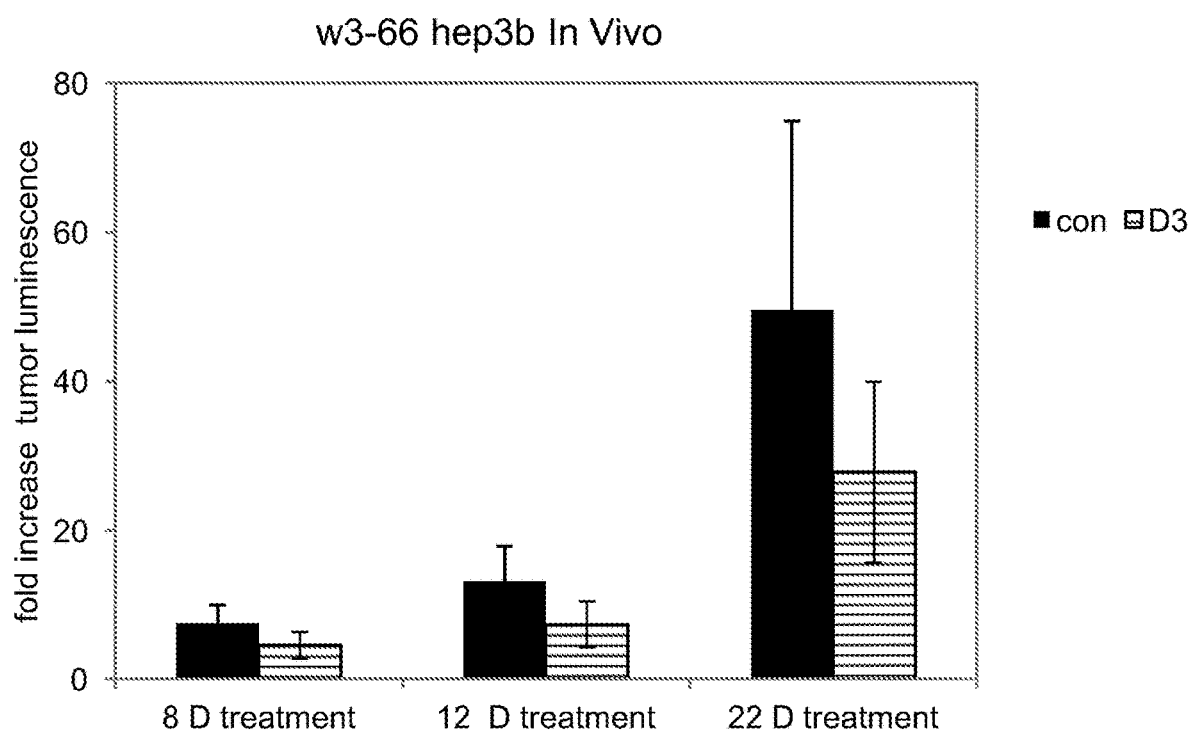
FIG. 25 is a bar graph demonstrating the effect of the chimera D3 hep3B tumor growth in mice.

Hep3B cells were infected with GFP-luciferase lentivirus. The cells with highest GFP expression were selected by FACS sort, and the resulting population was expanded. Two million hep3B cells mixed with Matrigel were injected subcutaneously in NOD-Scid mice, and measurable signal was obtained after 7 days. Treatment began at 8 days after injection (day 0). Luciferase was measured as per the standard Xenogen protocol. IGFBP3.Fc D3 (i.e., the $3(del3)_3$ chimera) at 20 mg/kg was injected twice weekly; saline was injected in the control group. Tumor growth was measured twice weekly by measuring the luminescence. Animals were sacrificed at day 22. The experimental data, as summarized in FIG. 25, demonstrated that D3Fc-treated tumors grew more slowly, compared with that in control mice.

At 12 days of the chimera treatment, two tumors became too small to measure and one tumor decreased in size. By 22 days, the tumor that showed partial regression had become too small to measure, and a fourth tumor decreased to 50% of its maximal size. There was one complete tumor regression in the control group.

Table 9 below summarizes this experiment, in which "progression" means an increase in the tumor size, "partial regression" means a 20% or greater decrease in the tumor size, and "complete regression" means no measurable tumor. Moreover, D3 alone inhibited tumor growth by 37% (p value of 0.0025) on day 25; the T/C (tumor volume treated/control) ratio was 63%.

TABLE 9

|  | Day 12 | | Day 22 | |
| --- | --- | --- | --- | --- |
|  | Control | Chimera D3 | Control | Chimera D3 |
| Progression | 8 | 5 | 8 | 4 |
| Partial progression | 0 | 1 | 0 | 1 |
| Complete regression | 1 | 2 | 1 | 3 |

Example 15

IGFBP3 Chimera Enhances Erlotinib-Induced Tumor Inhibition

5×10exp6 PC-9 non-small cell lung cancer cells were injected subcutaneously in Nod scid gamma (NSG) mice. Tumor volumes were measured by microcaliper using the formula (length×width$^2$/2) and mice were sorted by tumor size to form comparable groups of 10. Erlotinib in 6% captisol was dosed orally daily at 25 mg/kg; IGFBP3Fc (3(del3)3) was dosed intraperitoneally at 25 mg/kg three times per week; control animals were administered vehicle. Dosing was started on day 11; erlotinib and erlotinib plus D3 was discontinued on day 19; D3 injections were discontinued on day 22.

Figure 26:
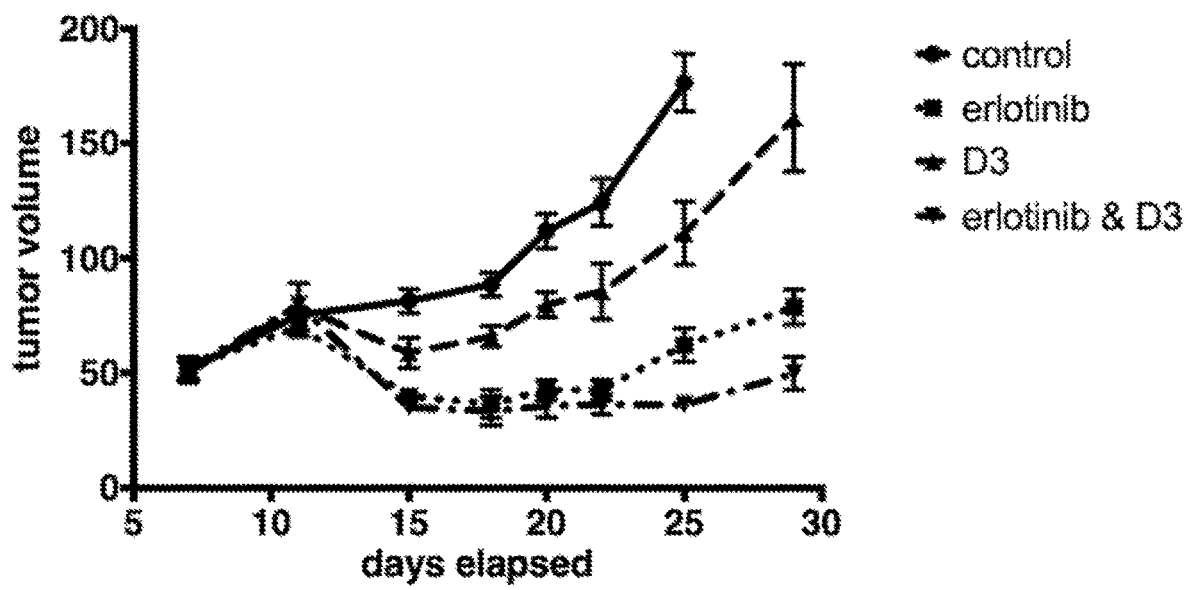
FIG. 26 is a line graph (mean volume and SEM) demonstrating the effect of the erlotinib and/or chimera D3 on PC-9 tumors in mice.

Erlotinib treatment caused tumor regression compared to the control (see, FIG. 26), and exhibited a tumor volume of treated to control (T/C) of 38% at day 20. Furthermore, tumors in chimera D3 plus erlotinib groups (T/C=32% at day 20) were smaller than in the erlotinib group (FIG. 26). More importantly, when erlotinib treatment was stopped on day 19, the chimera D3 plus erlotinib group showed delayed tumor growth, as compared to the erlotinib group. This result supports the use of the combination of erlotinib and chimera D3 to postpone the tumor regression.

Example 16

IGFBP3Fc Enhances Tumor Inhibition at Low Dose Erlotinib

Figure 27:
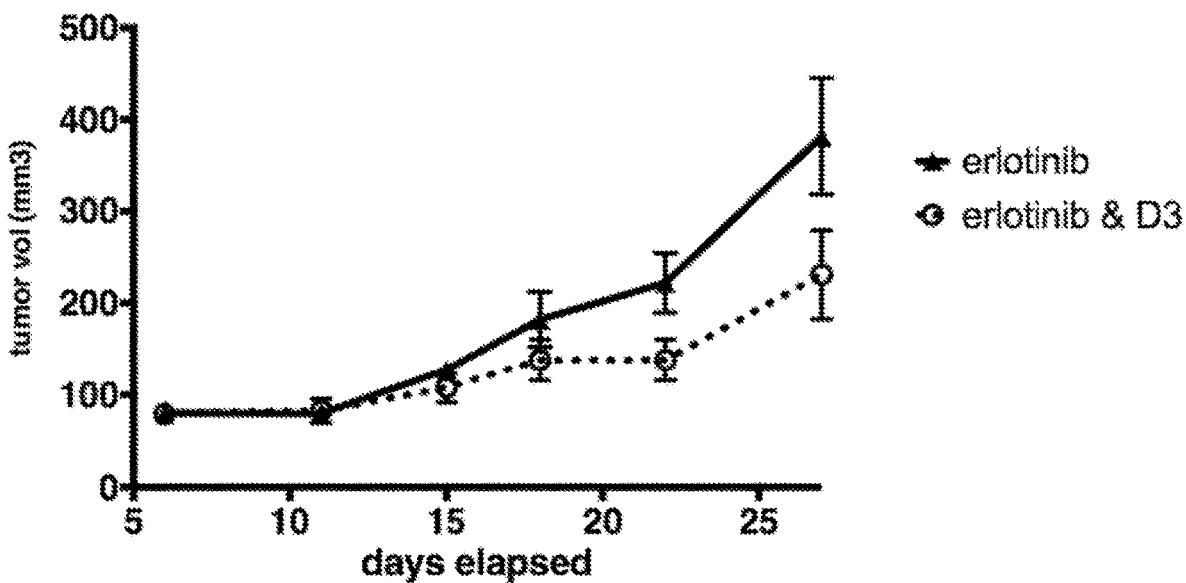
FIG. 27 is a line graph (mean volume and SEM) demonstrating the effect of the erlotinib or chimera D3 plus erlotinib on mice injected with PC-9 cells.

Subcutaneous PC-9 tumors were generated and measured as above. Chimera D3 was dosed as above; erlotinib was dosed at 25 mg/kg 3 times per week in order to examine the effect of the chimera D3 on the tumor growth with suboptimal erlotinib dosing. The treatment started on day 8 and ended on day 22. As shown in FIG. 27, intermittent dosing of erlotinib did not cause the tumor regression as in FIG. 26; however, the addition of the chimera D3 to erlotinib clearly improved the tumor inhibition.

Example 17

In Vivo Studies of Pharmacokinetics

Figure 28:
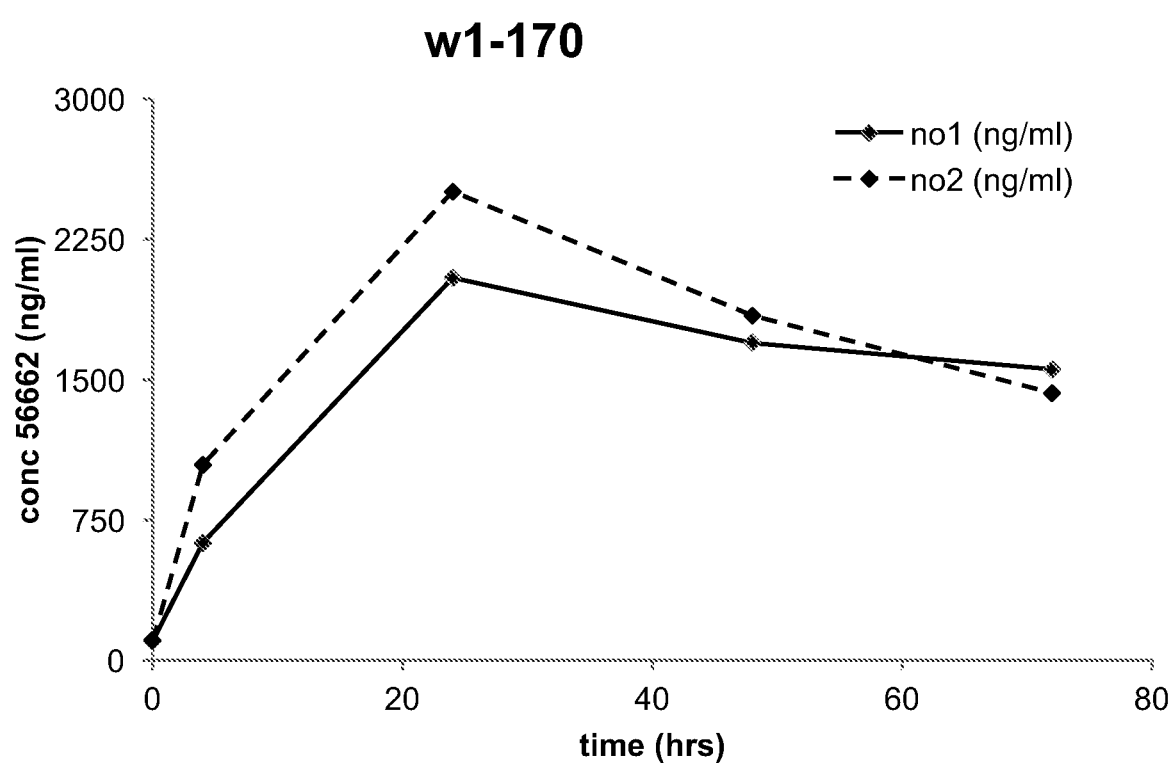
FIG. 28 is a line graph demonstrating the pharmacokinetics of the chimera 56662 in mice.

Serum half-life was measured in mice. 100 µg IGFBP3-Fc or 56662 (4 mg/kg) was injected subcutaneously and mouse serum was harvested at 0, 4, 24, 48, 72 hours after injection. Chimera concentration in serum was measured with the Fc ELISA. At 24 hours, the concentration of 56662 was over 2 µg/ml (FIG. 28), and the serum half-time was estimated to be about 43 hours.

Example 18

Inhibition of Chimeras on Growth Factor-Stimulated Proliferation of hep3B Cells

Table 10 below illustrates an increase in potency of some chimeras with a met domain (met is the HGF receptor) or a syndecan domain and the superiority of an N-terminal position of the added domain. Met3con is the met3 domain Fc; syn in syn-D3 is a fragment of syndecan that has three heparan sulfate glycosylation sites. The increase in potency can be attributed to an increase in the stability as well as the growth factor binding because the IC$_{50}$ is reduced for multiple growth factors.

TABLE 10

|  | D3 (w3-81) | met23D3 (5-31) | met3D3 (5-31) | met34D3 (5-31) | D3met34 | met4D3 (5-31) | syn-D3 (5-31) | met3con |
| --- | --- | --- | --- | --- | --- | --- | --- | --- |
| SEQ ID NO: | 12 | 26 | 27 | 28 | 29 | 30 | 31 | 32 |
| bFGF | 69 | 87 | 16 | 14 | 149 | 18 | 11 | no inh |
| HGF | 47 | 47 | 3 | 2 | 14 | 6 | 1 | no inh |
| IGF1 | 28 | 14 | 2 | 1 | 24 | 2 | 2 | No inh |
| nrg | 78 | 73 | 7 | 10 | 89 | 13 | 5 | No inh |
| FBS | 105 | 75 | 16 | 12 | 128 | 12 | 3 | no inh |

In view of the foregoing, the present inventors discovered that IGFBP3 can bind neuregulin, PDGF (platelet-derived growth factor), HGF (hepatocyte growth factor), VEGF-B (vascular endothelial cell growth factor), Rantes and basic FGF (fibroblast growth factor) with nanomolar affinity. This broad-spectrum growth factor inhibition is unique, and this discovery allows the development of a novel approach to screen for modified IGFBP chimeras that might improve therapeutic activities.

Various IGFBP3 chimeric molecules with improved physical properties have been constructed. By modifying the sequence of IGFBP3 mid-region, the stability against proteolysis and inhibitory activity toward various growth factors are increased, as compared to the naturally occurring sequence of IGFBP3. Insertion of the linker sequences between the N- and C terminal regions of IGFBP3 and between the different receptor domains also affect binding affinities, chimera aggregation and protein expression.

Domain 2 of VEGF receptor 1 and domain 3 of VEGF receptor 2 (VEGF-trap) were added C-terminal to the IGFBP3 domain. The VEGF-trap domain binds VEGF-A, VEGF-B, and PIGF (placental derived growth factor). Another example we have made adds domain 1 of erbB4, which increases the affinity of the chimera to neuregulin by over 100-fold. These domains may be fused in various orders and may be separated by different linker domains.

The IGFBP3 fused to a human Fc domain to increase the binding affinity to BP-3 partners and to increases serum half-life. The serum half-life of IGFBP3 is estimated to be 25 minutes (26); in contrast, the serum half-life of IGFBP3-Fc is estimated to be 20-40 hours.

In view of the foregoing, it is anticipated that the IGFBP3-VEGF-trap may inhibit pathological vascularization. Anti-VEGF therapy is currently the standard treatment for wet age-related macular degeneration. However, long term follow-up showed a decrease in the response to anti-VEGF therapy after two years. In addition, 33% of the patients do not respond. Current evidence suggests that other growth factors such as PDGF BB, IGF, HGF and bFGF contribute to pathological angiogenesis, so inhibition of a combination of factors may yield a higher response rate and a more durable response over VEGF inhibition by itself. Our BP3-VEGF-trap chimera, which inhibits VEGF, PDGF BB plus IGF, HGF, and bFGF, may show improved responses in pathological angiogenesis seen in macular degeneration and diabetic retinopathy. In addition, a single entity may be more cost effective.

It is also anticipated that the IGFBP3-VEGF-trap Fc may inhibit growth and metastasis of cancer cells. Inhibition of VEGF in cancer reduces angiogenesis, and in combination with chemotherapy can improve overall survival. Because VEGF, IGF, PDGF BB, HGF and bFGF also promote cell migration, IGFBP3-VEGF-trap Fc may show a reduction of angiogenesis and metastasis compared to inhibition of VEGF alone.

Activation of growth factor signaling is one mechanism leading to unrestricted growth of cells, and targeting the activated pathway may produce striking remission of cancer. However, target therapy responses are short lived and resistance to the drug develops. One pathway of intrinsic or acquired resistance is through growth factor rescue. The growth factors HGF, FGF, IGF, neuregulin, and EGF (epidermal growth factor) have been shown in vitro to rescue cancer cells from different kinase inhibitors, and rescue can be elicited by one or more different growth factors. We have shown that the IGFBP3 domain can bind and inhibit proliferation stimulated by HGF, bFGF, IGF's and neuregulin. We predict that a combination of targeted therapy with IGFBP3-Fc chimera will reduce growth factor rescue by one or more growth factors and will prolong the response as compared to drug alone.

Treatment of cancer by combination therapy offers numerous advantages to monotherapy. Rational combinations targeting different pathways may bring synergy that kills a higher percentage of cancer cells, reduce the amount of each drug required and decrease side effects, more effectively challenge the heterogeneity of tumors, and decrease resistance.

These chimeras alone or in combination with chemotherapy or targeted therapy may demonstrate improvement in cancer therapy because of the inhibition of multiple growth factors. As one example, addition of IGFBP3 restores the sensitivity Herceptin-resistant breast cancer (9). A chimera containing the IGFBP-VEGF-trap domains should show improved inhibition of angiogenesis over current therapies such as bevacizumab, ranibizumab (this is used in eye only), or aflibercept because of the inhibition of the factors PDGF, HGF, IGF, and bFGF.

In vivo toxicity is expected to be mild to moderate based on studies of transgenic mice overexpressing IGFBPs. These mice show changes in size and metabolism, but the strains are viable and fertile.

It will be understood that the above description of embodiments is given by way of example only and that various modifications may be made by those with ordinary skill in the art.

The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

REFERENCE

1. V. Hwa, Y. Oh, R. G. Rosenfeld, The insulin-like growth factor-binding protein (IGFBP) superfamily. *Endocr Rev* 20, 761-787 (1999).
2. L. A. Bach, S. J. Headey, R. S. Norton, IGF-binding proteins—the pieces are falling into place. *Trends Endocrinol Metab* 16, 228-234 (2005).
3. B. E. Forbes, P. McCarthy, R. S. Norton, Insulin-like growth factor binding proteins: a structural perspective. *Front Endocrinol* (Lausanne) 3, 38 (2012).
4. R. C. Bunn, J. L. Fowlkes, Insulin-like growth factor binding protein proteolysis. *Trends Endocrinol Metab* 14, 176-181 (2003).
5. M. R. Schneider, H. Lahm, M. Wu, A. Hoeflich, E. Wolf, Transgenic mouse models for studying the functions of insulin-like growth factor-binding proteins. *Faseb J* 14, 629-640 (2000).
6. J. V. Silha, L. J. Murphy, Minireview: Insights from insulin-like growth factor binding protein transgenic mice. *Endocrinology* 143, 3711-3714 (2002).
7. K. H. Nguyen, X. H. Yao, A. G. Erickson, S. Mishra, B. L. Nyomba, Glucose Intolerance in Aging Male IGFBP-3 Transgenic Mice: Differential Effects of Human IGFBP-3 and Its Mutant IGFBP-3 Devoid of IGF Binding Ability. *Endocrinology* 156, 462-474 (2015).
8. P. Cohen, Insulin-like growth factor binding protein-3: insulin-like growth factor independence comes of age. *Endocrinology* 147, 2109-2111 (2006).
9. L. Jerome et al., Recombinant human insulin-like growth factor binding protein 3 inhibits growth of human epidermal growth factor receptor-2-overexpressing breast tumors and potentiates herceptin activity in vivo. *Cancer Res* 66, 7245-7252 (2006).
10. I. Kirman, N. Poltoratskaia, P. Sylla, R. L. Whelan, Insulin-like growth factor-binding protein 3 inhibits growth of experimental colocarcinoma. *Surgery* 136, 205-209 (2004).
11. N. Alami et al., Recombinant human insulin-like growth factor-binding protein 3 inhibits tumor growth and targets the Akt pathway in lung and colon cancer models. *Growth Horm IGF Res* 18, 487 (2008).
12. S. Kummar et al., Utilizing targeted cancer therapeutic agents in combination: novel approaches and urgent requirements. *Nat Rev Drug Discov* 9, 843-856 (2010).
13. P. M. LoRusso et al., Accelerating cancer therapy development: the importance of combination strategies and collaboration. Summary of an institute of medicine workshop. *Clin Cancer Res* 18, 6101-6109 (2012).
14. J. Woodcock, J. P. Griffin, R. E. Behrman, Development of Novel Combination Therapies. *New England Journal of Medicine* 364, 985-987 (2011).
15. T. R. Wilson et al., Widespread potential for growth-factor-driven resistance to anticancer kinase inhibitors. *Nature* 487, 505-509 (2012).
16. L. V. Sequist et al., Genotypic and histological evolution of lung cancers acquiring resistance to EGFR inhibitors. *Sci Transl Med* 3, 75ra26 (2011).
17. T. Yamaoka et al., *Acquired Resistance Mechanisms to Combination* Met-TKI/EGFR-TKI Exposure in Met-Amplified EGFR-TKI Resistant Lung Adenocarcinoma Harboring an Activating EGFR Mutation. *Mol Cancer Ther*, (2016).

18. S. K. Denduluri et al., Insulin-like growth factor (IGF) signaling in tumorigenesis and the development of cancer drug resistance. *Genes Dis* 2, 13-25 (2015).
19. A. C. Obenauf et al., Therapy-induced tumour secretomes promote resistance and tumour progression. *Nature* 520, 368-372 (2015).
20. I. Bozic et al., Evolutionary dynamics of cancer in response to targeted combination therapy. *Elife* 2, e00747 (2013).
21. M. Gerlinger et al., Intratumor heterogeneity and branched evolution revealed by multiregion sequencing. *N Engl J Med* 366, 883-892 (2012).
22. J. Holash et al., VEGF-Trap: A VEGF blocker with potent antitumor effects. *Proceedings of the National Academy of Sciences* 99, 11393-11398 (2002).
23. S. V. Sharma et al., A chromatin-mediated reversible drug-tolerant state in cancer cell subpopulations. *Cell* 141, 69-80 (2010).
24. T. Arao et al., Small in-frame deletion in the epidermal growth factor receptor as a target for ZD6474. *Cancer Res* 64, 9101-9104 (2004).
25. T.-H. Chang et al., Slug Confers Resistance to the Epidermal Growth Factor Receptor Tyrosine Kinase Inhibitor. *American journal of respiratory and critical care medicine* 183, 1071-1079 (2011).
26. E. Arany, P. Zabel, D. J. Hill, Rapid clearance of human insulin-like growth factor binding protein-3 from the rat circulation and cellular localization in liver, kidney and stomach. *Growth Regul* 6, 32-41 (1996).

What is claimed is:

1. A recombinant insulin-like growth factor-binding protein-3 (IGFBP3), comprising,
    an IGFBP3 variant having an amino acid sequence of SEQ ID NO: 2, 5, or 6, wherein the IGFBP3 variant has an increased potency in binding at least one first growth factor other than an insulin-like growth factor, as compared with the wild-type IGFBP3; and
    an IgG Fc portion linked to the C-terminus of the IGFBP3 variant.

2. The recombinant IGFBP3 of claim 1, wherein the first growth factor is a vascular endothelial growth factor B (VEGF-B), neuregulin, platelet-derived growth factor (PDGF), hepatocyte growth factor (HGF), basic fibroblast growth factor (bFGF).

3. The recombinant IGFBP3 of claim 1, further comprising a binding domain specific for a second growth factor, wherein the binding domain is linked to the N-terminus of the IGFBP3 or between the IGFBP3 and the IgG Fc portion, and the first and second growth factors are the same or different.

4. The recombinant IGFBP3 of claim 3, wherein the binding domain specific for the second growth factor is a VEGF binding domain.

5. The recombinant IGFBP3 of claim 4, wherein the VEGF binding domain is selected from the group consisting of VEGF receptor 1 domain 2, VEGF receptor 2 domain 3, and a combination thereof.

6. The recombinant IGFBP3 of claim 5, wherein the VEGF binding domain comprises VEGF receptor 1 domain 2 and VEGF receptor 2 domain 3.

7. The recombinant IGFBP3 of claim 4, further comprising a linker inserted between the VEGF binding domain and the IGFBP3 variant.

8. The recombinant IGFBP3 of claim 7, wherein the linker comprises an amino acid sequence of SEQ ID NO: 13.

9. The recombinant IGFBP3 of claim 3, wherein the binding domain specific for the second growth factor is a neuregulin binding domain.

10. The recombinant IGFBP3 of claim 9, wherein the neuregulin binding domain is a receptor tyrosine-protein kinase ErbB4 domain 1.

11. The recombinant IGFBP3 of claim 1, further comprising,
    a neuregulin binding domain, linked to the N-terminus of the IGFBP3 variant;
    a linker, linked to the C-terminus of the IGFBP3 variant; and
    a VEGF binding domain, inserted between to the C-terminus of the linker and the IgG Fc portion.

12. The recombinant IGFBP3 of claim 1, wherein the recombinant IGFBP3 is a dimeric fusion protein, or is PEGylated.

13. A method for treating tumor, wet age-related macular degeneration or diabetic retinopathy, comprising the step of, administering to a subject in need thereof an effective amount of a recombinant IGFBP3 of claim 1.

14. The method of claim 13, further comprising the step of, administering to the subject an effective amount of a targeted therapy agent or a chemotherapy agent.

15. The method of claim 14, wherein the target therapy agent is erlotinib, vemurafenib, afatinib, crizotinib, osimertinib or sorafenib.

16. The method of claim 13, wherein the tumor is resistant to a targeted therapy agent.

17. The method of claim 14, wherein the chemotherapy agent is gemcitabine, cisplatin, or doxorubicin.

18. The method of claim 13, wherein the tumor is resistant to a chemotherapy agent.

* * * * *